United States Patent
Clarke et al.

(10) Patent No.: US 10,463,833 B2
(45) Date of Patent: Nov. 5, 2019

(54) FLUSHABLE CATHETERS

(71) Applicant: Hollister Incorporated, Libertyville, IL (US)

(72) Inventors: John T. Clarke, Galway (IE); Jerome A. Henry, Castlebar (IE); Adam J. Foley, Swords (IE); Horacio Montes de Oca Balderas, Ballina (IE); Shamsedin Rostami, South Cambridgeshire (GB); Enda F. Carter, Ballina (IE); Martin McMenamin, Lifford (IE); John F. Hannan, Enniscrone (IE); Brendan J. Heneghan, Westport (IE); Padraig M. O'Flynn, Ballina (IE); Michael G. Murray, Ballina (IE); Richard Meaney, Westport (IE)

(73) Assignee: Hollister Incorporated, Libertyville, IL (US)

( * ) Notice: Subject to any disclaimer, the term of this patent is extended or adjusted under 35 U.S.C. 154(b) by 229 days.

(21) Appl. No.: 15/102,304

(22) PCT Filed: Dec. 10, 2014

(86) PCT No.: PCT/US2014/069556
§ 371 (c)(1),
(2) Date: Jun. 7, 2016

(87) PCT Pub. No.: WO2015/089189
PCT Pub. Date: Jun. 18, 2015

(65) Prior Publication Data
US 2017/0007802 A1    Jan. 12, 2017

Related U.S. Application Data

(60) Provisional application No. 62/011,204, filed on Jun. 12, 2014, provisional application No. 62/011,266, (Continued)

(51) Int. Cl.
*A61M 25/00*    (2006.01)
*A61M 25/01*    (2006.01)
(Continued)

(52) U.S. Cl.
CPC .......... *A61M 25/0111* (2013.01); *A61L 29/14* (2013.01); *A61M 25/002* (2013.01);
(Continued)

(58) Field of Classification Search
CPC .... A61M 2025/0046; A61M 2025/006; A61M 2205/582; A61M 2209/04;
(Continued)

(56) References Cited

U.S. PATENT DOCUMENTS 1,066,990 A * 7/1913 Briggs ................... B65G 51/06
                                                        406/184
1,573,619 A * 2/1926 Lemmer ................ A47K 13/16
                                                        220/DIG. 21
(Continued)

FOREIGN PATENT DOCUMENTS

CN    2240371    11/1996
CN    101300036 A    11/2008
(Continued)

OTHER PUBLICATIONS

Rachna N. Dave, Hiren M. Joshi, and Vayalam P. Benugopalan, Novel Biocatalytic Polymer-Based Antimicrobial Coatings as Potential Ureteral Biomaterial, Feb. 1, 2011, 44(2): 845-853.
(Continued)

*Primary Examiner* — Adam Marcetich
(74) *Attorney, Agent, or Firm* — Cook Alex Ltd.

(57) ABSTRACT

A flushable catheter configured to facilitate flushing of the catheter down the toilet and for disposal thereof. The flushable catheter optionally having a selected density such that the catheter has a desired buoyancy relative to water. Alternatively or in addition to having a selected density, the flushable catheter optionally includes a water capture ele-
(Continued)

ment that is contacted by flushing water and captures the force of the flushing water to propel the catheter down the toilet and/or across a trapway/U-bend sewer pipe.

19 Claims, 57 Drawing Sheets

Related U.S. Application Data filed on Jun. 12, 2014, provisional application No. 61/915,280, filed on Dec. 12, 2013, provisional application No. 61/915,270, filed on Dec. 12, 2013, provisional application No. 61/915,396, filed on Dec. 12, 2013.

(51) Int. Cl.
  *A61M 25/08* (2006.01)
  *A61L 29/14* (2006.01)

(52) U.S. Cl.
  CPC ...... *A61M 25/007* (2013.01); *A61M 25/0017* (2013.01); *A61M 2025/006* (2013.01); *A61M 2025/0046* (2013.01); *A61M 2205/582* (2013.01); *A61M 2209/04* (2013.01)

(58) Field of Classification Search
  CPC ............ A61M 25/0017; A61M 25/002; A61M 25/007; A61M 25/0111; B65G 51/00; B65G 51/04; B65G 51/06; B65G 51/01
  See application file for complete search history.

(56) References Cited

U.S. PATENT DOCUMENTS

| | | | |
|---|---|---|---|
| 1,744,300 A * | 1/1930 | Dewaide | A47K 13/16 4/245.9 |
| 3,583,391 A | 6/1971 | Cox et al. | |
| 3,621,848 A | 11/1971 | Magovern | |
| 3,633,976 A * | 1/1972 | Kruyer | B65G 51/04 406/112 |
| 3,655,153 A * | 4/1972 | Terrell | B65G 51/06 220/782 |
| 3,702,610 A | 11/1972 | Sheppard et al. | |
| 3,861,396 A | 1/1975 | Vaillancourt et al. | |
| 3,888,433 A * | 6/1975 | Fish | B65G 51/06 406/184 |
| 3,894,540 A | 7/1975 | Bonner, Jr. | |
| 3,946,737 A * | 3/1976 | Kobler | A61F 13/2051 604/385.18 |
| 4,062,363 A | 12/1977 | Bonner, Jr. | |
| 4,066,298 A * | 1/1978 | Sakamoto | B65G 51/06 406/189 |
| 4,100,309 A | 7/1978 | Micklus et al. | |
| 4,140,127 A * | 2/1979 | Cianci | A61M 25/002 604/171 |
| 4,227,533 A | 10/1980 | Godfrey | |
| 4,413,986 A | 11/1983 | Jacobs | |
| 4,465,481 A | 8/1984 | Blake | |
| 4,610,671 A | 9/1986 | Luther | |
| 4,668,221 A | 5/1987 | Luther | |
| 4,762,738 A | 8/1988 | Keyes et al. | |
| 4,769,005 A | 9/1988 | Ginsburg et al. | |
| 4,772,279 A | 9/1988 | Brooks et al. | |
| 4,790,817 A | 12/1988 | Luther | |
| 4,790,831 A | 12/1988 | Skribiski | |
| 4,795,439 A | 1/1989 | Guest | |
| 4,840,622 A | 6/1989 | Hardy | |
| 4,883,699 A | 11/1989 | Aniuk et al. | |
| 4,906,238 A | 3/1990 | Greenfeld et al. | |
| 4,930,942 A * | 6/1990 | Keyes | A61F 5/445 406/49 |
| 4,937,890 A * | 7/1990 | Tafur | A47K 11/12 4/144.1 |
| 4,952,359 A | 8/1990 | Wells | |
| 4,954,129 A | 9/1990 | Giuliani et al. | |
| 4,994,047 A | 2/1991 | Walker et al. | |
| 5,002,526 A | 3/1991 | Herring | |
| 5,009,648 A | 4/1991 | Aronoff et al. | |
| 5,089,535 A | 2/1992 | Malwitz et al. | |
| 5,098,535 A | 3/1992 | Nakakoshi et al. | |
| 5,102,401 A | 4/1992 | Lambert et al. | |
| 5,195,962 A | 3/1993 | Martin et al. | |
| 5,270,086 A | 12/1993 | Hamlin | |
| 5,439,454 A | 8/1995 | Lo et al. | |
| 5,468,526 A | 11/1995 | Allen et al. | |
| 5,472,417 A | 12/1995 | Martin et al. | |
| 5,569,219 A | 10/1996 | Hakki et al. | |
| 5,601,538 A | 2/1997 | Deem | |
| 5,616,126 A | 4/1997 | Malekmehr et al. | |
| 5,625,917 A * | 5/1997 | Hawkins | B08B 9/0553 15/104.061 |
| 5,688,459 A | 11/1997 | Mao et al. | |
| 5,776,611 A | 7/1998 | Elton et al. | |
| 5,792,114 A | 8/1998 | Fiore | |
| 5,800,412 A | 9/1998 | Zhang et al. | |
| 5,804,653 A | 9/1998 | Weng | |
| 5,830,201 A * | 11/1998 | George | A61F 13/15211 604/364 |
| 5,891,123 A * | 4/1999 | Balzar | A61F 13/2051 28/118 |
| 5,902,262 A * | 5/1999 | Bastioli | A61F 13/38 604/1 |
| 5,904,703 A | 5/1999 | Gilson | |
| 5,985,394 A | 11/1999 | Mao et al. | |
| 6,017,334 A | 1/2000 | Rawls | |
| 6,030,369 A | 2/2000 | Engelson et al. | |
| 6,063,063 A | 5/2000 | Harboe et al. | |
| 6,066,120 A | 5/2000 | Whiteside | |
| 6,071,618 A | 6/2000 | Cook, Jr. et al. | |
| 6,090,075 A | 7/2000 | House | |
| 6,213,990 B1 | 4/2001 | Roempke | |
| 6,217,569 B1 | 4/2001 | Fiore | |
| 6,447,835 B1 | 9/2002 | Wang et al. | |
| 6,468,245 B2 | 10/2002 | Alexandersen | |
| 6,471,684 B2 | 10/2002 | Dulak et al. | |
| 6,488,659 B1 | 12/2002 | Rosenman | |
| 6,585,721 B2 | 7/2003 | Fiore | |
| 6,627,586 B2 | 9/2003 | Brooks et al. | |
| 6,656,146 B1 | 12/2003 | Clayman et al. | |
| 6,664,333 B2 | 12/2003 | Wang et al. | |
| 6,713,140 B2 | 3/2004 | McCormack et al. | |
| 6,726,654 B2 | 4/2004 | Rosenman | |
| 6,942,635 B2 | 9/2005 | Rosenblatt et al. | |
| 6,960,224 B2 | 11/2005 | Marino et al. | |
| 6,976,973 B1 | 12/2005 | Ruddell et al. | |
| 7,037,295 B2 | 5/2006 | Tiernan et al. | |
| 7,128,862 B2 | 10/2006 | Wang | |
| 7,156,824 B2 | 1/2007 | Rosenman | |
| 7,182,906 B2 | 2/2007 | Chen | |
| 7,402,620 B2 | 7/2008 | McGhee | |
| 7,553,923 B2 | 6/2009 | Williams | |
| 7,601,158 B2 | 10/2009 | House | |
| 7,641,757 B2 | 1/2010 | Kampa et al. | |
| 7,662,146 B2 | 2/2010 | House | |
| 7,731,740 B2 | 6/2010 | LaFont et al. | |
| 7,789,873 B2 | 9/2010 | Kubalak et al. | |
| 7,815,628 B2 | 10/2010 | Devens, Jr. | |
| 7,820,284 B2 | 10/2010 | Terry | |
| 7,824,517 B2 | 11/2010 | Kampa et al. | |
| 7,833,280 B2 | 11/2010 | Stack et al. | |
| 7,947,031 B2 | 5/2011 | DiMatteo et al. | |
| 8,143,368 B2 | 3/2012 | Domb et al. | |
| 8,168,249 B2 | 5/2012 | Utas et al. | |
| 8,187,254 B2 | 5/2012 | Hissink | |
| 8,388,583 B2 | 3/2013 | Stout | |
| 8,388,585 B2 | 3/2013 | Tomes | |
| 8,469,928 B2 | 6/2013 | Stout | |
| 8,518,019 B2 | 8/2013 | Green | |
| 8,569,402 B2 | 10/2013 | Henderson et al. | |
| 2002/0016574 A1 | 2/2002 | Wang et al. | |
| 2003/0010965 A1* | 1/2003 | Watanabe | G02B 6/4464 254/134.4 |

(56) References Cited

U.S. PATENT DOCUMENTS

| | | | |
|---|---|---|---|
| 2003/0044245 A1* | 3/2003 | Power | B65G 51/06 406/190 |
| 2003/0165647 A1 | 9/2003 | Kaneko et al. | |
| 2003/0187368 A1 | 10/2003 | Sata et al. | |
| 2003/0216704 A1* | 11/2003 | George | A61F 13/15211 604/364 |
| 2003/0228434 A1 | 12/2003 | Bailey et al. | |
| 2004/0122382 A1 | 6/2004 | Johnson et al. | |
| 2004/0122403 A1* | 6/2004 | Mitchler | A61F 13/15211 604/385.17 |
| 2004/0193124 A1* | 9/2004 | Mizutani | A61F 13/15211 604/364 |
| 2004/0210180 A1 | 10/2004 | Altman | |
| 2004/0023258 A1 | 11/2004 | Kawabata et al. | |
| 2004/0220550 A1 | 11/2004 | Schryver | |
| 2004/0230177 A1 | 11/2004 | DiMatteo et al. | |
| 2005/0049577 A1 | 3/2005 | Snell et al. | |
| 2005/0109648 A1 | 5/2005 | Kerzman et al. | |
| 2005/0131386 A1 | 6/2005 | Freeman et al. | |
| 2005/0148959 A1* | 7/2005 | Przepasniak | A61F 13/15211 604/358 |
| 2005/0163844 A1 | 7/2005 | Ashton | |
| 2005/0197627 A1 | 9/2005 | Huang et al. | |
| 2005/0218154 A1 | 10/2005 | Selsby | |
| 2005/0277862 A1 | 12/2005 | Anand | |
| 2005/0283111 A1 | 12/2005 | Maurice | |
| 2006/0142736 A1* | 6/2006 | Hissink | A61F 11/002 604/540 |
| 2006/0173422 A1 | 8/2006 | Reydel et al. | |
| 2006/0240064 A9 | 10/2006 | Hunter et al. | |
| 2007/0043333 A1 | 2/2007 | Kampa et al. | |
| 2007/0078412 A1 | 4/2007 | McGuckin, Jr. et al. | |
| 2007/0088330 A1 | 4/2007 | House | |
| 2007/0203502 A1 | 8/2007 | Makker et al. | |
| 2007/0225649 A1 | 9/2007 | House | |
| 2007/0269271 A1* | 11/2007 | Smith, II | F16L 55/24 405/183.5 |
| 2008/0015527 A1 | 1/2008 | House | |
| 2008/0091145 A1 | 4/2008 | House | |
| 2008/0097411 A1 | 4/2008 | House | |
| 2008/0118544 A1 | 5/2008 | Wang | |
| 2008/0147049 A1 | 6/2008 | House et al. | |
| 2008/0167598 A1* | 7/2008 | Gann | A61F 13/266 604/14 |
| 2008/0171991 A1 | 7/2008 | Kourakis | |
| 2008/0171998 A1 | 7/2008 | House | |
| 2008/0172042 A1 | 7/2008 | House | |
| 2008/0183262 A1 | 7/2008 | Dowling | |
| 2008/0255510 A1 | 10/2008 | Wang | |
| 2008/0268193 A1 | 10/2008 | Cherry et al. | |
| 2008/0292776 A1 | 11/2008 | Dias et al. | |
| 2008/0312550 A1 | 12/2008 | Nishtala | |
| 2009/0018530 A1 | 1/2009 | Nielsen et al. | |
| 2009/0036874 A1 | 2/2009 | Horowitz et al. | |
| 2009/0250370 A1 | 10/2009 | Whitchurch | |
| 2009/0264869 A1 | 10/2009 | Schmid et al. | |
| 2010/0030197 A1 | 2/2010 | House | |
| 2010/0049146 A1 | 2/2010 | Nielsen et al. | |
| 2010/0098746 A1 | 4/2010 | King | |
| 2010/0100116 A1 | 4/2010 | Brister et al. | |
| 2010/0137743 A1 | 6/2010 | Nishtala et al. | |
| 2010/0145315 A1 | 6/2010 | House | |
| 2010/0198195 A1 | 8/2010 | Nishtala et al. | |
| 2010/0204682 A1 | 8/2010 | Tanghoj et al. | |
| 2010/0209472 A1 | 8/2010 | Wang | |
| 2010/0215708 A1 | 8/2010 | Zumbuehl et al. | |
| 2010/0312255 A1 | 12/2010 | Satake et al. | |
| 2010/0323189 A1 | 12/2010 | Illsley et al. | |
| 2011/0030130 A1* | 2/2011 | Stein | A61F 5/4556 4/144.2 |
| 2011/0049146 A1 | 3/2011 | Illsley et al. | |
| 2011/0071507 A1 | 3/2011 | Svensson et al. | |
| 2011/0114520 A1 | 5/2011 | Matthison-Hansen | |
| 2011/0125135 A1 | 5/2011 | Ahmed | |
| 2011/0160662 A1 | 6/2011 | Stout | |
| 2011/0178425 A1 | 7/2011 | Nishtala | |
| 2011/0212157 A1 | 9/2011 | Edelson et al. | |
| 2011/0238163 A1 | 9/2011 | Andrews et al. | |
| 2011/0268938 A1 | 11/2011 | Schuhmann | |
| 2012/0035530 A1 | 2/2012 | Wang | |
| 2012/0121919 A1 | 5/2012 | Nielsen | |
| 2013/0131646 A1 | 5/2013 | Gilman | |
| 2013/0157236 A1* | 6/2013 | Yang | G09B 19/0076 434/247 |
| 2013/0319890 A1* | 12/2013 | Davis | A61F 13/5518 206/440 |
| 2013/0345681 A1 | 12/2013 | Hong | |
| 2014/0350451 A1* | 11/2014 | Lewis | A61F 13/208 604/11 |

FOREIGN PATENT DOCUMENTS

| | | |
|---|---|---|
| DE | 10 2011 119160 A1 | 5/2013 |
| EP | 0010171 A1 | 4/1980 |
| EP | 0166998 B1 | 1/1986 |
| EP | 0613672 A1 | 9/1994 |
| EP | 0628586 B1 | 12/1994 |
| EP | 0692276 A2 | 1/1996 |
| EP | 1062920 A1 | 12/2000 |
| EP | 1110561 A2 | 6/2001 |
| EP | 1415671 | 5/2004 |
| EP | 2026846 A1 | 2/2009 |
| EP | 2301595 A1 | 3/2011 |
| EP | 2520412 | 11/2012 |
| EP | 2609956 A1 | 7/2013 |
| GB | 2083762 | 3/1982 |
| GB | 2496901 A | 5/2013 |
| JP | S-61209655 A | 9/1986 |
| JP | 01-136662 | 9/1989 |
| JP | 11151293 | 6/1999 |
| KR | 2000/065291 A | 11/2000 |
| KR | 100754057 B | 8/2007 |
| WO | WO 89/05671 A | 6/1989 |
| WO | WO 96/41653 A1 | 12/1996 |
| WO | WO 1998/058989 A1 | 12/1998 |
| WO | WO 00/30696 | 6/2000 |
| WO | WO 2006/055847 A2 | 5/2006 |
| WO | WO 2006/071813 A2 | 7/2006 |
| WO | WO 2007/122269 A1 | 11/2007 |
| WO | WO 2007/140320 A2 | 12/2007 |
| WO | WO 2010/043565 A1 | 4/2010 |
| WO | WO 2011/076211 A1 | 6/2011 |
| WO | WO 2012/163413 A1 | 12/2012 |
| WO | WO 2012/166967 A1 | 12/2012 |
| WO | WO 2014/193402 A1 | 12/2014 |

OTHER PUBLICATIONS

Beom Soo Kim, Jeffrey S. Hrkach, Robert Langer, Biodegradable photo-crosslinked poly(ether-ester) networks for lubricious coatings, Biomaterials, vol. 21, Issue 3, Feb. 2000, pp. 259-265.

A.K. Singla, M. Chawla, Chitosan some pharmaceutical and biological aspects, an update, Journal of Pharmacy and Pharmacology, Aug. 2001, 53: 1047-1067.

FreeStyle Vie Flushable Colostomy Bag by CliniMed Ltd., retrieved from http://www.clinimed.co.uk/Stoma-Care/Products/Closed-Stoma-Bags/Freestyle-Vie-Flushable/Product-Design.aspx Jan. 1, 2014.

International Search Report and Written Opinion dated Aug. 28, 2015, for International Application No. PCT/US2014/069556.

* cited by examiner

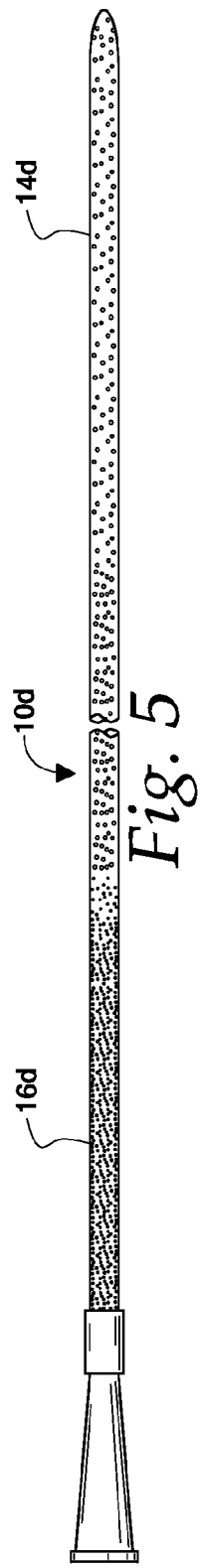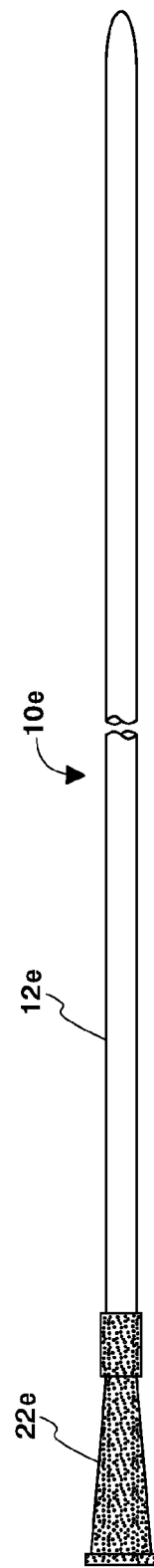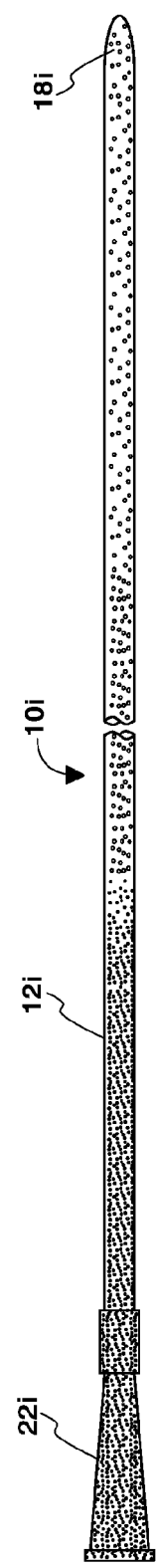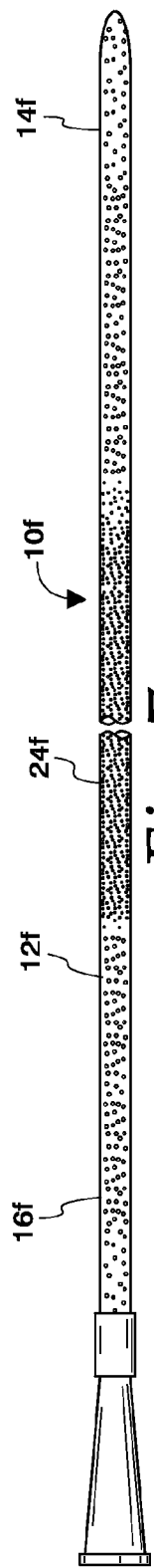

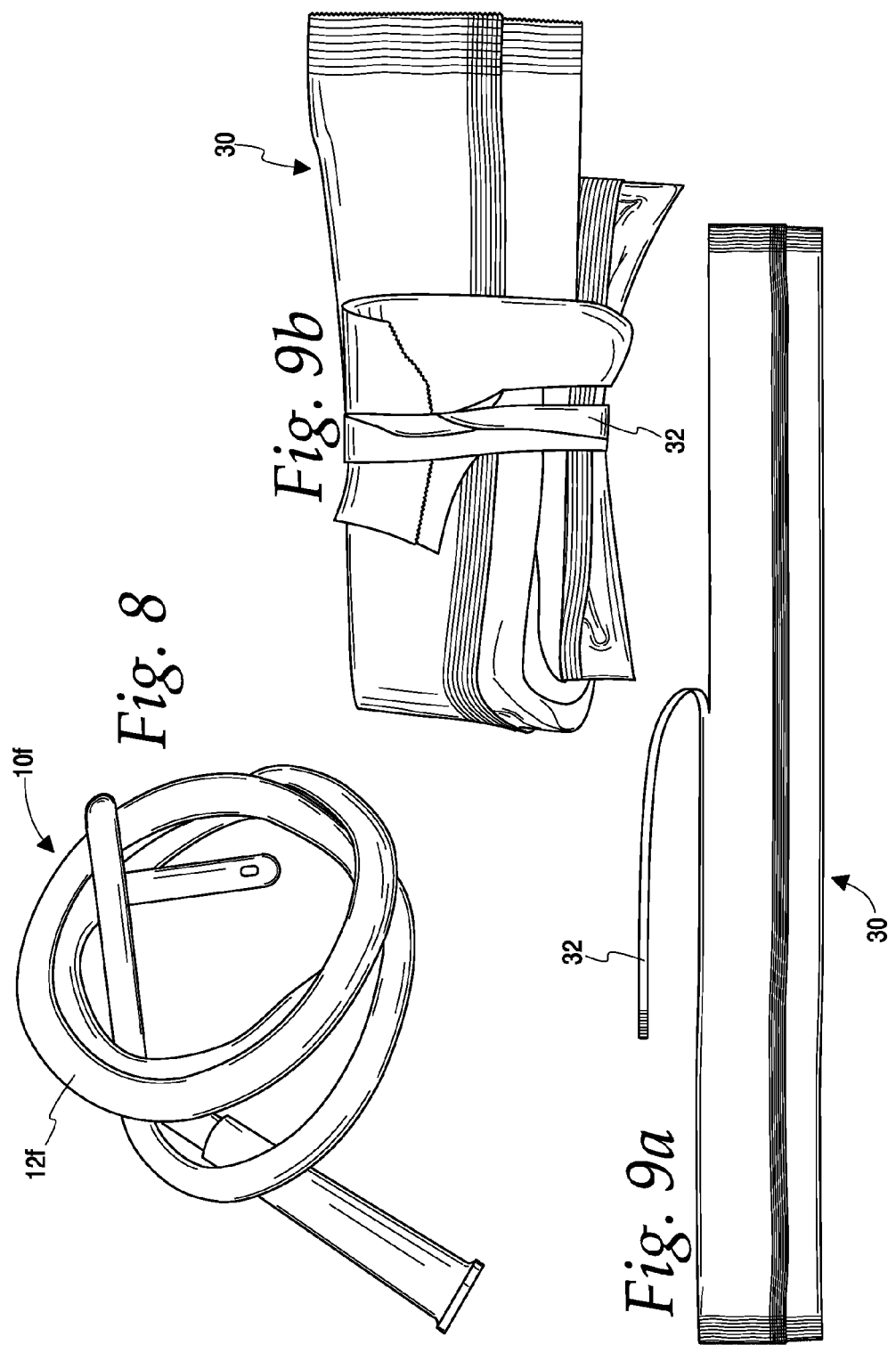

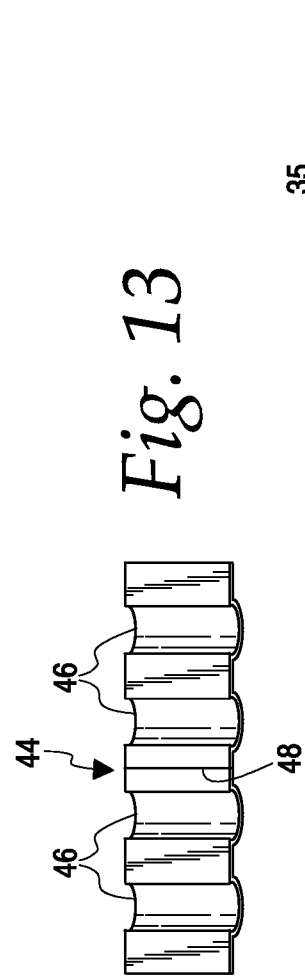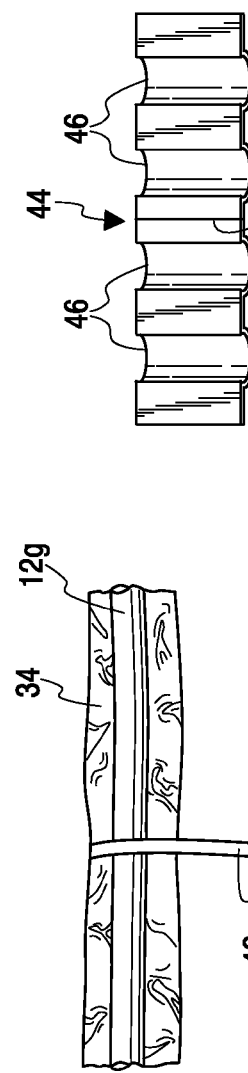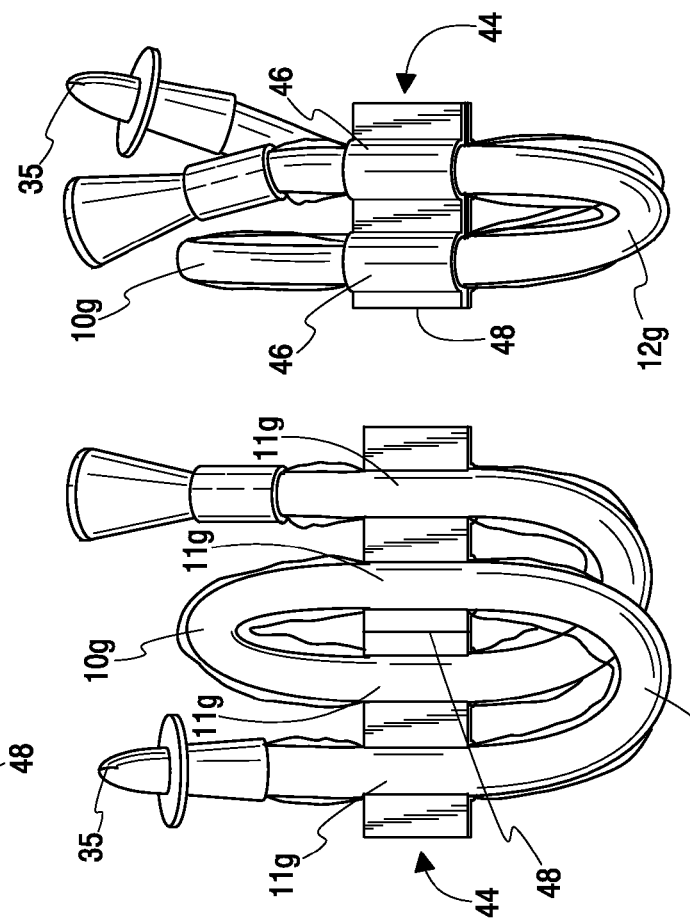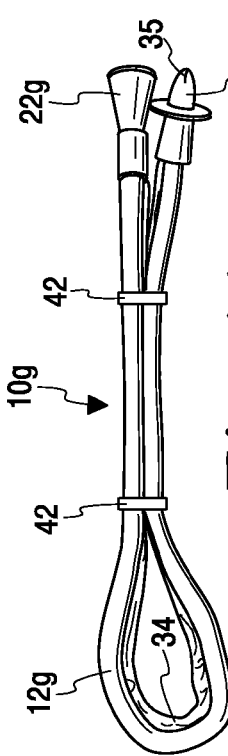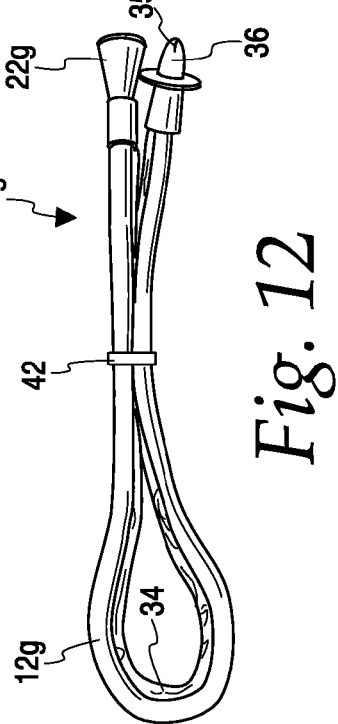
Fig. 10
Fig. 11
Fig. 12
Fig. 13
Fig. 14
Fig. 15

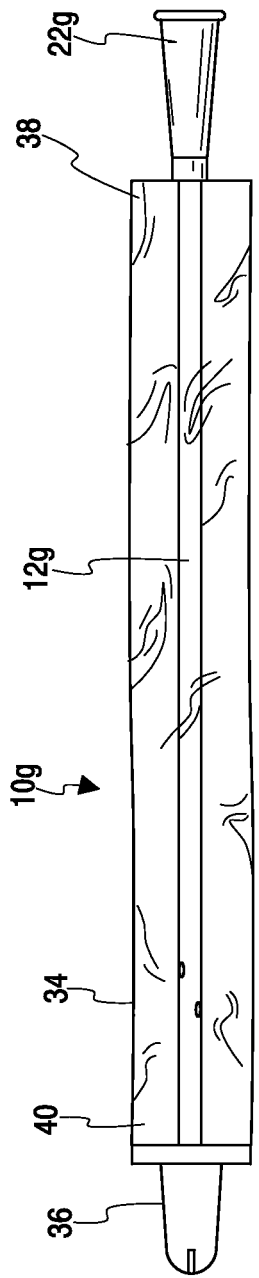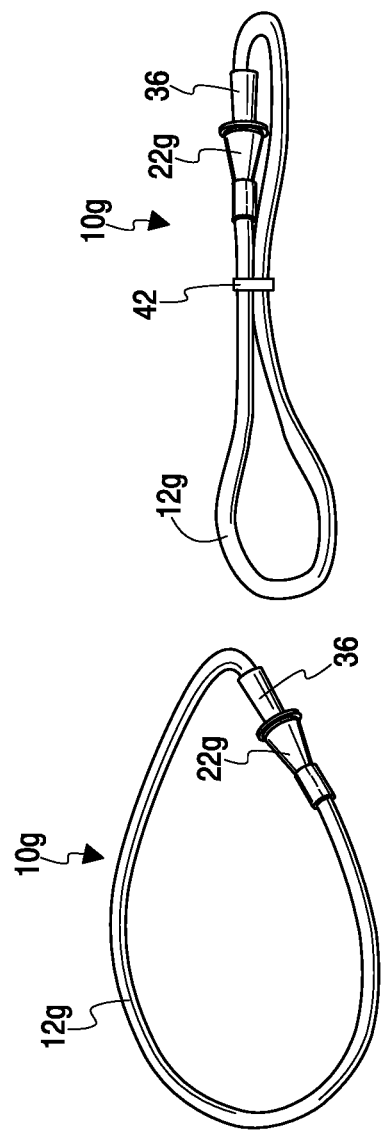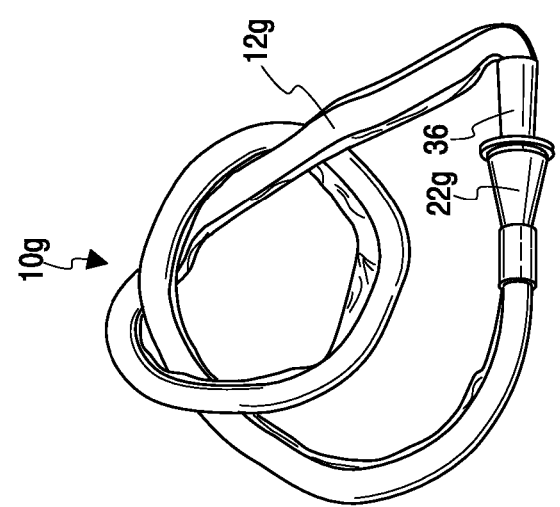

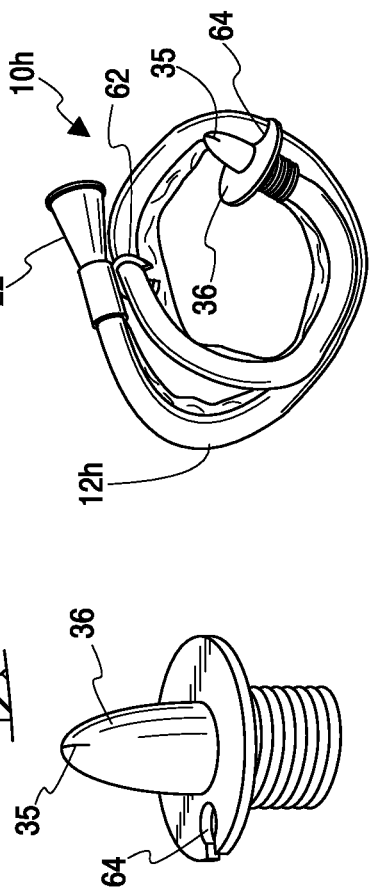
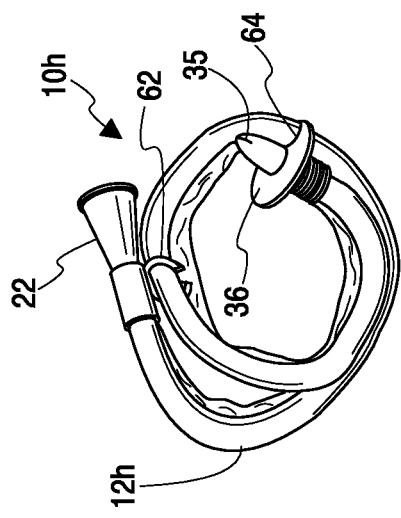
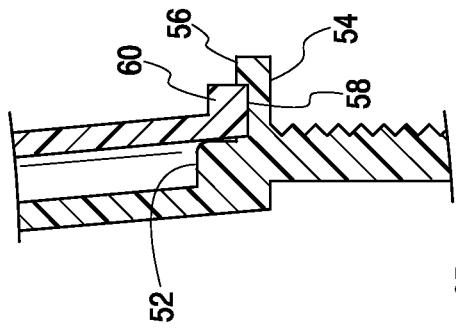
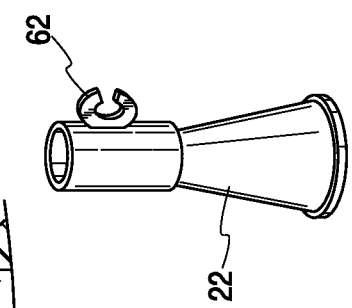
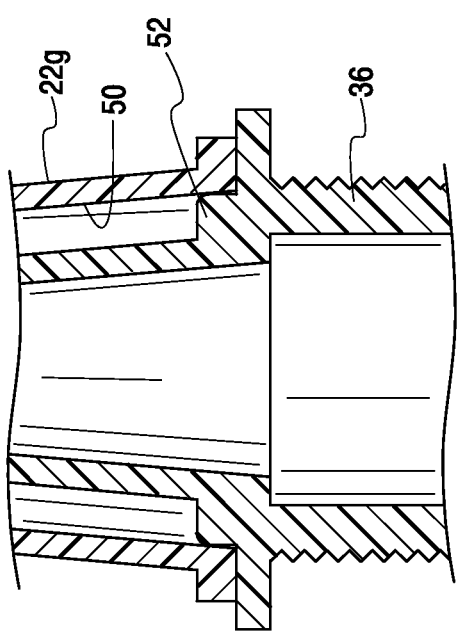

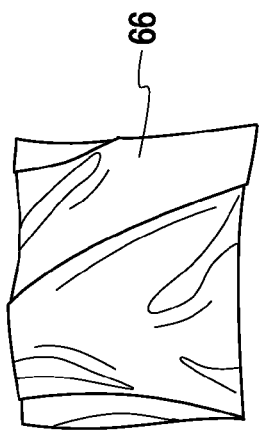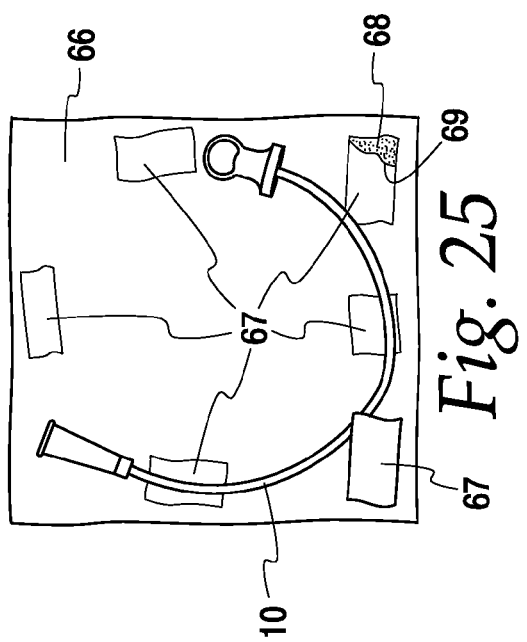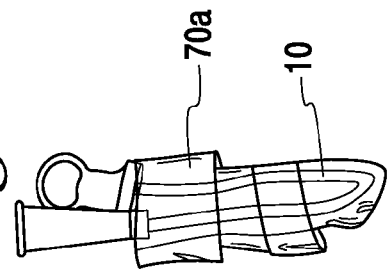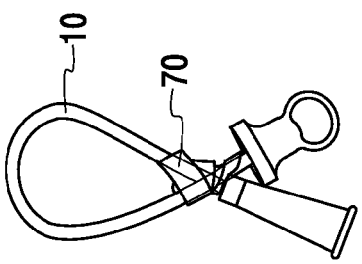

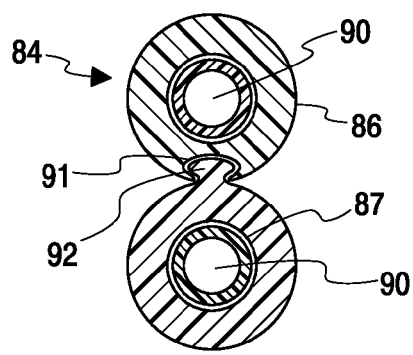
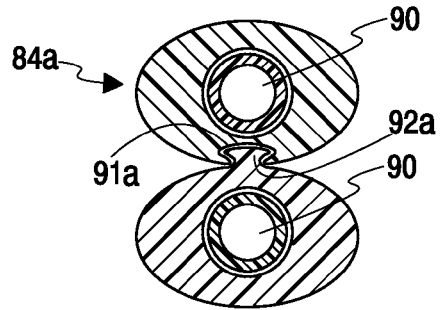
Fig. 41    Fig. 42
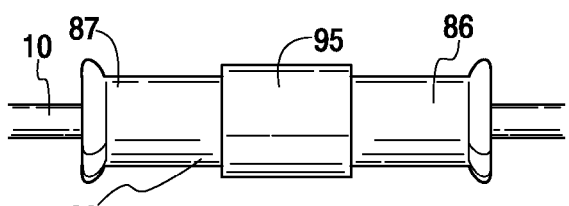
Fig. 43
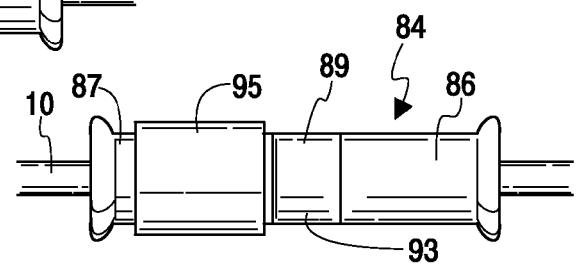
Fig. 44
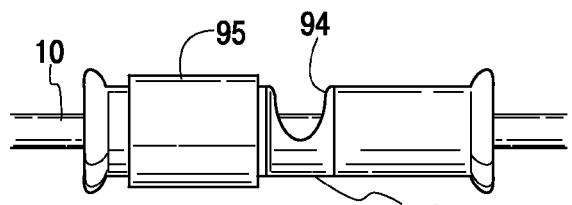
Fig. 45
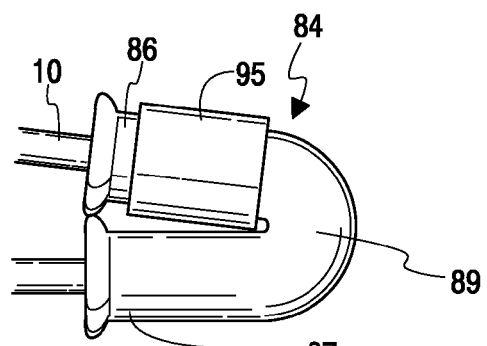
Fig. 46

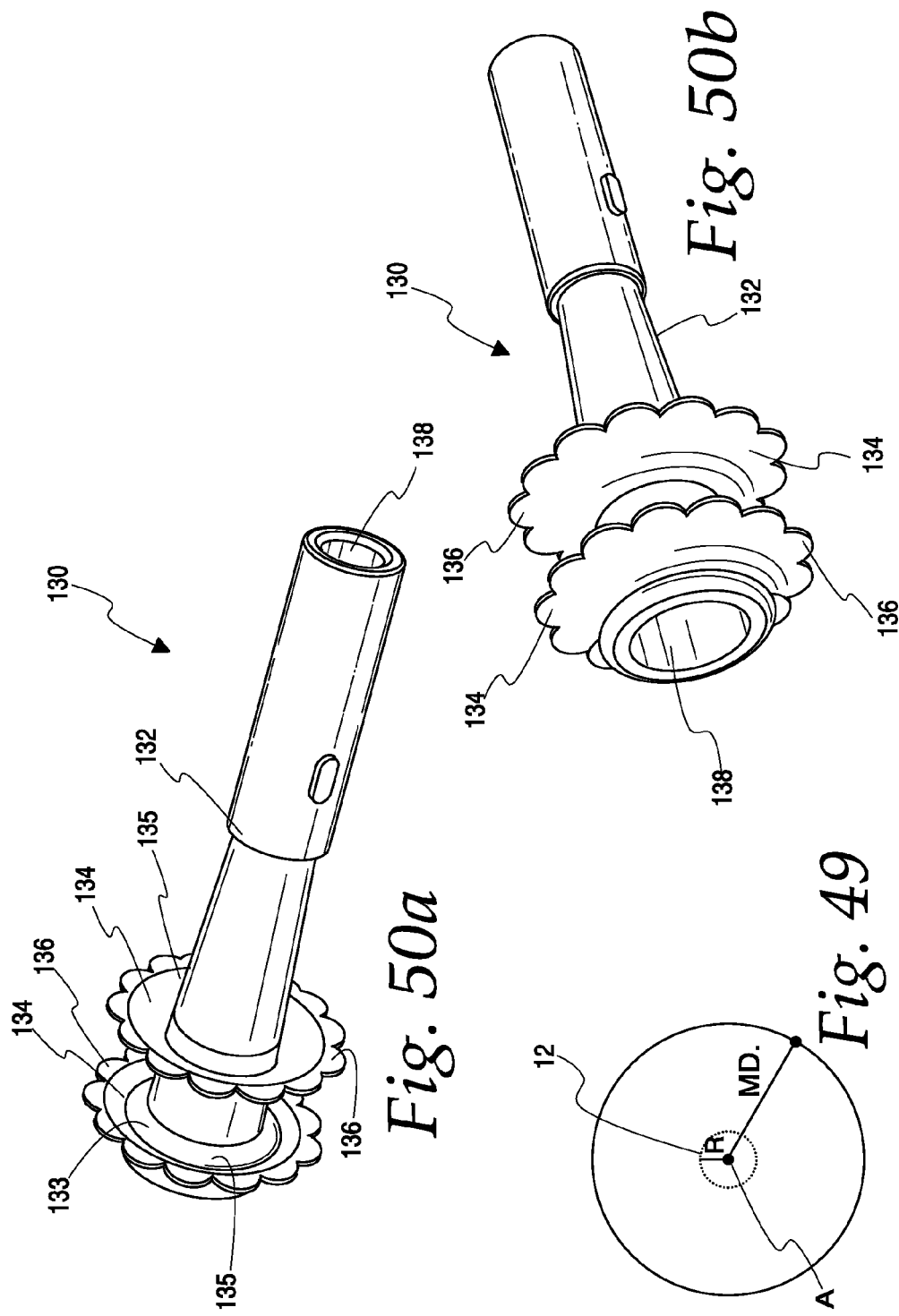

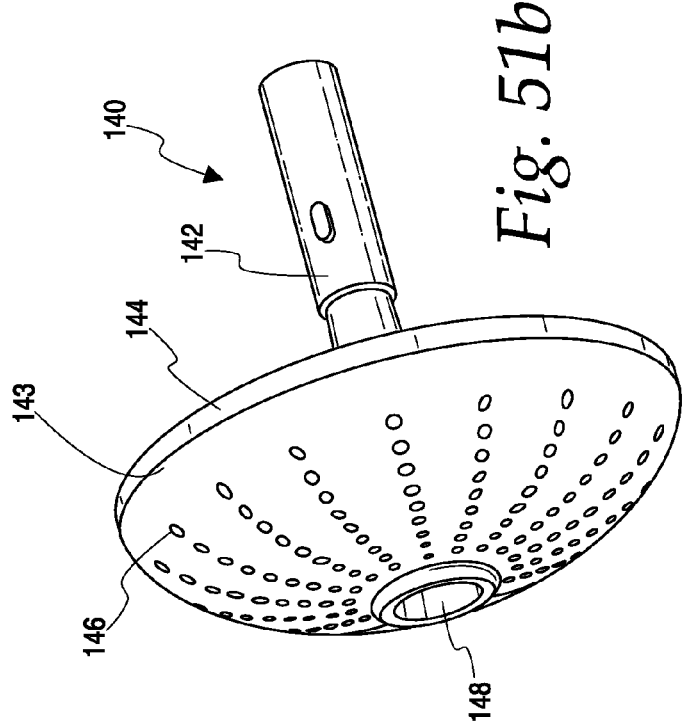
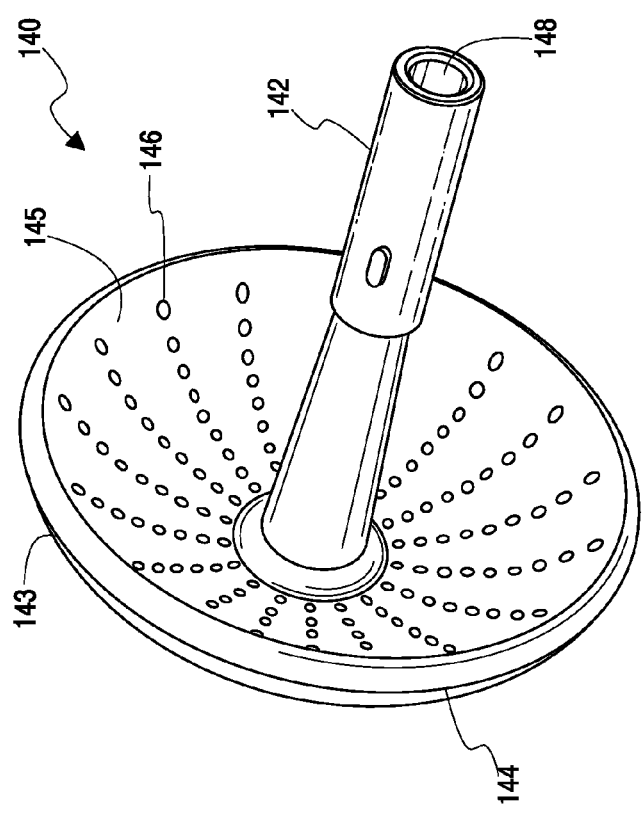
Fig. 51a
Fig. 51b

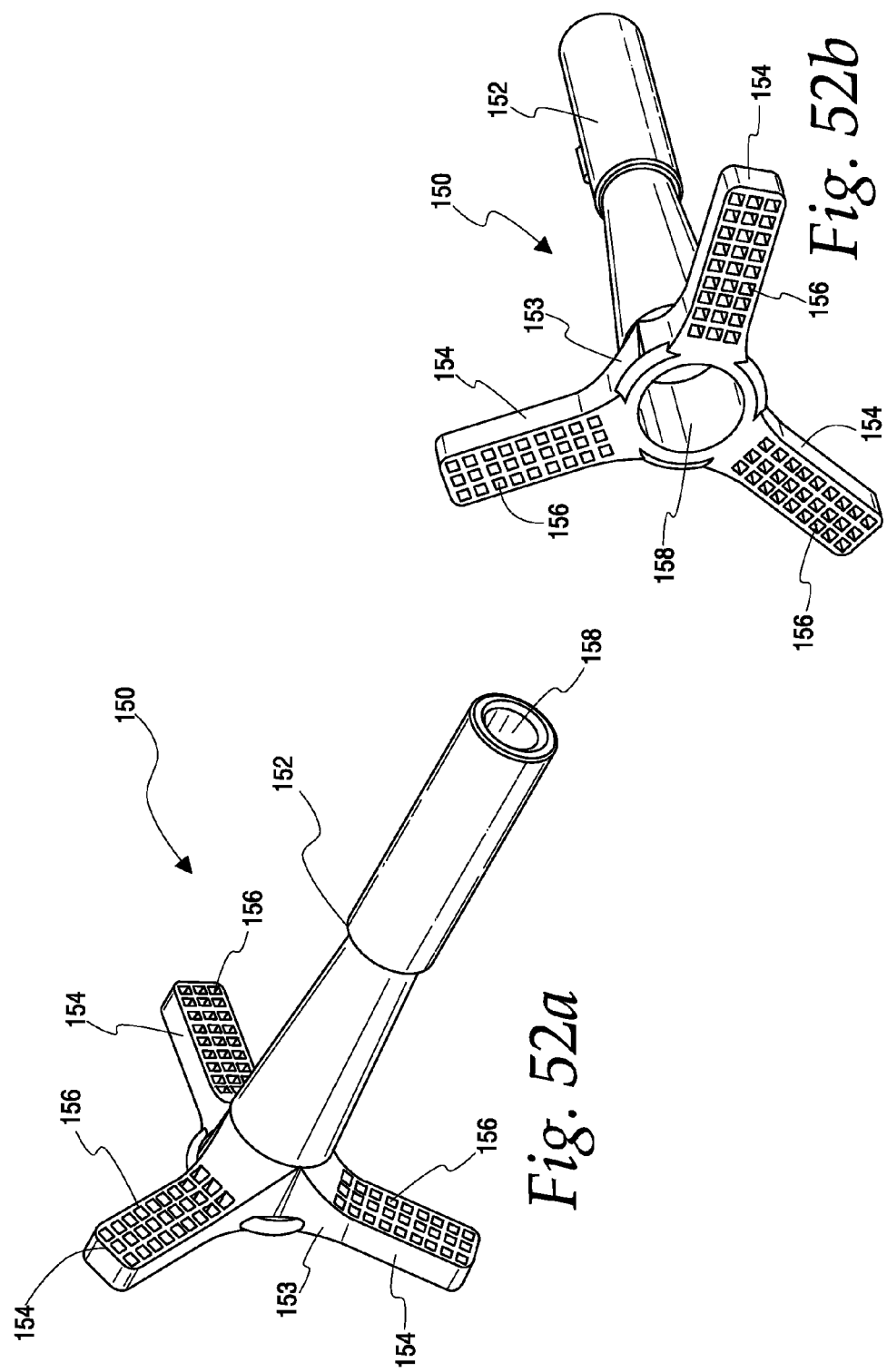

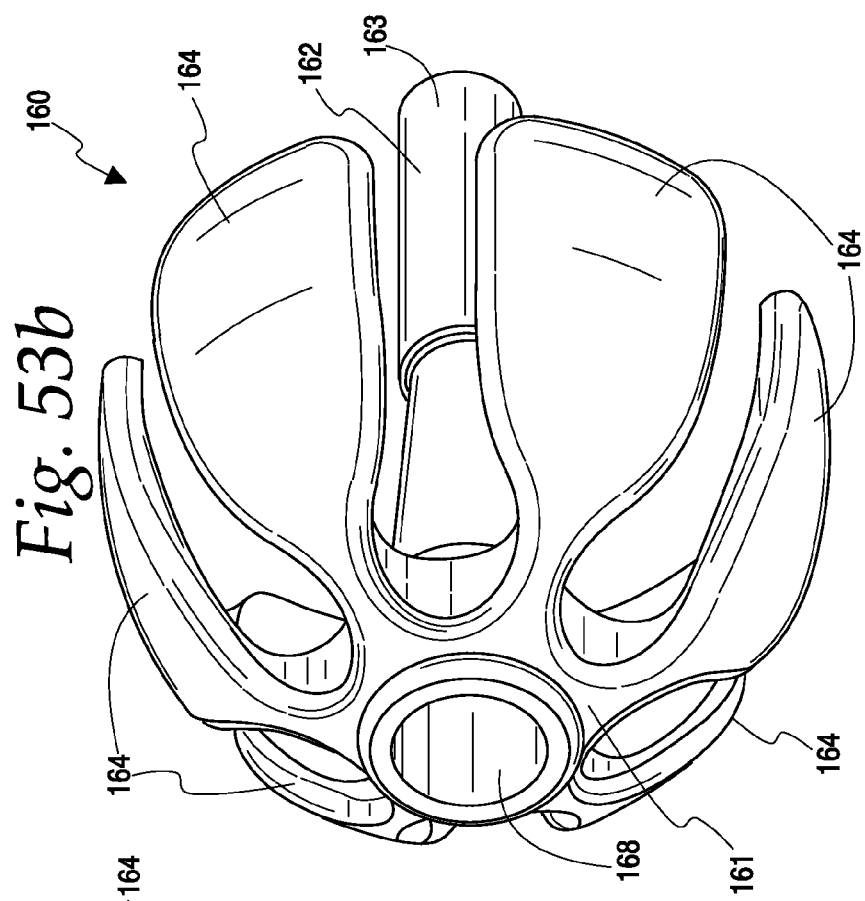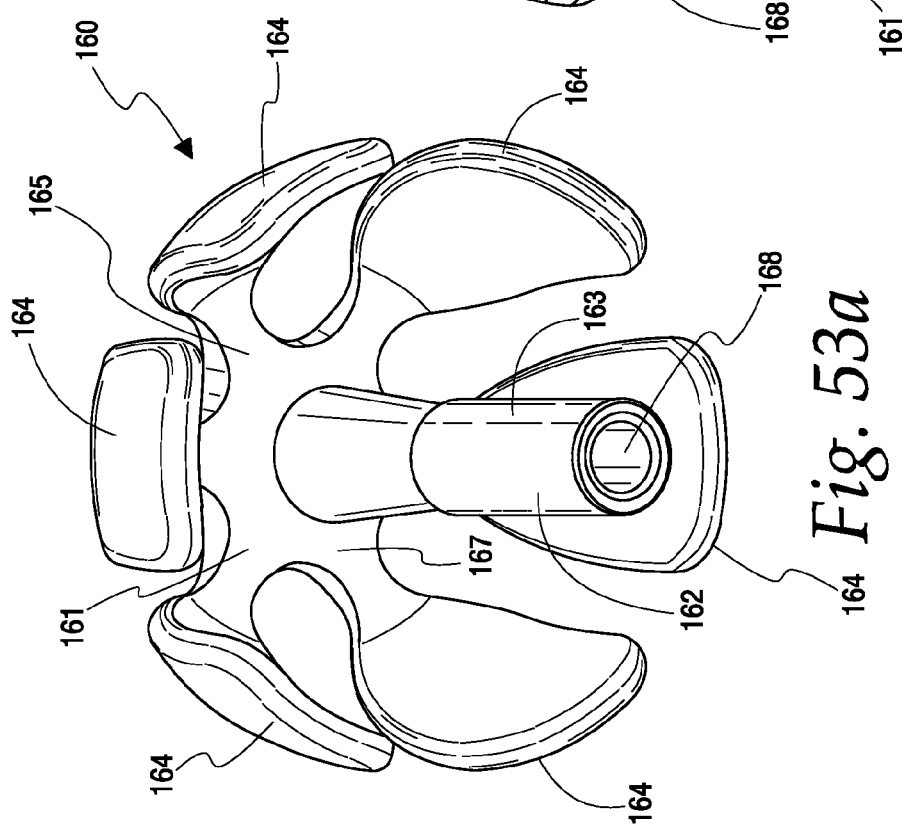

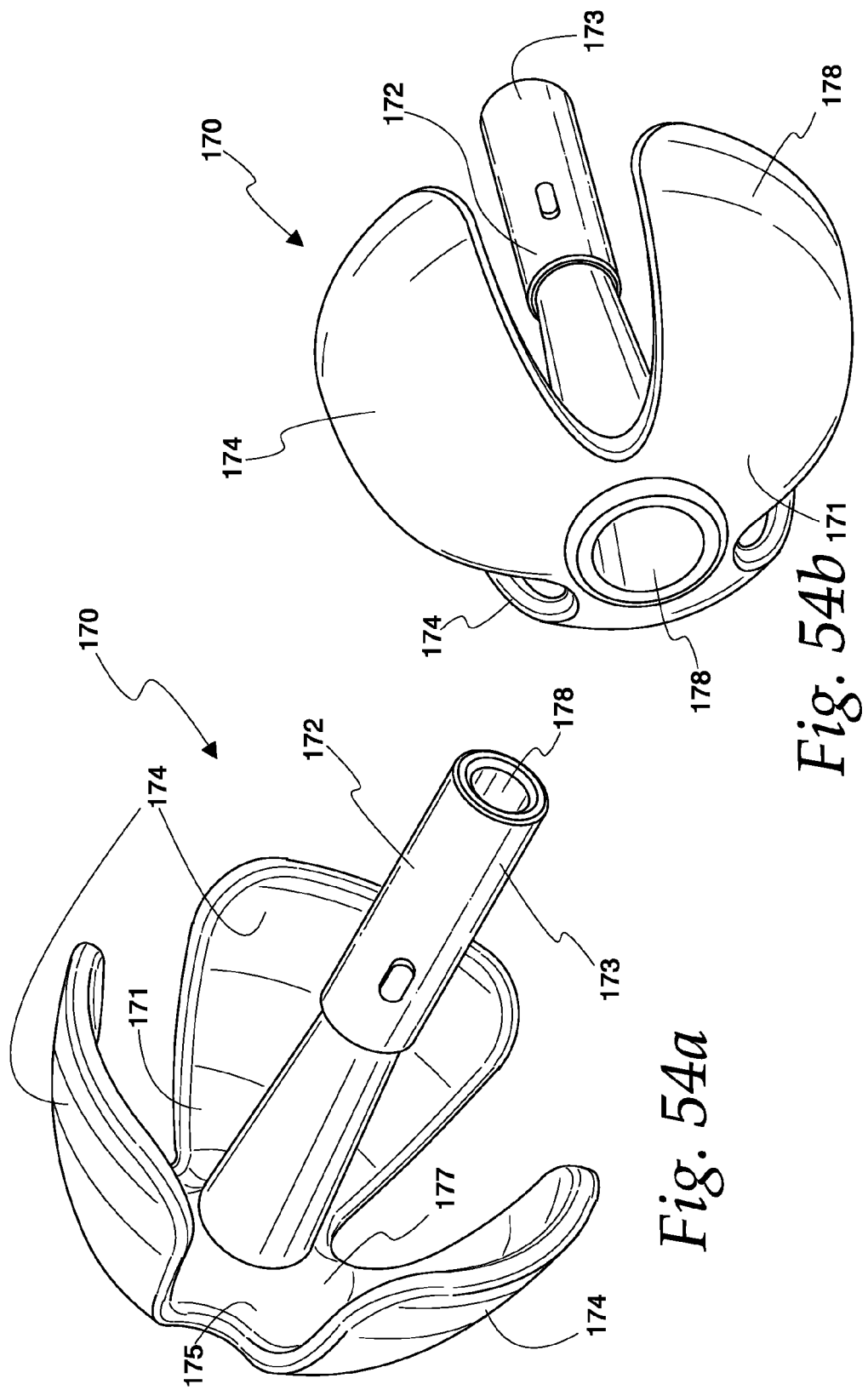

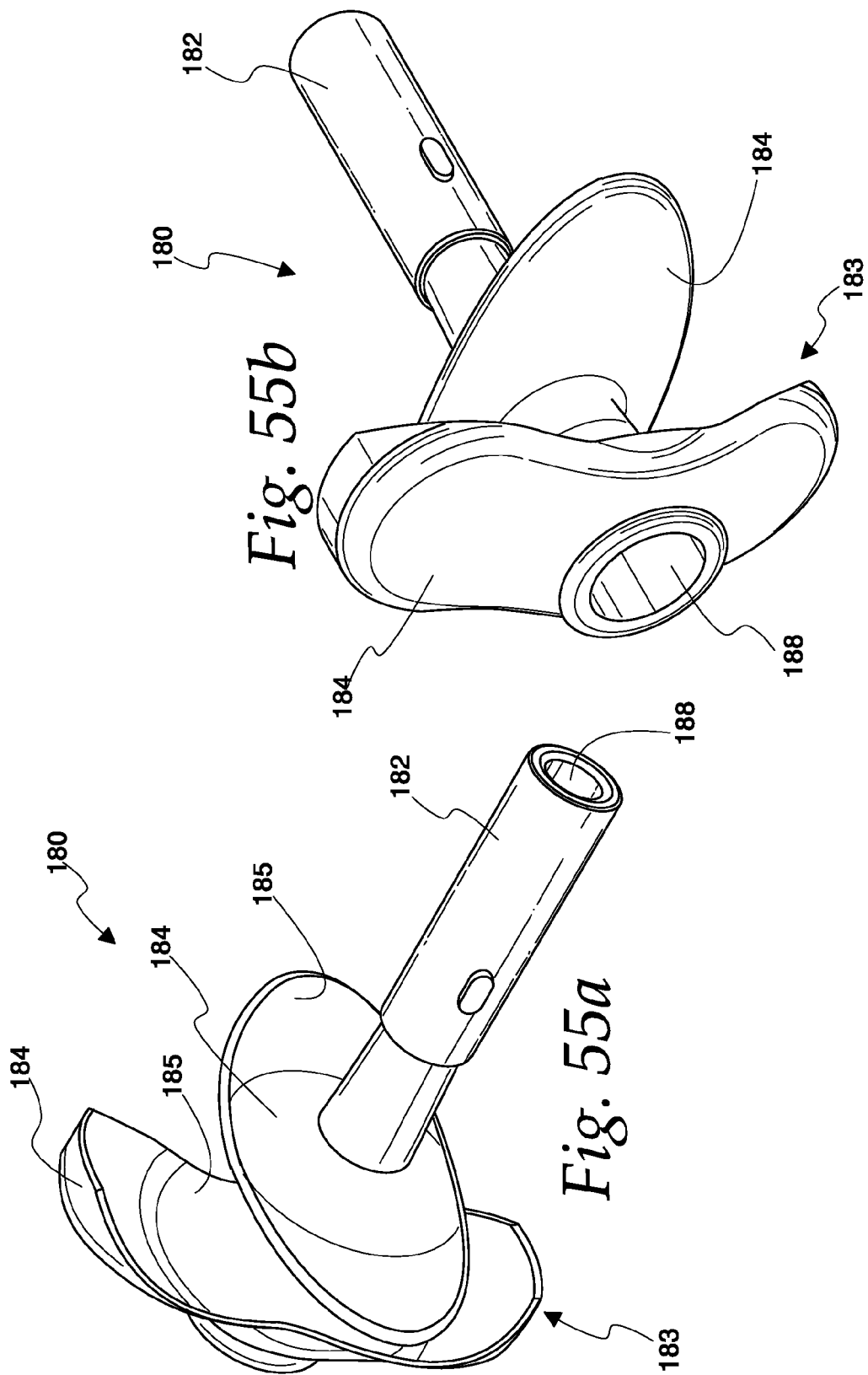

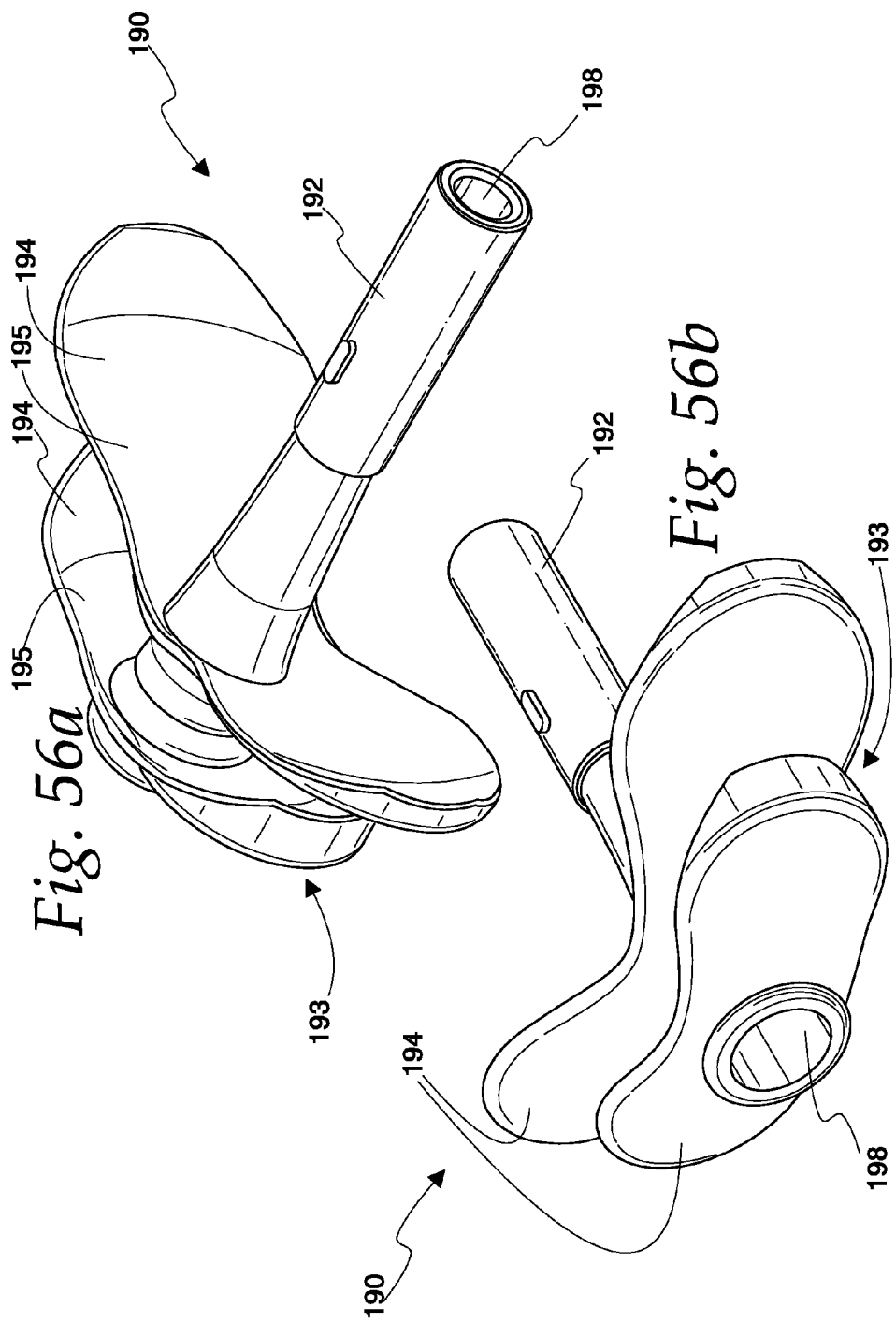

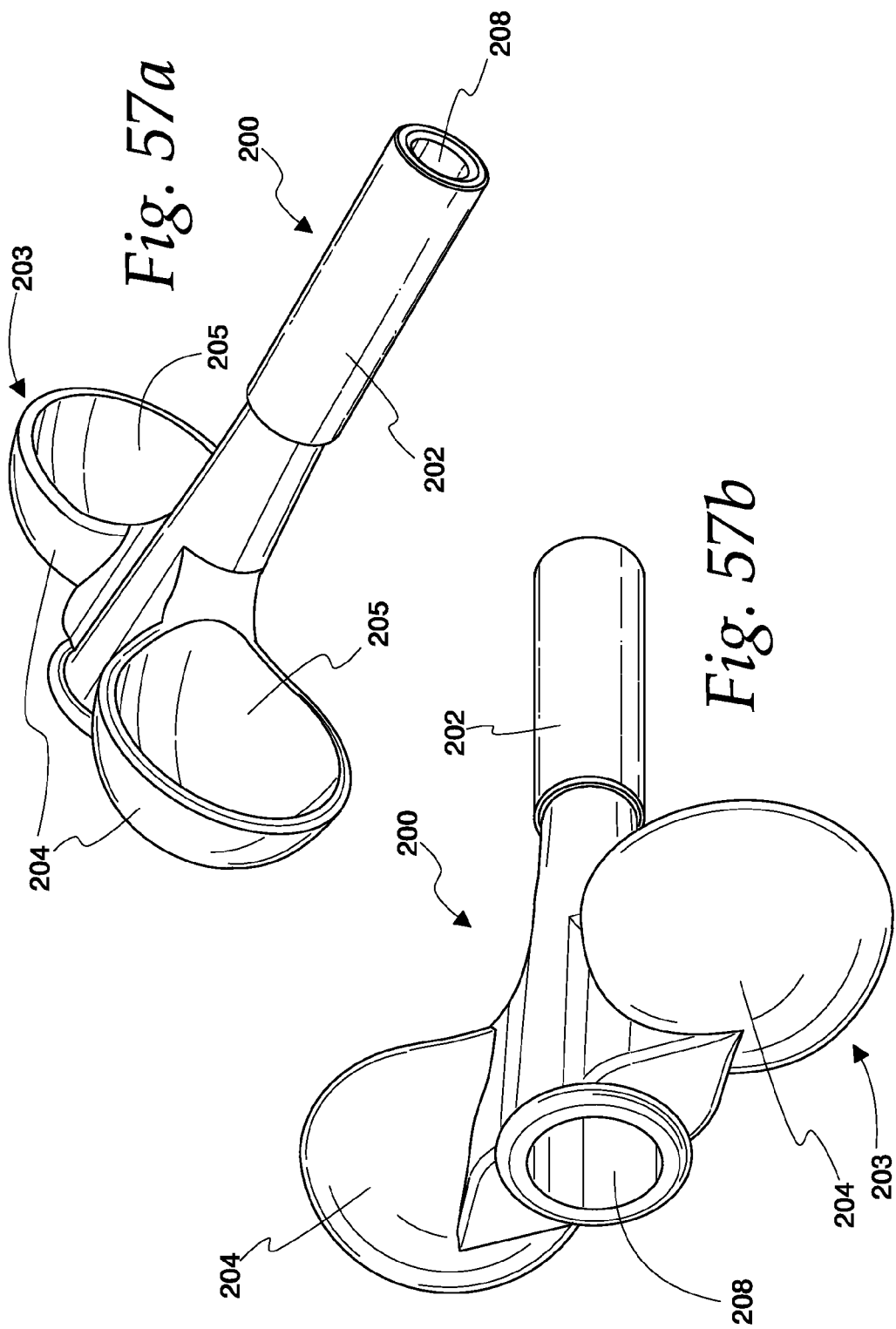

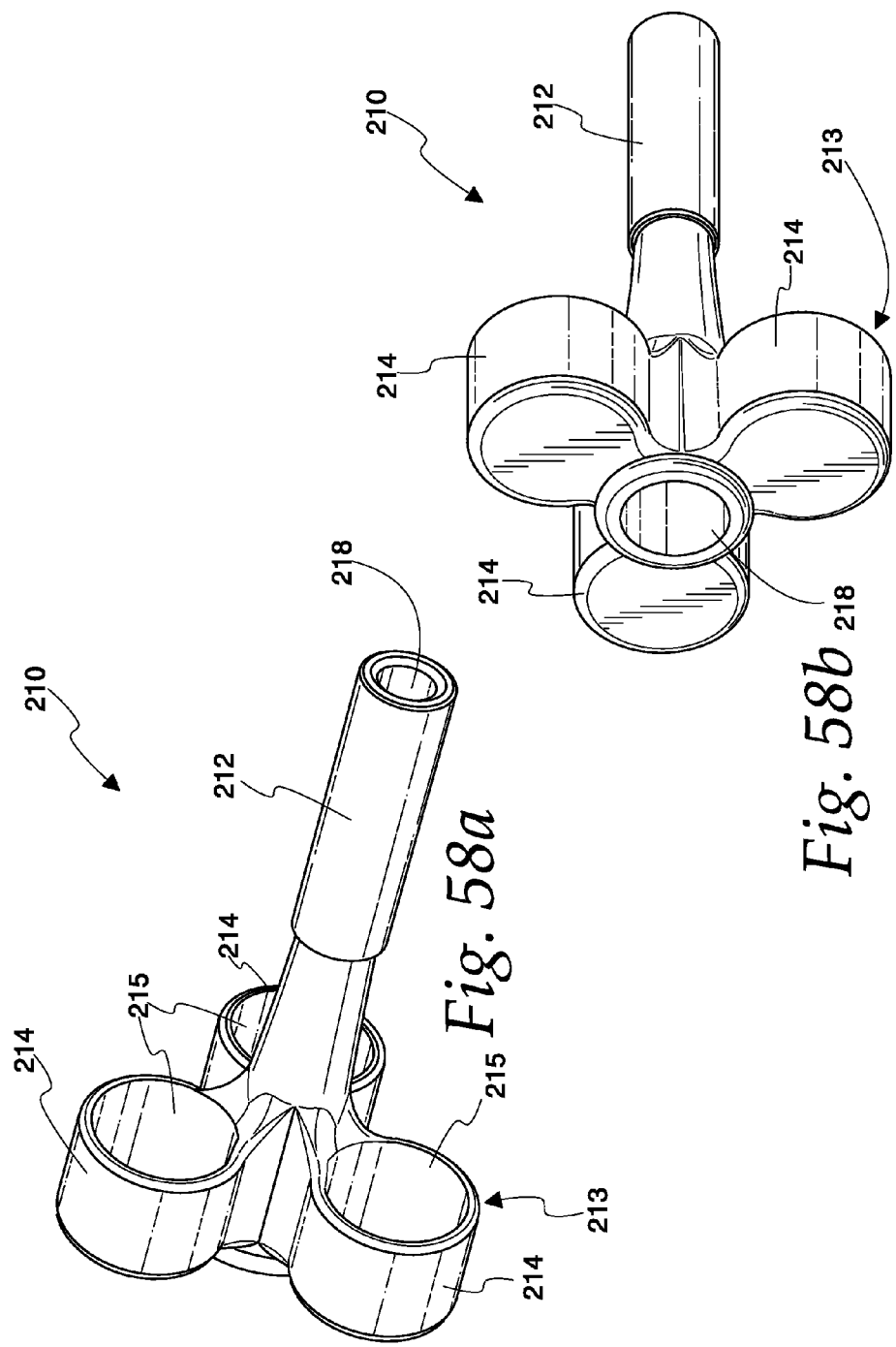

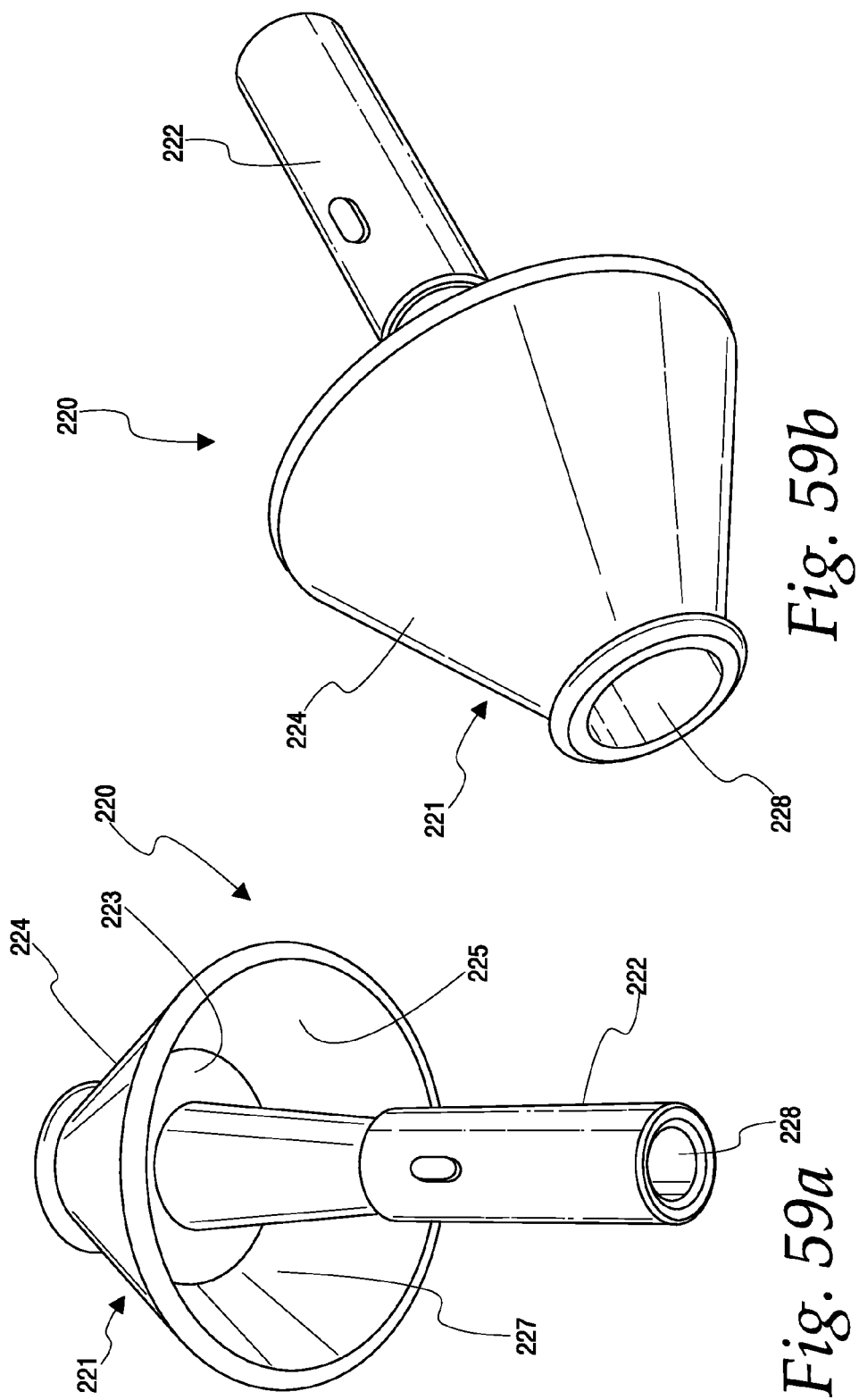

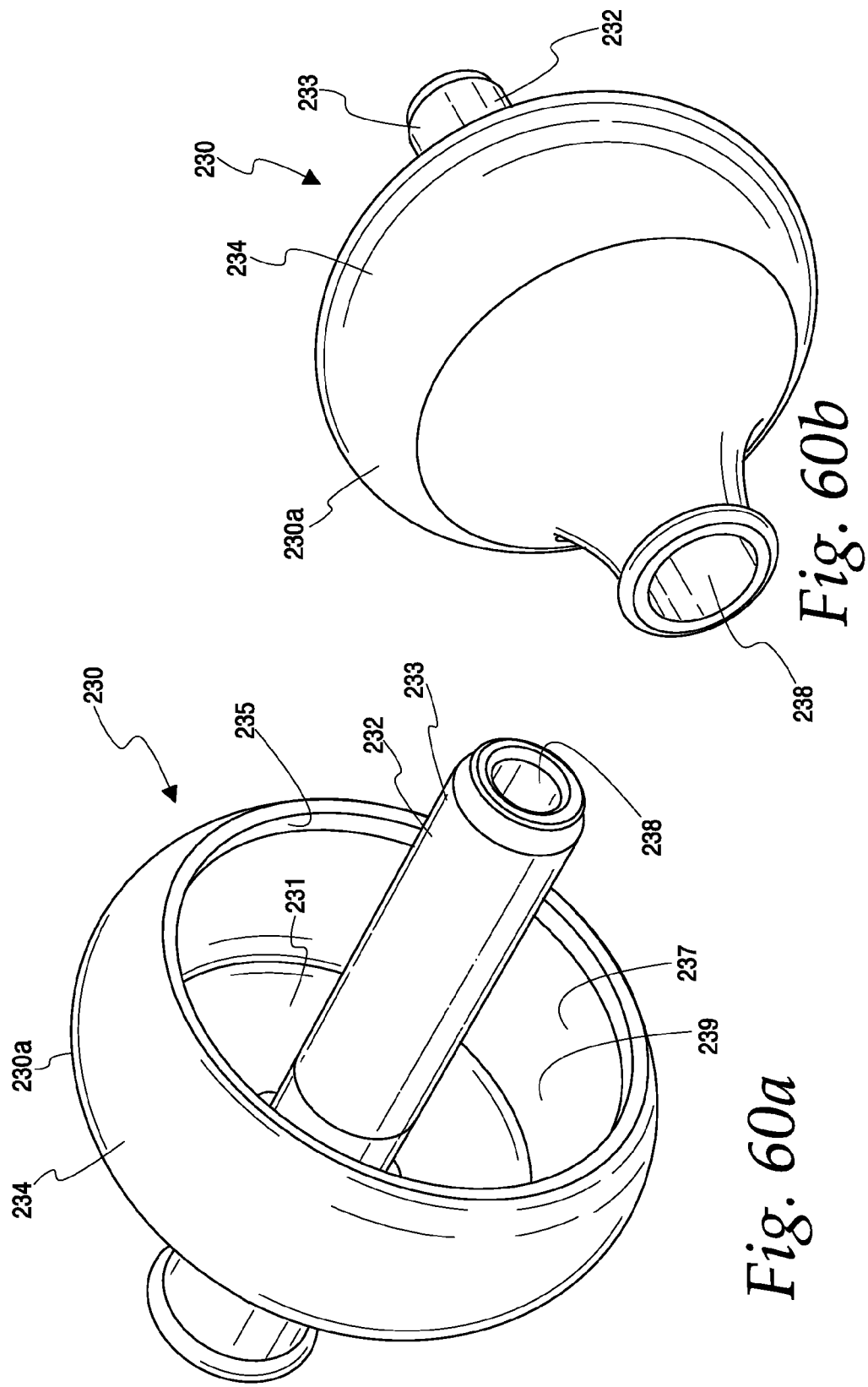

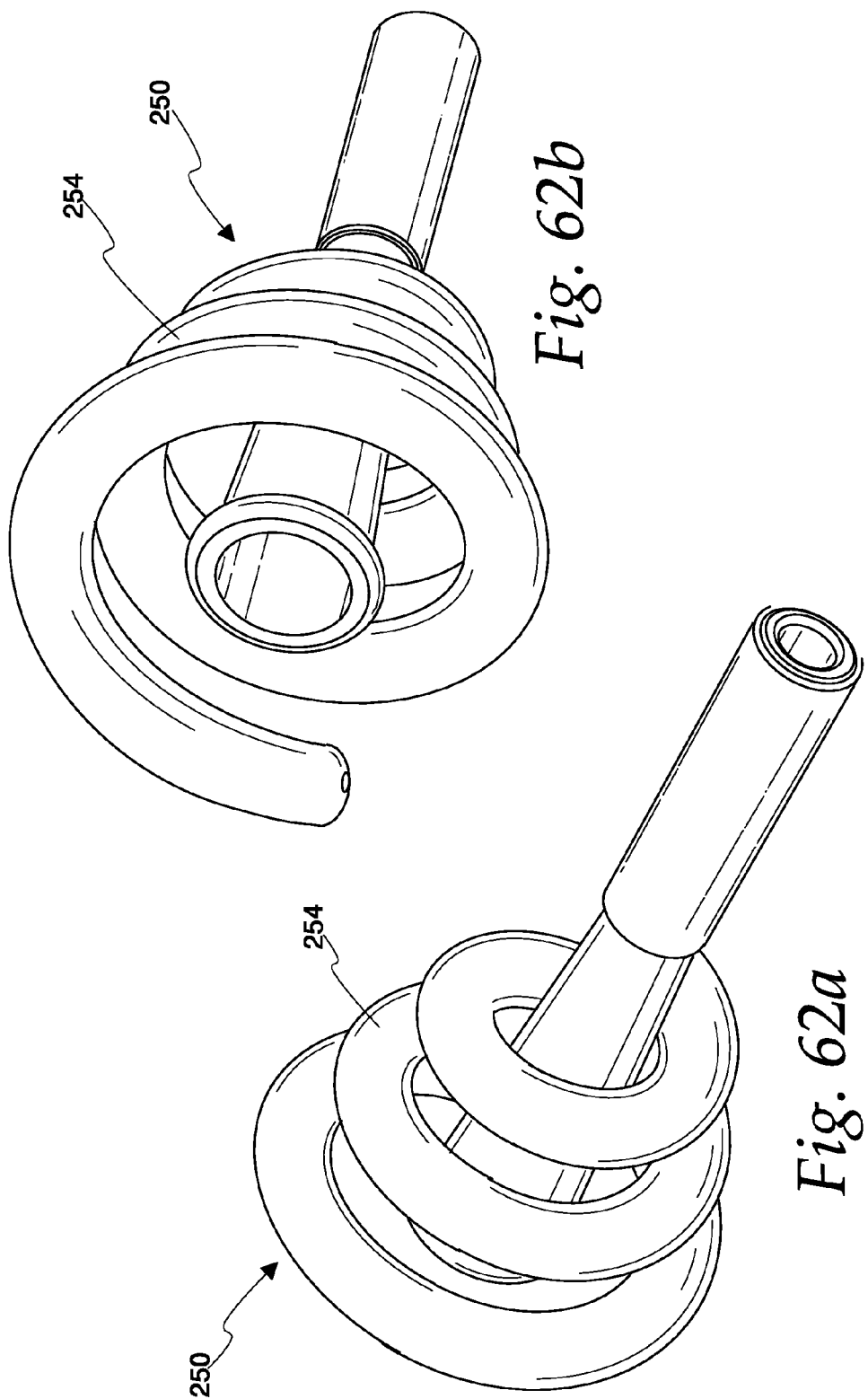

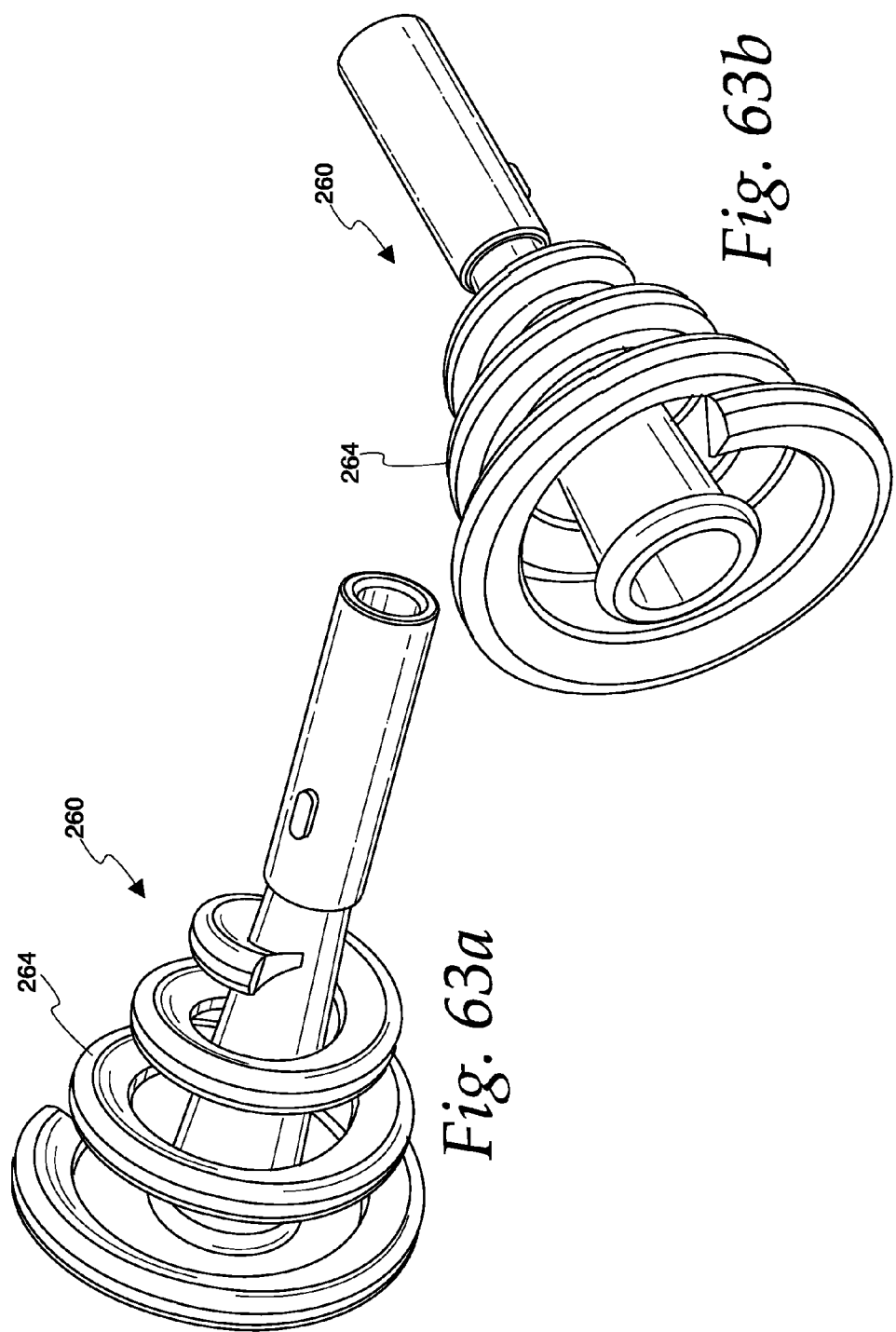

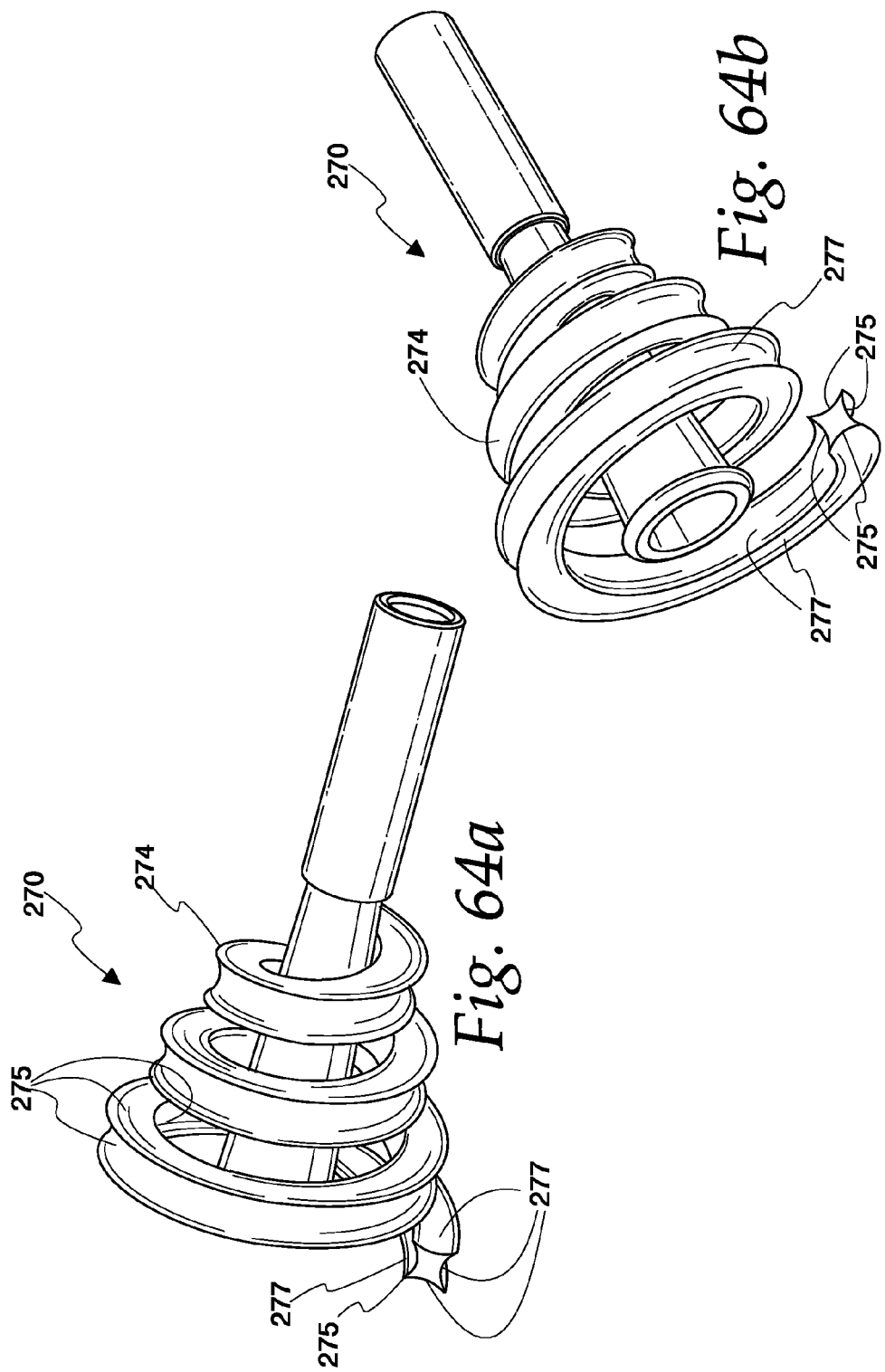

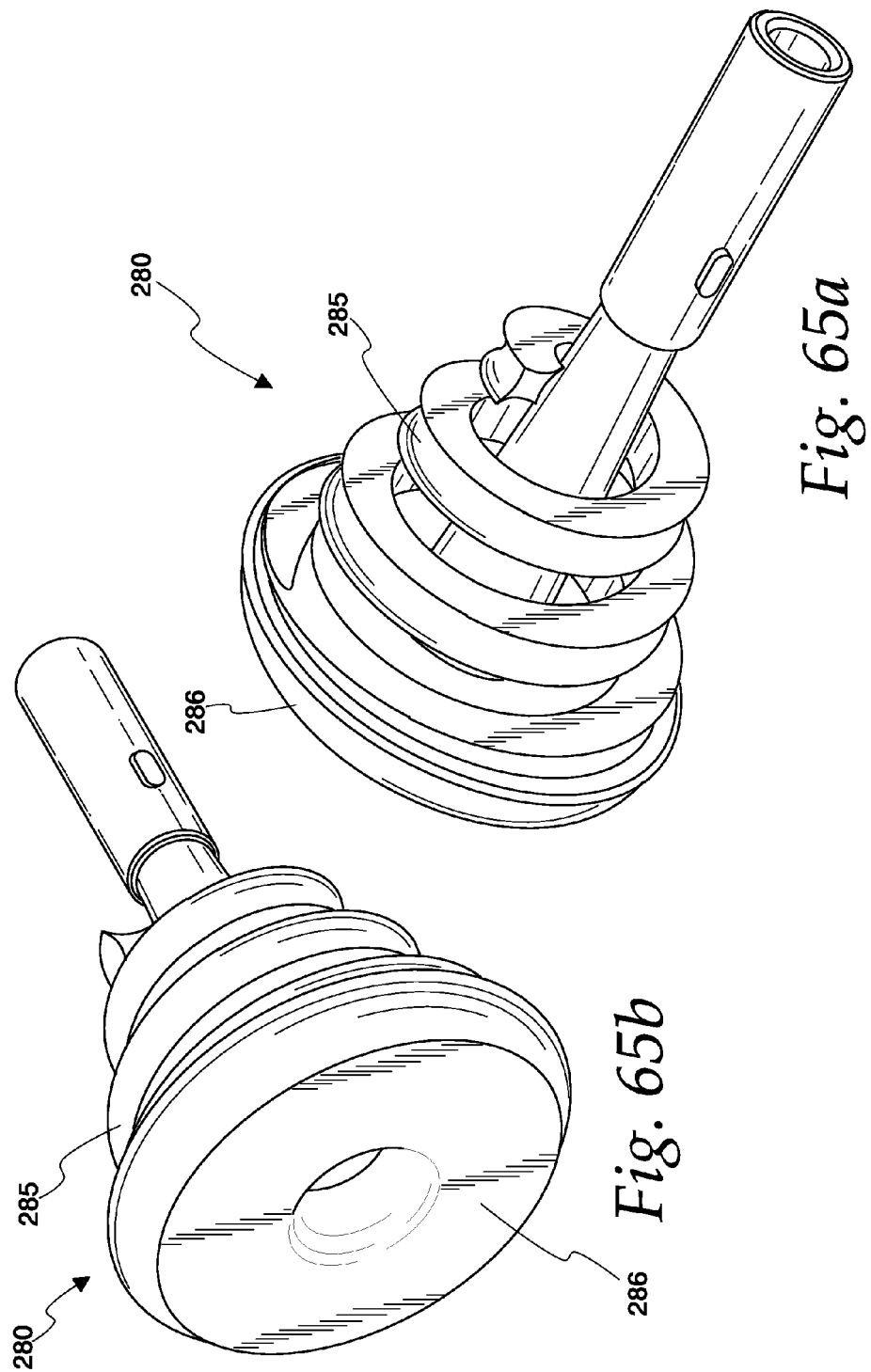

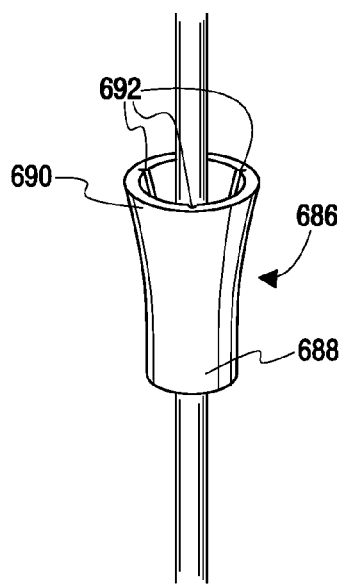
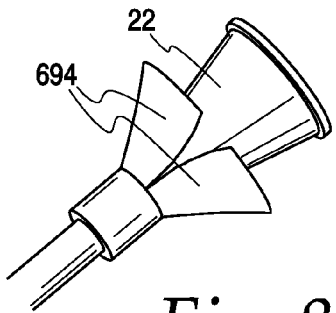
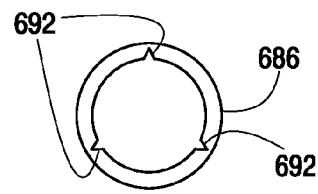
*Fig. 87*
*Fig. 89*
*Fig. 88*
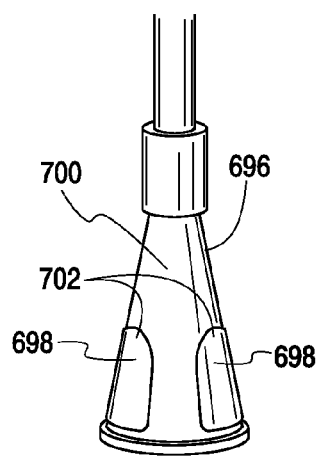
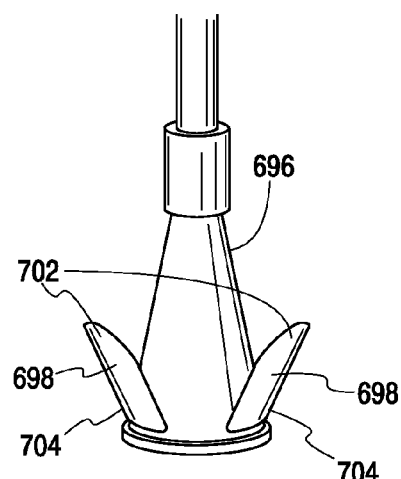
*Fig. 90*
*Fig. 91*

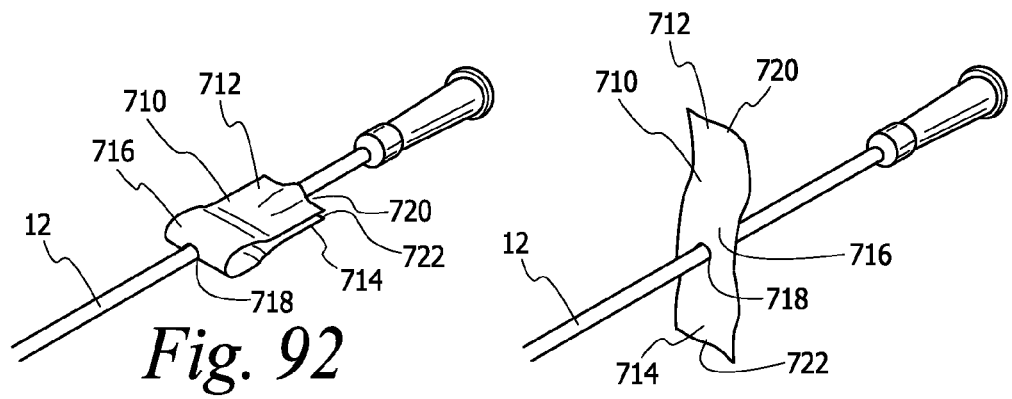
Fig. 92
Fig. 93
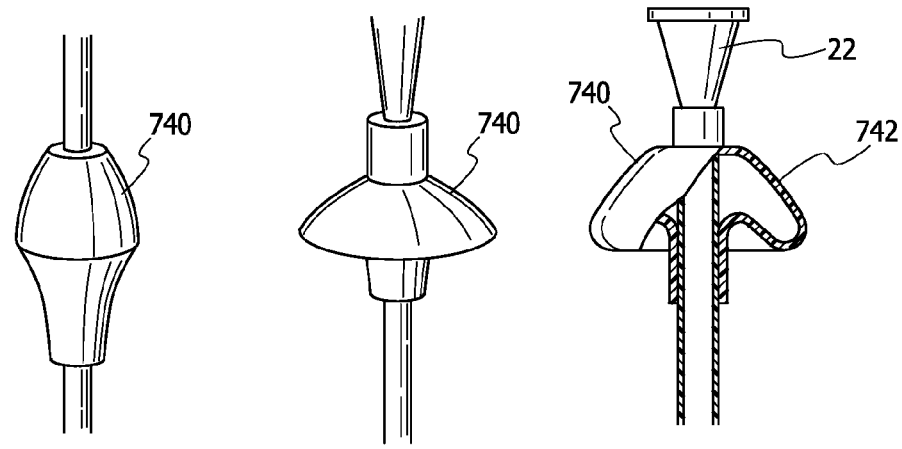
Fig. 94   Fig. 95   Fig. 96

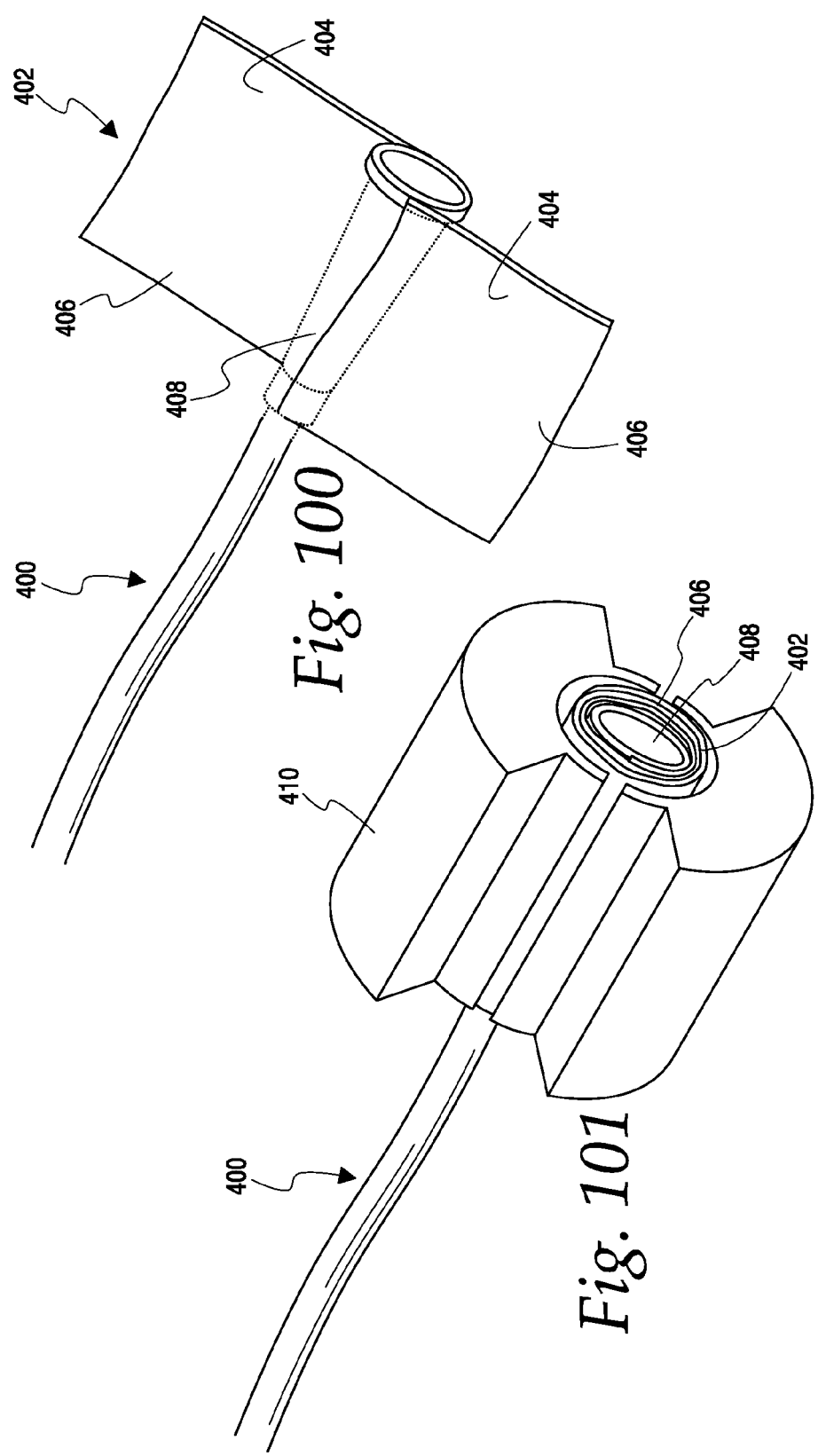

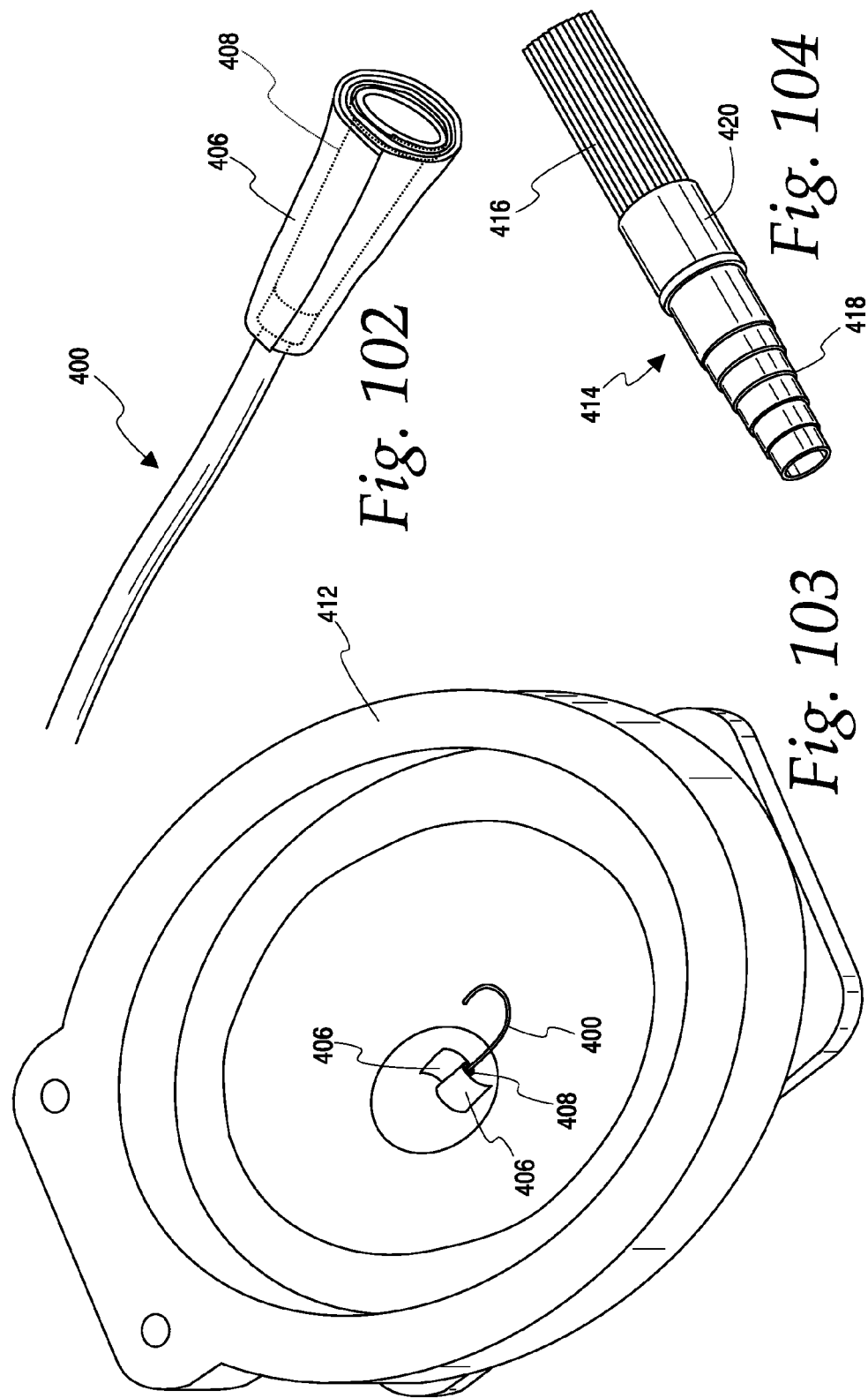

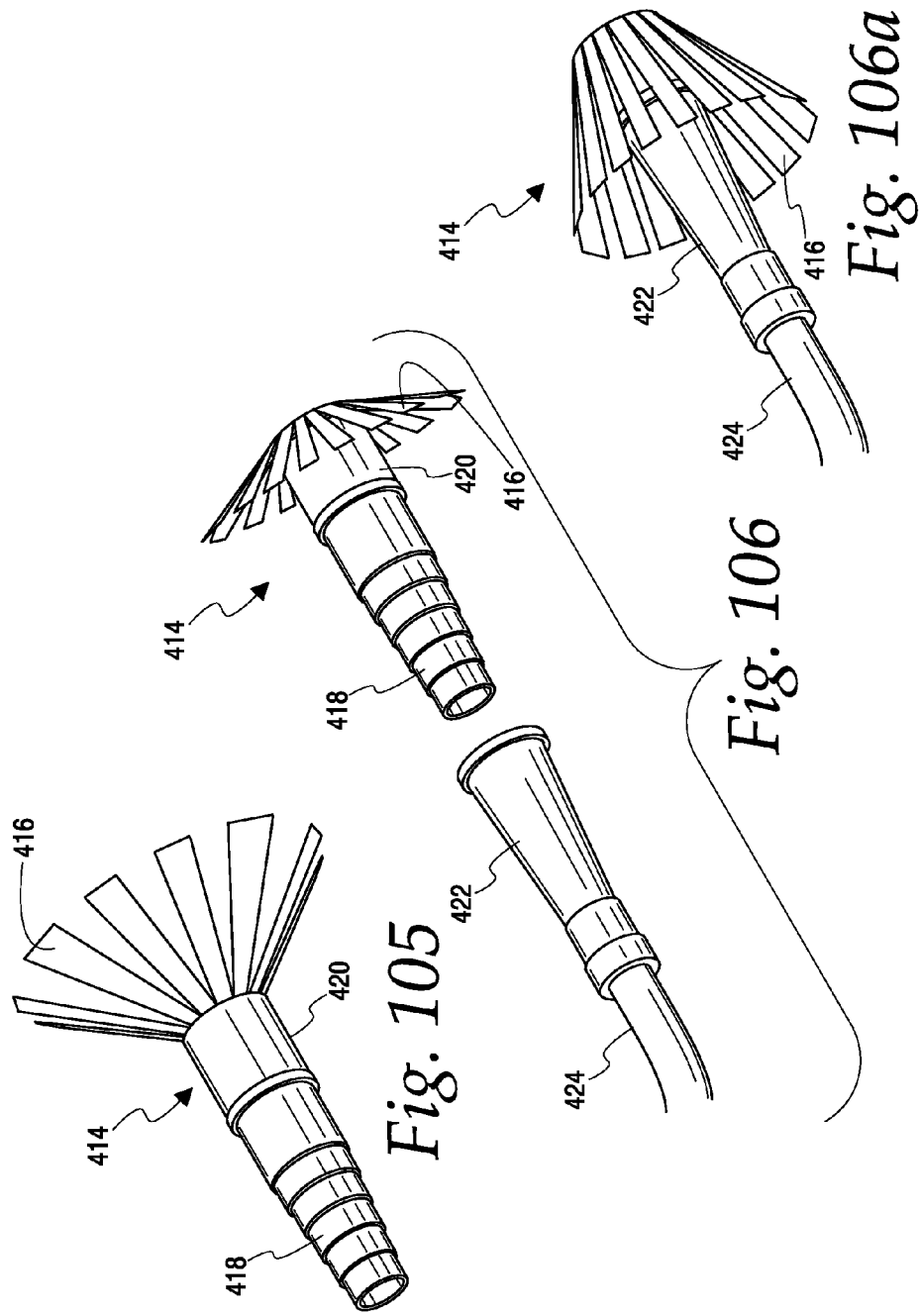

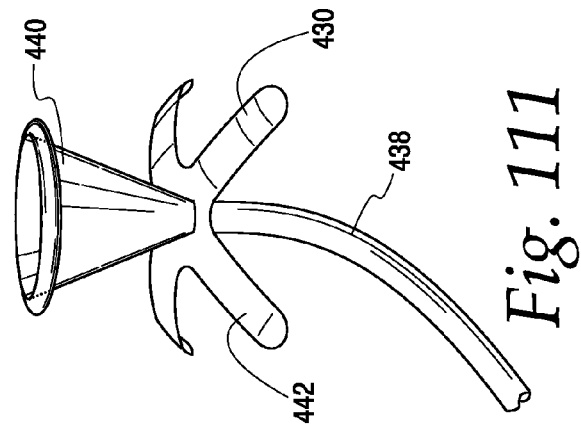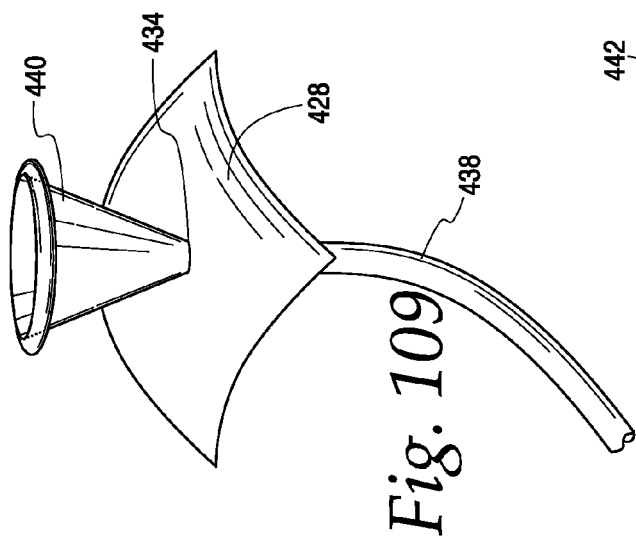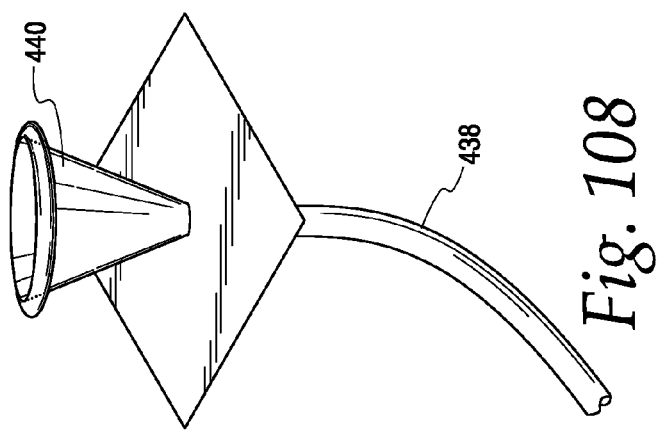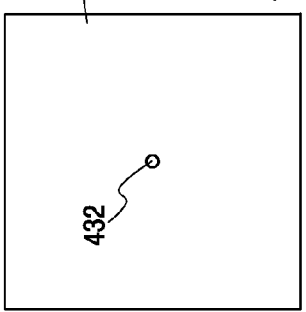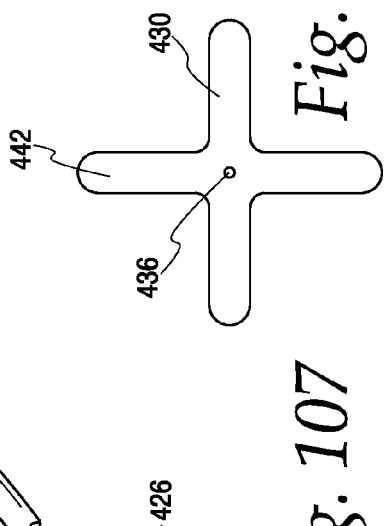

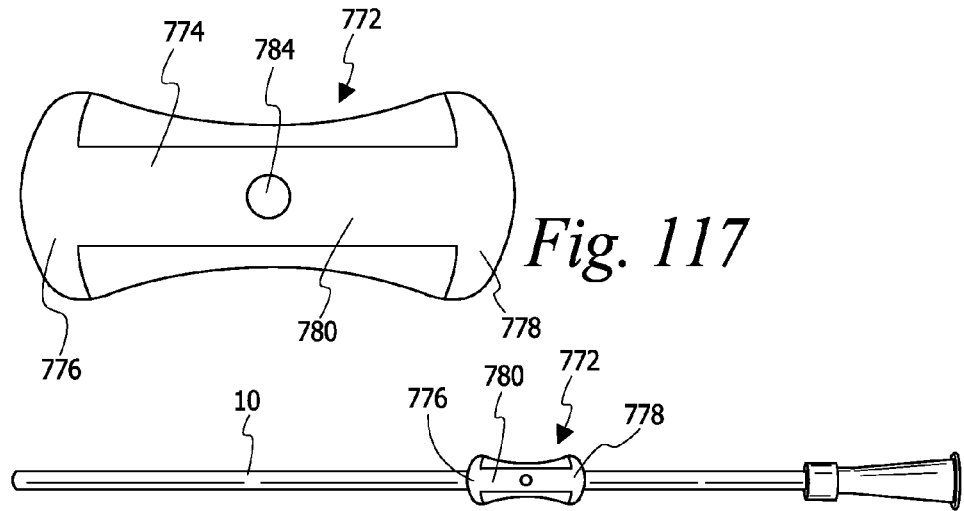
Fig. 117
Fig. 118
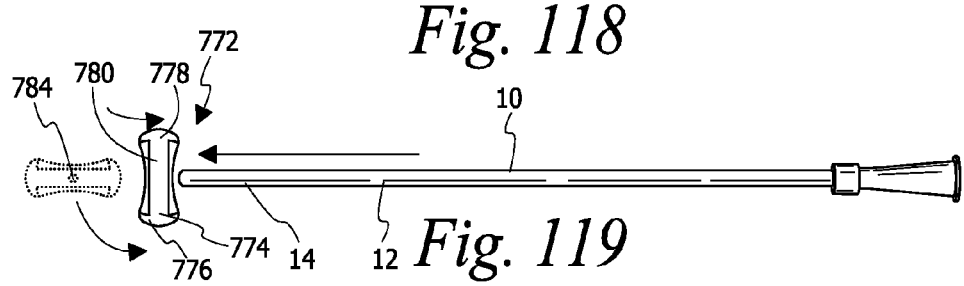
Fig. 119
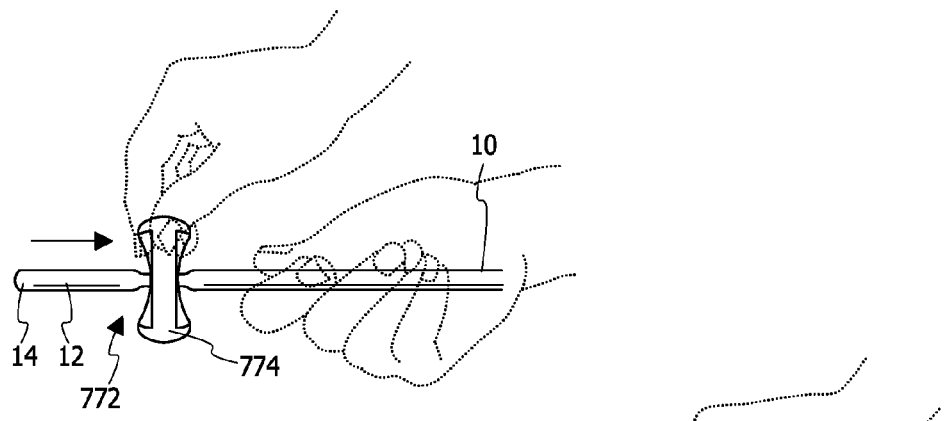
Fig. 120
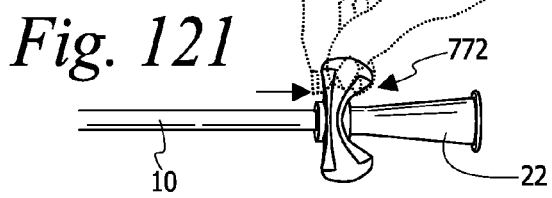
Fig. 121

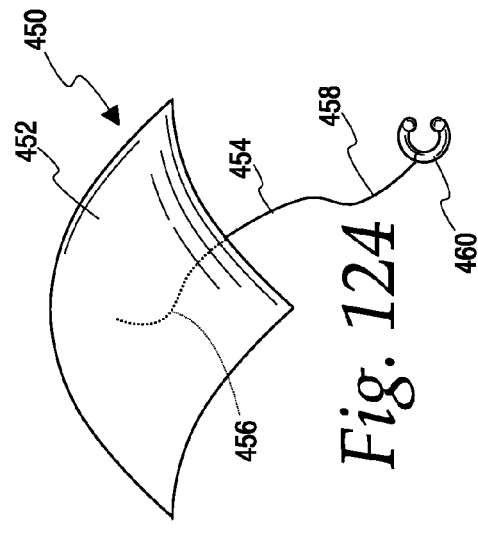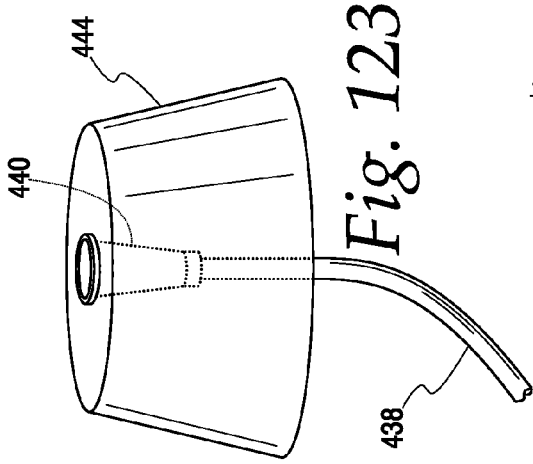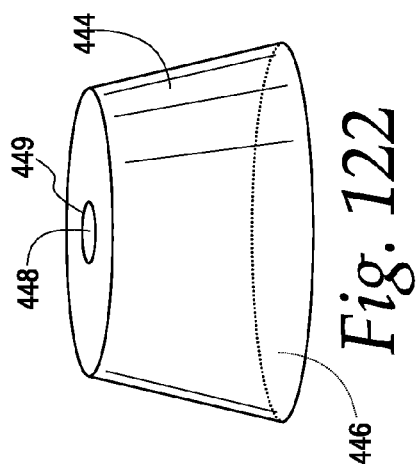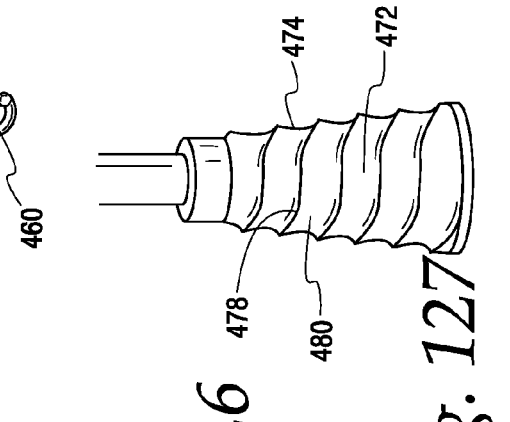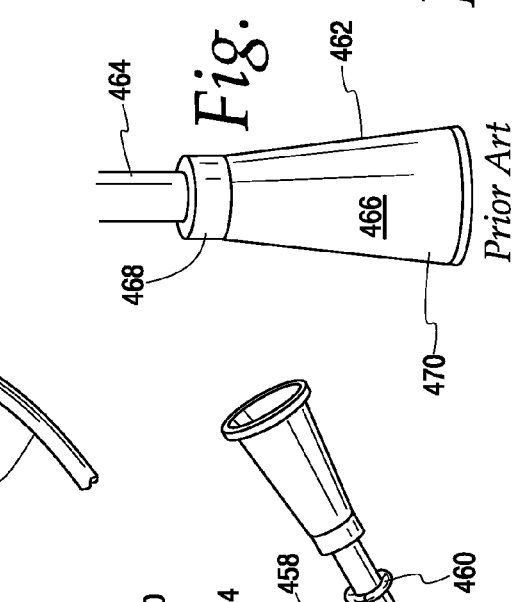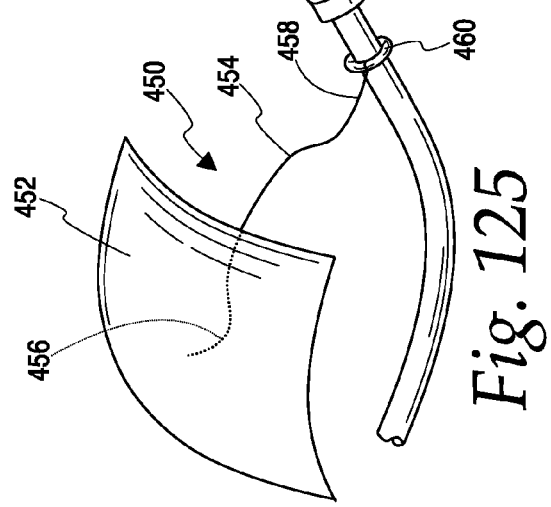

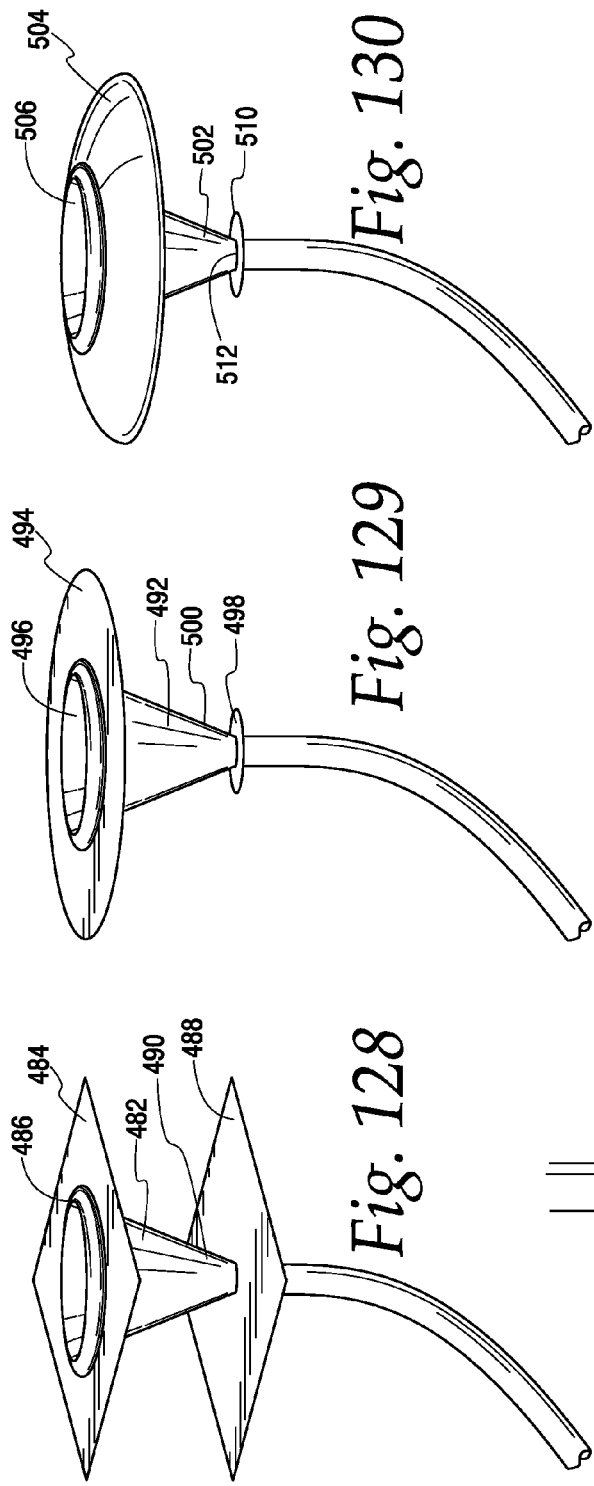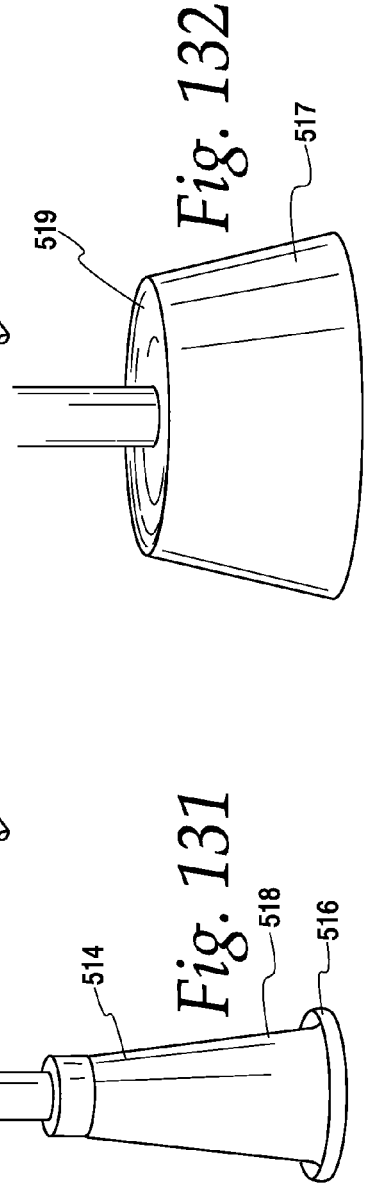

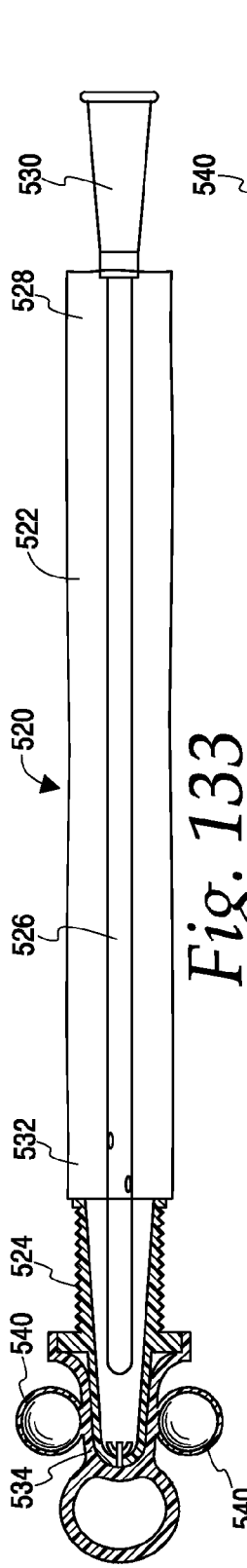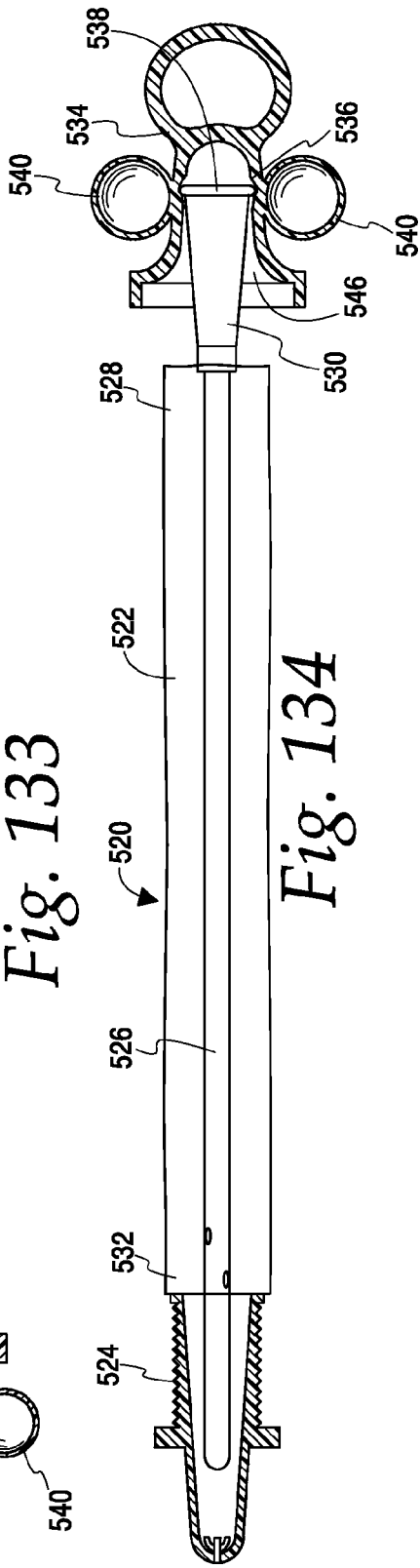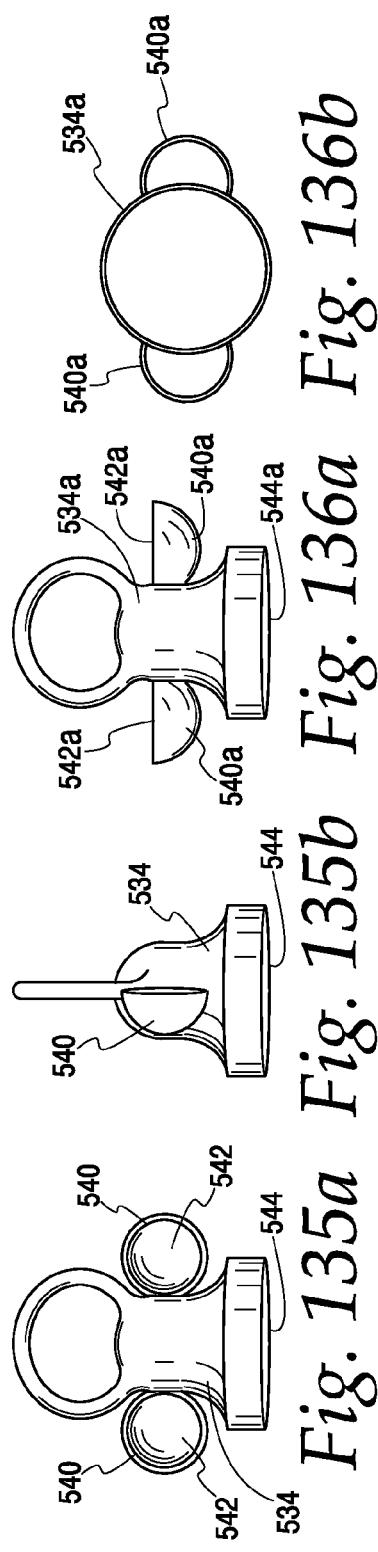

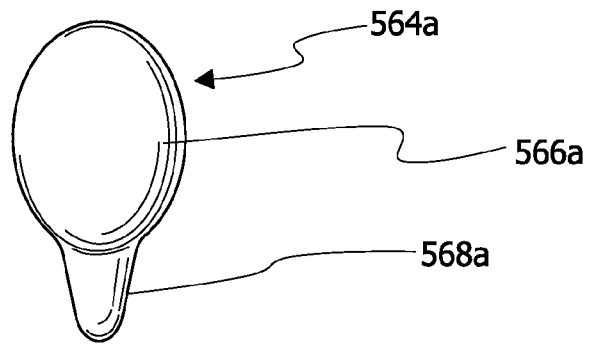
Fig. 143
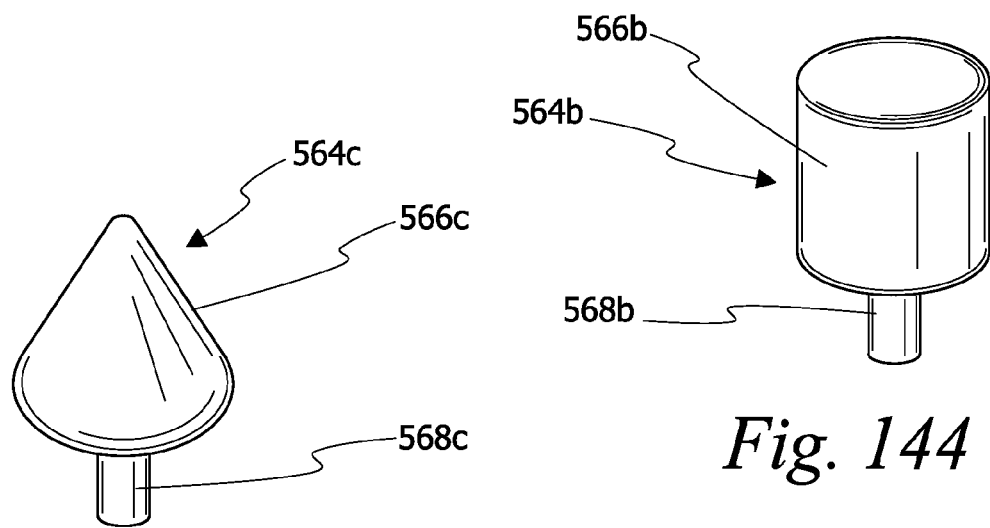
Fig. 144
Fig. 145
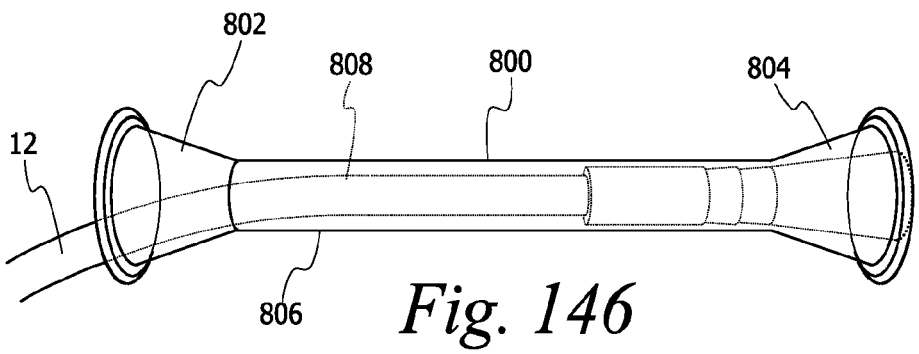
Fig. 146

FLUSHABLE CATHETERS

This application is the U.S. National Stage of PCT International Patent Application No. PCT/US2014/069556, filed Dec. 10, 2014, which claims the benefit of and priority to U.S. Provisional Patent Application Ser. No. 61/915,280, filed Dec. 12, 2013; U.S. Provisional Patent Application Ser. No. 61/915,270, filed Dec. 12, 2013; U.S. Provisional Patent Application Ser. No. 61/915,396, filed Dec. 12, 2013; U.S. Provisional Patent Application Ser. No. 62/011,204, filed Jun. 12, 2014; and U.S. Provisional Patent Application Ser. No. 62/011,266, filed Jun. 12, 2014, all of which are hereby incorporated herein by reference.

FIELD OF THE INVENTION

The present disclosure generally relates to urinary catheters that are configured to be disposed of by flushing down a toilet and, more particularly, to flushable catheters that structurally breakdown when contacted by water for convenient disposal down the toilet, and even more particularly related to catheters which are made from water disintegratable (e.g., water soluble, water degradable, or hydrolysable) materials and have characteristics configured to facilitate movement of the catheters down the toilet and/or through the sanitary system.

BACKGROUND OF THE INVENTION

Intermittent catheters are commonly used by those who suffer from various abnormalities of the urinary system, such as urinary incontinence. Such catheters typically include an elongated shaft that is inserted into and through the urethra to access the bladder. With the advent of intermittent catheters, individuals with urinary system abnormalities can self-insert and self-remove intermittent catheters several times a day. Such catheters typically include a shaft made from non-biodegradable polymeric materials, such as non-biodegradable thermoplastics. One drawback associated with such non-biodegradable catheters is that they typically, while intended for disposal, are not eco-friendly in that the non-biodegradable materials of the catheter may take several years to degrade.

Individuals who use intermittent catheters to drain their bladders several times a day often use such catheters at home and in public restrooms. Intermittent catheterization involves inserting the elongated shaft of the catheter through the urethra and into the bladder. Urine is drained from the bladder through the catheter and into a waste receptacle, such as a toilet or collection bag. After the bladder has been drained, the catheter is disposed of in a waste container. Oftentimes, especially in a public restroom, it is difficult to find a suitable waste container to dispose of the catheter, and if the individual has to carry the catheter some distance to a waste container, there may be some risk of leakage or spillage of bodily fluids. Additionally, the individual, especially in a public restroom, may be uncomfortable or embarrassed with carrying a used catheter to the waste container. In such situations, the individual may attempt to dispose of the catheter by flushing it down the toilet. For anatomical reasons, urinary catheters used by males are substantially longer than those used by females. An intermittent urinary catheter for an adult male can be as long as 40 cm. Flushing such catheters down the toilet can cause significant plumbing problems, such as clogging. Because the catheters are non-water disintegratable, flushing male or female urinary catheters down the toilet also raises environmental concerns.

More recently, there has been increasing interest in producing flushable catheters which are made from materials that structurally disintegrate when contacted with water, e.g., materials that are water dissolvable, water degradable and/or undergo hydrolysis in water. Such catheters are intended to be flushed down the toilet after use and dissolve, degrade or otherwise breakdown while passing through the sanitary system. Because flushable catheters are required to substantially maintain structural integrity during use (i.e., during insertion into the urethra, drainage of urine and removal from the urethra), the water disintegratable materials typically chosen are those with a slower degradation or dissolution rate and are such that the catheter does not substantially disintegrate until after being disposed of in the sanitary system for some time. Thus, when a flushable catheter is placed within the toilet for disposal, the structure of the catheter usually is still substantially intact and will remain substantially intact during flushing of the catheter for disposal thereof.

When a catheter is disposed of by flushing down a toilet, the force of the siphon and turbulent water current which occurs during flushing oftentimes does not carry or move the catheter down the toilet and into the pipes of the sewer system and the catheter remains in the toilet bowl after flushing. In such instances, the user may be required to flush the toilet multiple times or just leave the catheter in the toilet, which may be embarrassing, especially when using a public restroom.

The catheter may not flush down the toilet for any number of reasons. For example, if the catheter is too buoyant, it may float to the top of the toilet water which may make it difficult for the flushing water to carry the catheter down the toilet because, for example, the siphon and turbulent water forces may not be strong enough to overcome the buoyant forces. Conversely, if the catheter is not buoyant enough or too dense, the catheter may sink to the bottom of the toilet which also may make it difficult for flushing water to carrier the catheter down the toilet because, for example, the siphon and turbulent forces acting on the catheter may not be strong enough pull or propel the catheter out of the toilet bowl. Additionally, because of the geometry of a typical urinary catheter, the force or energy of the flushing water may not sufficiently impinge on the catheter to propel it down the toilet. This may be especially problematic with the now more common water conserving low flush or low flow toilets.

Thus, while flushable catheters will eventually disintegrate (e.g., dissolve, degrade or hydrolyse) after being placed within a toilet, it may be difficult to physically flush the catheter down the toilet for any number of reasons, which may result in the catheter remaining in the toilet bowl even after multiple flushes and ultimately embarrassment to the catheter user.

The present disclosure provides flushable urinary catheters that are configured to assist in movement of the catheter out of the toilet and through the sanitary system during flushing of the toilet.

SUMMARY OF INVENTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The catheters of the present disclosure include features and/or characteristics that assist or result in the catheter being flushed out of the toilet bowl and/or through the trapway/U-bend pipe (U-bend pipe) of the plumbing system. The catheters may have one or more of a tailored density, geometry, buoyancy and lubricity that assists in flushing the catheter down the toilet and/or through the U-bend pipe. The catheters may also include a flush enhancing element that may be integral with the catheters or attached to the catheters. The flush enhancing element may, for example, be a density modifying element and/or a water capture element.

One aspect of the present disclosure related to a flushable urinary catheter that includes a catheter shaft having a proximal insertion end portion and a distal end portion. The catheter includes a water capture element associated therewith. The water capture element is configured to receive the force of flushing water impinging on the one or more vanes of the water capture element so as to propel the catheter down the toilet.

The water capture element associated with the catheter may be integrally formed with the catheter or may be attached to the catheter prior to disposal thereof.

The water capture element, whether integrally formed with the catheter or attached thereto prior to disposal, may be of any suitable configuration. For example, the water capture element may include radially projecting members, bowl-shaped members, mushroom-shaped members, cup-shaped members, helical-shaped members, disc-shaped members, paddle-shaped members, bulbous-shaped members or any combination of the above.

Additionally, any of the water capture elements disclosed herein may be movable from a collapsed to an expanded position.

In another aspect, a flushable catheter includes a catheter shaft and one or more water capture vanes extending in a direction radially outwardly from the longitudinal axis of the catheter shaft. The one or more water capture vanes are configured to be contacted by flushing water to propel the catheter down the toilet. The catheter shaft and/or the one or more vanes are made of a water disintegratable material.

In another aspect, a flushable urinary catheter includes a catheter shaft having a proximal insertion end portion, a middle portion and a distal end portion. At least a portion of the catheter or an attachment to the catheter has material properties, such as a desired density, lubricity and/or surface free energy, that are selected to facilitate flushing of the catheter down the toilet and/or across a U-bend pipe. In one embodiment, the density of the catheter may be selected so that the catheter has a desired buoyancy level relative to water.

In one embodiment, the different portions of the catheter have different densities, lubricity, and/or surface free energies such that when the catheter is placed in toilet water, one portion of the catheter sinks to a desired water level and another portion of the catheter floats at a desired water level. For example, the proximal end portion of the catheter shaft may have a density, lubricity, and/or surface free energy that are different from at least one of the middle and distal end portions of the catheter shaft. Alternately, the middle portion of the catheter shaft may have a density, lubricity, and/or surface free energy that are different from at least one of the proximal and distal end portions of the catheter shaft. In yet another alternative, the distal end portion of the catheter may have a density, lubricity, and/or surface free energy that are different from at least one of the proximal end and middle portions of the catheter shaft.

In any of the embodiments, the density of the catheter may be graduated from one end of the catheter to the other.

In yet a further aspect, a flushable catheter that may be disposed of by flushing down the toilet includes a catheter shaft having a proximal insertion end portion and a distal end portion. The catheter also includes a drainage member associated with the distal end portion of the catheter shaft. The catheter shaft and/or the drainage member are made from a water disintegratable material and at least a section of the catheter has a density that results in self-orientation of the catheter when the catheter is placed in water.

These and other aspects of the present invention are set forth in the following detailed description. In that respect, it should be noted that the present invention includes a number of different aspects which may have utility alone and/or in combination with other aspects. Accordingly, the above summary is not an exhaustive identification of each such aspect that is now or may hereafter be claimed, but represents an overview of the present invention to assist in understanding the more detailed description that follows. The scope of the invention is as set forth in the claims now or hereafter filed.

BRIEF DESCRIPTION OF THE FIGURES

In the course of this description, reference will be made to the accompanying drawings, wherein:

FIG. 5 is a side view of another embodiment of a catheter of the present disclosure having a tailored or modified density schematically represented by stippling;

FIG. 6 is a side view of another embodiment of a catheter of the present disclosure having a tailored or modified density schematically represented by stippling;

FIG. 6a is a side view of another embodiment of a catheter of the present disclosure having a tailored or modified density schematically represented by stippling;

FIG. 7 is a side view of another embodiment of a catheter of the present disclosure having a tailored or modified density schematically represented by stippling;

FIG. 8 is a perspective view of any of the catheters of the present disclosure shown with the catheter in a compact configuration;

FIG. 9a is a top view of one embodiment of an elongate catheter package;

FIG. 9b is a perspective view of the package of FIG. 9a after opening and in a folded configuration for containing a spent catheter therein;

FIG. 10 is a partial top view of a catheter of the present disclosure having a securing element associated therewith;

FIG. 11 is a perspective view of a catheter of the present disclosure wherein a securing element holds the catheter in a compact configuration;

FIG. 12 is a perspective view of another embodiment of a catheter of the present disclosure with a securing element holding the catheter in a compact configuration;

FIG. 13 is a perspective view of one embodiment of a securing element for securing a catheter in a compact configuration;

FIG. 14 is a perspective view of a catheter secured in a compact configuration by the securing element of FIG. 13;

FIG. 15 is a perspective view of the catheter and securing element of FIG. 14 in a folded configuration.

FIG. 16 is a side view of a catheter of the present disclosure wherein the catheter includes an introducer tip and an outer protective sleeve;

FIG. 17 is a perspective view of the catheter of FIG. 16 shown in a knotted configuration and with the introducer tip attached to the funnel;

FIG. 18 is a perspective view of the catheter of FIG. 16 shown with the introducer tip attached to the funnel;

FIG. 19 is a perspective view of the catheter of FIG. 16 shown with the introducer tip attached to the funnel and the catheter secured in a compact configuration with a securing element;

FIG. 20 is a partial cross-section view of an introducer tip and a funnel of the present disclosure showing the attachment of the introducer tip to the funnel;

FIG. 21 is a partial cross-section view of other embodiments of an introducer tip and a funnel of the present disclosure showing the attachment between the introducer tip and funnel;

FIG. 22 is a perspective view of one embodiment of a funnel of the present disclosure including a securing element;

FIG. 23 is a perspective view of one embodiment of an introducer tip of the present disclosure including a securing element;

FIG. 24 is a perspective view of one embodiment of a catheter of the present disclosure including the funnel of FIG. 22 and introducer tip of FIG. 23 wherein the funnel and introducer tip are attached to the catheter to secure the catheter in a compact configuration;

FIG. 25 is a top plan view of a catheter within a disposal bag or pouch of the present disclosure wherein the disposal bag includes adhesive for maintaining the bag in a fold or compact configuration;

FIG. 26 is a perspective view of the disposal bag of FIG. 25 shown in a folded or compact configuration;

FIG. 27 is a perspective view of a catheter of the present disclosure shown being held in a bent or compact configuration by a securing element;

FIG. 28 is a perspective view of a catheter of the present disclosure shown being held in a bent or compact configuration by a securing element;

FIG. 41 is a cross-sectional view of one embodiment of the catheter gripping aid shown in FIG. 39;

FIG. 42 is a cross-sectional view of another embodiment of the catheter gripping aid shown in FIG. 39;

FIG. 43 is a side view of another embodiment of a catheter gripping aid of the present disclosure;

FIG. 44 is a top view of the catheter gripping aid of FIG. 43 shown with the activation member slid to one side;

FIG. 45 is a side view of an alternative design of the catheter gripping aid of FIG. 43;

FIG. 46 is a side view of the catheter gripping aid of FIG. 43 shown maintaining the catheter in a bent or compact configuration;

FIG. 49 is an end view of a catheter schematically showing the radial extending dimension which any of the water capture elements disclosed herein may optionally have relative to the radius of the catheter;

FIGS. 50*a* and 50*b* are perspective views of one embodiment of a water capture element of the present disclosure wherein the water capture element is associated with a drainage member;

FIGS. 51*a* and 51*b* are perspective views of another embodiment of a water capture element of the present disclosure;

FIGS. 52*a* and 52*b* are perspective views of another embodiment of a water capture element of the present disclosure;

FIGS. 53*a* and 53*b* are perspective views of another embodiment of a water capture element of the present disclosure;

FIGS. 54*a* and 54*b* are perspective views of another embodiment of a water capture element of the present disclosure;

FIGS. 55*a* and 55*b* are perspective views of another embodiment of a water capture element of the present disclosure;

FIGS. 56*a* and 56*b* are perspective views of another embodiment of a water capture element of the present disclosure;

FIGS. 57a and 57b are perspective views of another embodiment of a water capture element of the present disclosure;

FIGS. 58a and 58b are perspective views of another embodiment of a water capture element of the present disclosure;

FIGS. 59a and 59b are perspective views of another embodiment of a water capture element of the present disclosure;

FIGS. 60a and 60b are perspective views of another embodiment of a water capture element of the present disclosure;

FIGS. 62a and 62b are perspective views of another embodiment of a water capture element of the present disclosure;

FIGS. 63a and 63b are perspective views of another embodiment of a water capture element of the present disclosure;

FIGS. 64a and 64b are perspective views of another embodiment of a water capture element of the present disclosure;

FIGS. 65a and 65b are perspective views of another embodiment of a water capture element of the present disclosure;

FIG. 87 is a perspective view of another embodiment of a catheter gripping aid of the present disclosure;

FIG. 88 is a top view of the catheter gripping aid of FIG. 87;

FIG. 89 is a perspective view of the catheter gripping aid of FIG. 87 shown in an expanded configuration to define a water capture element;

FIG. 90 is a perspective view of a catheter funnel having a water capture element associated therewith wherein the water capture element is in a first or collapsed configuration;

FIG. 91 is a perspective view of the catheter funnel of FIG. 90 shown with the water capture element in a second or expanded configuration;

FIG. 92 is a perspective view of another embodiment of a catheter gripping aid of present disclosure shown mounted on a catheter;

FIG. 93 is a perspective view of the gripping aid of FIG. 92 shown in an expanded configuration to define a water capture element;

FIG. 94 is a perspective view of another embodiment of a catheter gripping aid of the present disclosure;

FIG. 95 is a perspective view of the catheter gripping aid of FIG. 94 shown in a second configuration that defines a water capture element;

FIG. 96 is a partial cross-sectional view of the catheter gripping aid of FIG. 95;

FIG. 100 is a perspective view of another embodiment of a water capture element of the present disclosure shown in association with a drainage member;

FIG. 101 is a perspective view of the water capture element of FIG. 100 shown within a mold;

FIG. 102 is a perspective view of the water capture element of FIG. 100 shown in a compact configuration;

FIG. 103 is a schematic view of the water capture element within a toilet and in an expended configuration;

FIG. 104 is a perspective view of another embodiment of a water capture element of the present disclosure shown in a collapsed configuration;

FIG. 105 is a perspective view of the water capture element FIG. 104 shown in an expanded configuration;

FIG. 106 is a perspective view of the water capture element of FIG. 104 shown being inserted into the drainage member of a catheter;

FIG. 106a is a perspective view of the water capture element of FIG. 104 shown inserted into the drainage member and in the expanded configuration;

FIG. 107 is a top view of another embodiment of a water capture element of the present disclosure;

FIG. 108 is a perspective view of the water capture element of FIG. 107 shown associated with a catheter;

FIG. 109 is a perspective view of another embodiment of a water capture element of the present disclosure associated with a catheter;

FIG. 110 is a top view of another embodiment of a water capture element of the present disclosure;

FIG. 111 is a perspective view of the water capture element of FIG. 110 shown in association with a catheter;

FIG. 112 is a bottom view of another embodiment of a catheter gripping aid of the present disclosure;

FIG. 113 is a top view of the catheter gripping aid of FIG. 112;

FIG. 114 is a perspective view of the catheter gripping aid of FIG. 112 shown mounted on a catheter;

FIGS. 115 and 116 are perspective views of the catheter gripping aid of FIG. 112 shown with the catheter gripping aid being oriented on the catheter to define a water capturing element;

FIG. 117 is a top view of another embodiment of a catheter gripping aid of the present disclosure;

FIG. 118 is a top view of the catheter gripping aid of FIG. 117 shown mounted on a catheter;

FIGS. 119-121 are side views of a catheter having the gripping aid repositioned on the catheter to define a water capture element;

FIG. 122 is a perspective view of another embodiment of a water capture element of the present disclosure;

FIG. 123 is a perspective view of the water capture element of FIG. 122 shown in association with a catheter;

Figure 139:
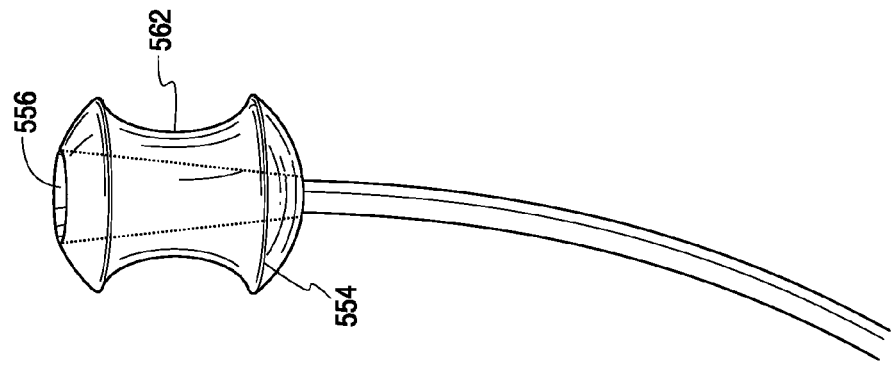
Figure 138:
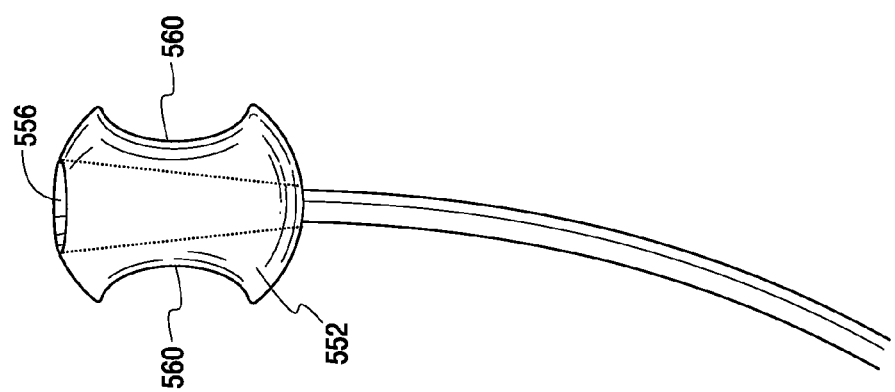
Figure 137:
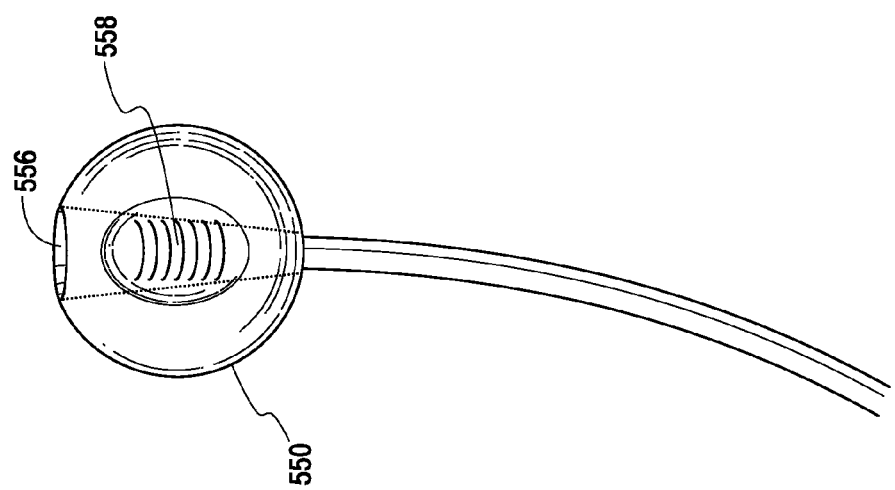
Figure 140:
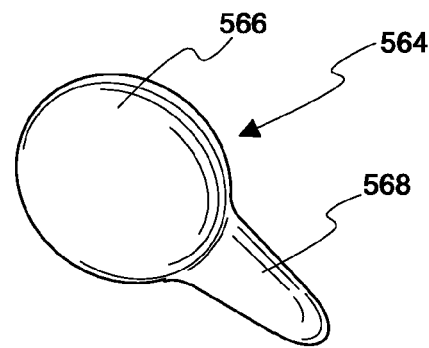
Figure 141:
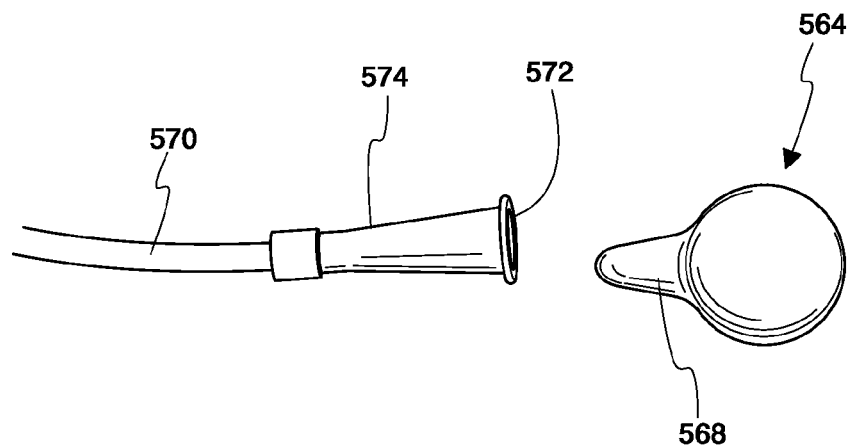
Figure 142:
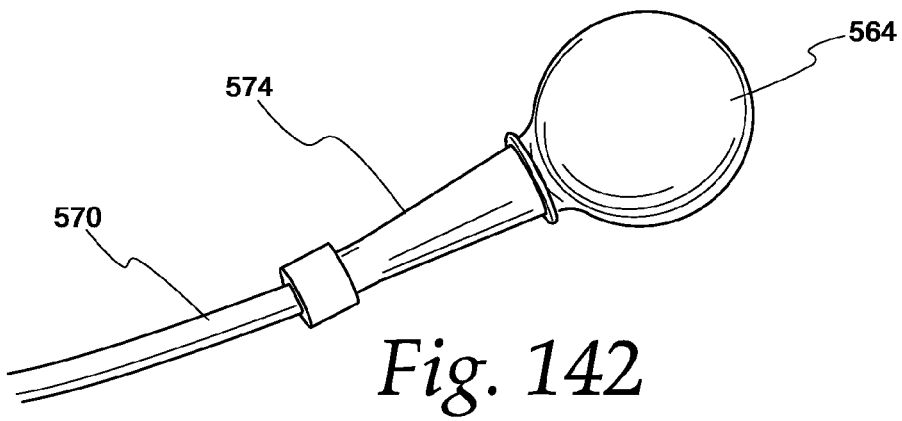

FIG. 124 is a perspective view of another embodiment of a water capture element of the present disclosure;

FIG. 125 is a perspective view of the water capture element of FIG. 124 shown in association with a catheter;

FIG. 126 is a perspective view of a known prior art funnel;

FIG. 127 is a perspective view of one embodiment of a drainage member of the present disclosure;

FIG. 128 is a perspective view of another embodiment of a drainage member of the present disclosure;

FIG. 129 is a perspective view of another embodiment of a drainage member of the present disclosure;

FIG. 130 is a perspective view of another embodiment of a drainage member of the present disclosure;

FIG. 131 is a perspective view of another embodiment of a drainage member of the present disclosure;

FIG. 132 is a perspective view of another embodiment of a drainage member of the present disclosure;

FIG. 133 is a side partial cross-sectional view of a catheter which includes another embodiment of a water capture element of the present disclosure shown associated with an introducer tip cap;

FIG. 134 is a side partial cross-section view of the catheter of FIG. 133 shown with the water capture element shown with the insertion tip cap associated with the funnel;

FIGS. 135a and 135b are perspective views of the introducer tip cap having the water capture element associated therewith;

FIGS. 136a and 136b are perspective views of another embodiment of cap having a water capture element associated therewith;

FIGS. 137-139 are perspective views of further embodiments of drainage members of the present disclosure;

FIG. 140 is a perspective of another embodiment of a water capture element of the present disclosure;

FIGS. 141 and 142 are perspective views of the water capture element FIG. 140 shown being attached to a drainage member a catheter;

FIGS. 143-145 are perspective view of various embodiments of water capture element that may be used in conjunction with a flushable catheter; and FIG. 146 is a perspective view of another embodiment of a catheter gripping aid of the present disclosure.

DETAILED DESCRIPTION

When a catheter is placed in a toilet bowl for disposal and the toilet is flushed, there are several forces acting on the catheter, including but not limited to, turbulent water, siphoning, buoyancy, and adhesion/attraction to the inner surface of the toilet bowl. The forces of the turbulent water and siphoning through the U-bend pipe are examples of flushing or drag forces that can act upon the catheter to urge the catheter to exit the drain of the toilet bowl. Other forces, such buoyancy and adhesion/attraction to the inner sidewalls of the toilet bowl, for example, tend to urge the catheter to remain within the toilet bowl. When the amount of the flushing forces acting on the catheter are greater than the forces tending to keep the catheter within the toilet bowl (e.g., buoyancy, resistance, and/or adhesion forces) the catheter in most instances will be propelled down the toilet and across the U-bend pipe.

The catheters disclosed herein include features and/or characteristics that may increase the amount of the flushing forces (e.g., flushing water and siphoning) acting on the catheter and/or reduce the amount of forces tending to keep the catheter within the toilet (e.g. buoyancy and/or adhesion forces). For example, the density and/or geometry of the catheter may be tailored to optimize or increase the amount of the flushing force acting on the catheter. Alternatively or in addition to optimizing/increasing the flushing force, the density and/or geometry of the catheter may be tailored to optimize the buoyancy of the catheter so that the catheter will flush down the toilet under the flushing forces (e.g. momentum of flushing water). In one embodiment, for example, the density and/or geometry may be tailored to increase the amount of flushing forces acting on the catheter and to reduce the amount of the catheter's buoyancy so that the catheter flushes down the toilet. In this and other embodiments, the catheter also may include a lubricious outer surface that is tailored to reduce the catheter's adhesion, if adhesion occurs, to the walls of the toilet and to help the catheter slide along the surface of the toilet. In other words, the lubricious outer surface may reduce resistance caused by contact between the catheter and the inner wall of the toilet.

Figure 1:
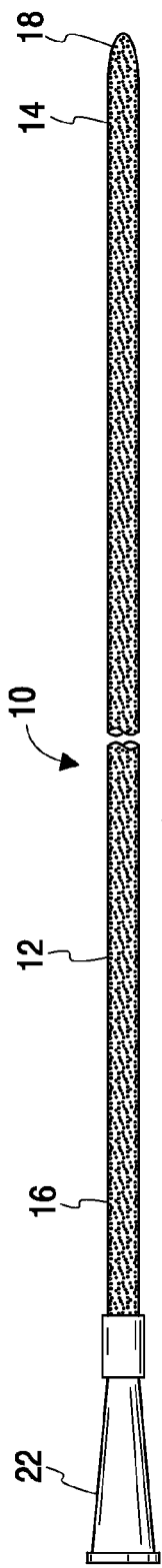
FIG. 1 is a side view of one embodiment of a catheter of the present disclosure having a tailored or modified density schematically represented by stippling.

Referring to FIG. 1, catheter 10 includes an elongated shaft 12 having a proximal insertion end portion 14 and a distal end portion 16. Proximal insertion end portion 14 includes a proximal end insertion tip 18 that is suitable for insertion into a lumen or a passageway of the body, such as the urethra. Proximal end insertion tip 18 includes draining holes or eyes (not shown) for the drainage of bodily fluids therethrough and into an internal conduit or lumen (not shown) of shaft 12. Distal end portion 16 may include a drainage member 22, such as a funnel, associated therewith for fluidly connecting the flow path of catheter 12 to a collection container, such as a collection bag, or directing urine into a collection receptacle, such as a toilet. In one embodiment, the collection bag may be flushable and may be made from any suitable flushable material, including those disclosed herein.

Catheter 10 and all of the other catheters disclosed herein are preferably, but not necessarily, catheters that structurally breakdown when contacted by water for convenient disposal down the toilet and through the sewer system. The catheters disclosed herein may be made from one or more materials that are affected by a fluid (for example, water, urine or fluids utilized in toilet and plumbing systems). Such materials may be water disintegratable or disintegrable materials. As used herein "water disintegratable" or "water disintegrable" materials refers to materials that are water soluble, water degradable, or water hydrolysable, and which dissolve, degrade, or otherwise breakdown when in contact with water over a selected period of time. In other embodiments, the material may be enzymatically hydrolysable. The water disintegratable and enzymatically hydrolysable materials are preferably flushable materials which are suitable for disposal in a toilet or sanitary system and, even more preferably, biodegradable flushable materials which may be chemically broken down by living organisms or other biological means.

Such water disintegratable or enzymatically hydrolysable materials may include, for example, polyvinyl alcohol, including but not limited to an extrudable polyvinyl alcohol, polyacrylic acids, polylactic acid, polyesters, polyglycolide, polyglycolic acid, poly lactic-co-glycolic acid, polylactide, amines, polyacrylamides, poly(N-(2-Hydroxypropyl) methacrylamide), starch, modified starches or derivatives, amylopectin, pectin, xanthan, scleroglucan, dextrin, chitosans, chitins, agar, alginate, carrageenans, laminarin, saccharides, polysaccharides, sucrose, polyethylene oxide, polypropylene oxide, acrylics, polyacrylic acid blends, poly(methacrylic acid), polystyrene sulfonate, polyethylene sulfonate, lignin sulfonate, polymethacrylamides, copolymers of aminoalkyl-acrylamides and methacrylamides, melamine-formaldehyde copolymers, vinyl alcohol copolymers, cellulose ethers, poly-ethers, polyethylene oxide, blends of polyethylene-polypropylene glycol, carboxymethyl cellulose, guar gum, locust bean gum, hydroxypropyl cellulose, vinylpyrrolidone polymers and copolymers, polyvinyl pyrrolidone-ethylene-vinyl acetate, polyvinyl pyrrolidone-carboxymethyl cellulose, carboxymethyl cellulose shellac, copolymers of vinylpyrrolidone with vinyl acetate, hydroxyethyl cellulose, gelatin, poly-caprolactone, poly(p-dioxanone), or combinations, blends or co-polymers of any of the above materials. The water disintegratable materials may also be any of those that are included in certified flushable products that meet the National Sanitation Foundation standards for flushability or materials and products that meet INDA/EDANA Flushability Guidelines or the UK Water Industry Research test protocols set forth in "Test Protocol to Determine the Flushability of Disposable Products, Review of the Manufactures $3^{rd}$ Ed. Guidance Document," 2013, by Drinkwater et al. While catheters made from water disintegratable materials may be disposed of in a toilet, it is not necessary to dispose of such catheters in a toilet and such catheters may also be disposed in normal municipal waste systems or garbage collection systems.

The catheters disclosed herein also may be lubricated with any suitable lubricant. For example, the catheters may be lubricated with a lubricant that does not substantially dissolve or degrade the catheter during use. In one embodiment, the lubricant may include a non-aqueous lubricant or a mixture of a non-aqueous lubricant and an amount of water. In such an embodiment, the mixture may include less than 20 wt % of water. In other embodiments, the mixture may include less than 15 wt %, 10 wt % or 5 wt % of water. In yet other embodiments, the mixture may include between about 20 wt %-0 wt % of water and preferably between about 5 wt %-0 wt % of water. Such non-aqueous lubricants that may be used alone or in a mixture containing water include, but are not limited to, polyethylene glycol, propylene glycol, glycerol, hydrophilic coatings or an oleophilic substance, such as an oleated glycerol (glycerol mono, di, tri or mixed oleates), oleyl alcohol, oleic acid, and mixtures thereof. Such lubricants may be applied during manufacturing and packaging of the catheter or may be applied just before use by, for example, the user.

When the lubricant is applied during manufacture and packaging, the lubricated flushable catheter (which may be made from any of the flushable materials disclosed herein) made be sterilized within the package by any suitable sterilization methods. For example, the lubricated flushable catheter may be sterilized with irradiation, such gamma or e-beam irradiation. In other embodiments, the catheter may be sterilized by ethylene oxide and/or by heat sterilization.

While the lubricity of the catheter eases insertion into the urethra, the lubricity may also be tailored or selected to enhance the flushability of the catheter. For example, the lubricant or the degree of lubricity may be tailored to prevent or reduce sticking to the side of the toilet and/or the pipes and U-bend pipe of the sewer system.

The density of any of the catheters disclosed herein may be tailored or modified, including but not limited to selecting a desired density for the catheter and/or a particular portion(s) of the catheter and/or graduating the density along the catheter. In one example, the density of the catheter may be tailored to optimise its flushability. In one embodiment of the present disclosure, the density of the catheter may be tailored to result in a desired buoyancy of the catheter when the catheter is placed within water, i.e., toilet water. In another embodiment, the density and the geometry of the catheter may be tailored to result in a desired buoyancy of the catheter.

The density alone and/or the geometry of the catheter may be tailored such that the catheter will move into a desired orientation when placed within water, i.e. self-orient within water. It will be understood that the density of the catheter may be tailored so that the catheter has both features of a desired buoyancy and will move into a desired orientation when placed within water.

Referring back FIG. 1, in this embodiment, the density of the catheter 10 has been tailored along the entire length of the catheter so that the catheter has a density that produces a desired catheter buoyancy relative to water and preferably a buoyancy that is conducive to the catheter 10 being carried down the toilet and/or through the pipes of the sewer system by forces generated by flushing the toilet water.

The tailored or modified density of the catheters shown in FIGS. 1-7 is schematically represented by stippling regardless of how the density is tailored/modified (e.g., different sections made from different materials, additives, mixtures of material, etc.). Additionally, the degree of stippling is employed to represent the level of density of the different sections of the catheter relative to other sections of the catheter. That is, denser stippling represents a denser section, less dense stippling represents a less dense section and graduated stippling represents a graduated density along the catheter or a portion of the catheter.

In FIG. 2-7, the density of each of the illustrated catheters is tailored so that one portion of the catheter has a different density (e.g., is denser or less dense) than other portions of the catheter. Tailoring the densities of the different catheter portions may be done for the purposes of optimising the buoyancy of the catheter to enhance flushability and/or to cause the catheter to move into a desired orientation when the catheter is placed within the water of a toilet bowl, i.e., the differing densities between the catheter portions may result in the catheter self-orienting within the toilet water. For example, the catheter may be so constructed such that one or more portions of the catheter have a greater density than one or more other portions of the catheter. The densities of the different portions of the catheter can be so modified or tailored so that when the catheter is placed within water, the denser portion(s) of the catheter will sit at a lower level in the toilet water than the less dense portion(s). In other words, when the catheter is placed within the toilet water, the denser portion(s) sinks to a lower level in the water and the less dense portion(s) rises or remain at a higher level, thereby resulting in the catheter self-orientating itself into a desired orientation within the toilet water.

In another embodiment, the density and/or geometry are tailored so that one portion of the catheter is less buoyant than another portion of the catheter and so that the less buoyant portion sinks within the toilet while the more buoyant portion floats. It should be understood that the amount of buoyancy of the catheter or portions thereof may be affected by both the density and geometry of the catheter or catheter portion. Because of this, it may be possible to have a denser portion of the catheter that has a geometry that results in the portion being more buoyant than a less dense portion of the catheter.

Figure 2:
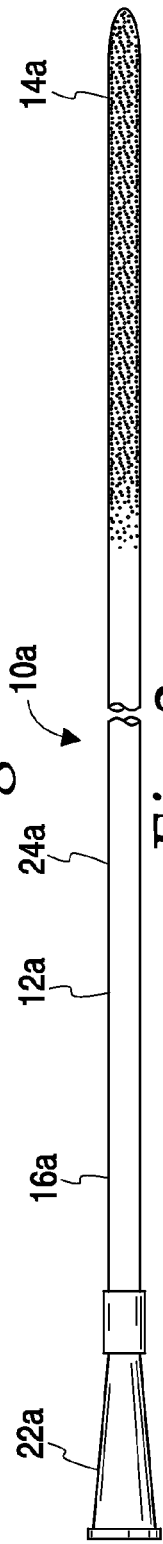
FIG. 2 is a side view of another embodiment of a catheter of the present disclosure having a tailored or modified density schematically represented by stippling.

Referring now to FIG. 2, the proximal insertion end portion 14a of catheter shaft 12a of catheter 10a has a density that is different than the other portions of the catheter, e.g., a density different from the distal end portion 16a, the drainage member 22a and/or the middle portion 24a of the catheter shaft 12a. In this embodiment, the proximal insertion end portion 14a is made of a material or combination of materials that is denser than the other portions of the catheter 10a. When catheter 10a is placed in water, the proximal insertion end portion 14a sinks downward in the water to a lower level while the distal end 16a floats or remains at a higher level above the proximal insertion end portion 14a.

Figure 3:
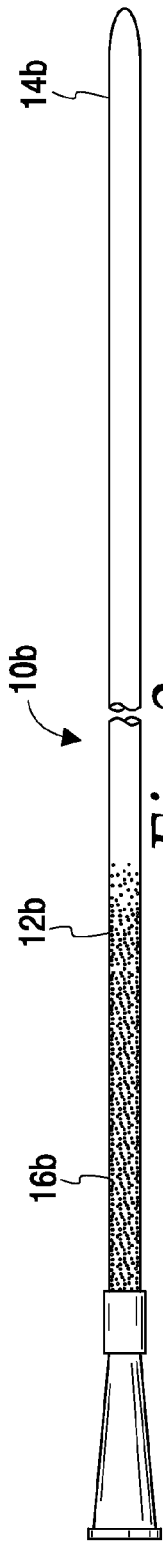
FIG. 3 is a side view of another embodiment of a catheter of the present disclosure having a tailored or modified density schematically represented by stippling.

Referring to FIG. 3, catheter shaft 12b of catheter 10b includes a distal end portion 16b which has a density that is greater than the density of the other portions of the catheter 10b. When catheter 10b is placed within water, the distal end portion 16b sinks downward in the water to a lower level while the proximal end portion 14b floats or remains at a higher level above the distal end portion 16b.

The density of the catheters disclosed herein and/or the density of the portions of the catheters may be modified or tailored in any suitable manner. For example, different portions of the catheter may be made from materials or combination of materials having different densities. In such an embodiment, one portion of the catheter may be constructed from a first material and a second portion of the catheter may be constructed from a second material of greater or lesser density. In one embodiment, the different portions of the catheter shaft may be made from different materials. For example, in the catheter show in FIG. 2, the proximal insertion end portion 14a of catheter shaft 12a may be made of a material having a greater density than the distal end portion 16a. In another embodiment, the catheter shaft may be made of one material and the drainage member may be made of another material. The catheters may be made in any suitable manner, e.g., extrusion, injection molding, and the like.

The density of the catheter and/or the different portions of the catheter may be modified or tailored by blending or combining one or more additive(s) with the base material or polymers from which the catheter is made. Such density modifying additives may be any suitable additive that modifies the density of the material which forms the catheter and/or portions of the catheter. Examples of such density modifying additives may include, but are not limited to, organic, inorganic or composite particles, which may be in the form of beads. The particles may be low density particles which can be used to increase the buoyancy of the material. Alternatively, the particles may be high density particles which may be used to decrease the buoyancy of the material. In one embodiment the additives are polymeric beads, such as silica beads. Other density modifying additives also may include air or the creation of air bubbles within the material during the manufacturing process. Still other density modifying materials may include phosphate-based glass fibers, such as fibers made from $Na_2OCaOP_2O_5$ which include copper or silver ions. Other fillers may include magnesium alloys beads (such as MgOH beads), calcium carbonate, sodium chloride, sodium bicarbonate, calcium oxide (lime), and calcium hydroxide. The additives may be added to the catheter/catheter parts of the material forming the same during the manufacturing process.

In addition to affecting density, the additives may also provide other desired catheter characteristics or properties, such as enhancing mechanical and/or chemical properties of the catheter. For example, the additives may enhance pushability, torque transmission, lubricity, water solubility, consistency, elasticity, processability, and shelf-life. The additives also may impart oligodynamic or antimicrobial properties to the catheter. For example phosphate-based glass fibers may include copper or silver ions that are released to provide oligodynamic properties.

As mentioned above, additives may be added to the material of the catheter to increase or decrease the density of the different portions of the catheter. Referring to FIG. 2 for example, in one embodiment, the material from which the proximal insertion end portion 14a is formed may include an additive which makes the proximal insertion end portion 14a denser than the distal end portion 16a. Alternatively, the distal end portion 16a may include an additive which makes the distal end portion 16a less dense than the proximal insertion end portion 14a. In another alternative, both the proximal and distal ends may include additives wherein the proximal insertion end portion 14a may include an additive which makes the proximal insertion end portion 14a denser than the distal end portion 16a and the distal end portion 16a may include an additive which makes the distal end portion 16a less dense than the proximal insertion end portion 14a. When an additive is employed, the entire catheter may be made from the same base material or portions of the catheter may be made from different base materials to which the additives are added.

Turning now to the embodiment illustrated in FIGS. 4-7, similar to the embodiments illustrated in FIGS. 2 and 3, each of these embodiments includes one or more portions that have a density which is different from other portions of the catheter such that the catheter will move or self-orientate into a desired orientation when placed within water. Also, the density of the catheter and/or catheter portions may be modified or tailored in any of the above-discussed manners, e.g. constructing portions of the catheter from different materials, employing additives, etc.

Referring to the embodiment illustrated in FIG. 6, the drainage member 22e of catheter 10e has a density that is different from other portions of the catheter. In this embodiment, the drainage member 22e is denser than the catheter shaft 12e (which itself may have portions of variable density as shown in FIGS. 2-5). In FIG. 6a, the density of the catheter 10i may be continuously graduated from the drainage member 22i toward the proximal end insertion tip 18i of the catheter shaft 12i. In the illustrated embodiment, the catheter 10i gradually decreases in density from the drainage member 22i in a direction toward the proximal end insertion tip 18i. In other embodiments, the density may increase in density from the drainage member 22i in a direction toward the proximal end insertion tip 18i. In the embodiment of FIG. 7, the middle portion 24f of the catheter shaft 12f has a density different than both the proximal and distal end portions 14f, 16f of the catheter shaft 12f. In another embodiment, which is not shown, the middle portion of catheter shaft may have a density which is the less than the proximal and distal end portions of the catheter shaft.

Figure 4:
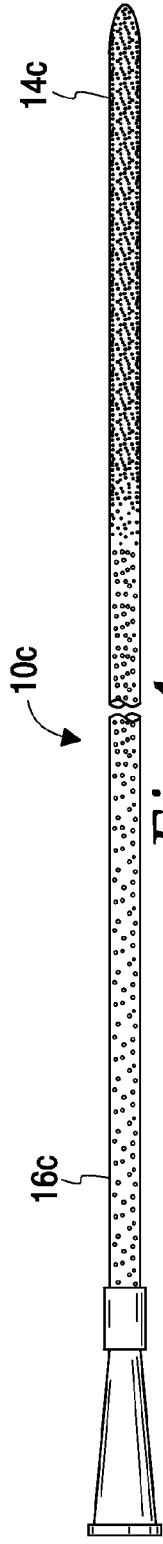
FIG. 4 is a side view of another embodiment of a catheter of the present disclosure having a tailored or modified density schematically represented by stippling.

As schematically shown in FIGS. 4, 5 and 7, the density of the catheter may be graduated over the length of the catheter wherein the density of the catheter gradually increases/decreases in one direction or another along the length of the catheter. For example, in catheter 10c illustrated in FIG. 4, the density gradually increases from the distal end portion 16c toward the proximal end portion 14c. In the catheter 10d shown in FIG. 5, the density gradually increases from the proximal insertion end portion 14d toward the distal end portion 16d. In FIG. 7, the density of catheter 10f gradually decreases from the middle portion 24f in both the direction of the proximal insertion end portion 14f and the direction of the distal end portion 16f. Alternatively, the density could decrease from the proximal and distal end portions towards the middle portion of the catheter.

In any of the catheters disclosed herein, the catheter or portions of the catheter (including the catheter shaft or portions thereof, the funnel, etc.) may, for example, have a tailored density of between about 0.4 g/cm$^3$ and about 1.2 g/cm$^3$ to enhance flushability of the catheter. Although it is also within the scope of the present disclosure for the catheter assembly or one or more of its individual components to have a density that is outside of this range. Preferably, the tailored density is between about 0.68 g/cm$^3$ and about 0.89 g/cm$^3$. In one embodiment, the catheter shaft has a density selected to enhance flushability. In another embodiment, portions of the catheter shaft have densities selected to enhance flushability. In a further embodiment, the funnel portion of the catheter has a density selected to enhance flushability.

In other embodiments, the density of the catheter may be tailored by a density modifying member or structure that may be attached to the catheter. In such an embodiment, the density modifying member may be attached to the catheter during manufacture or by the end user. The density modifying member could be attached anywhere along the catheter shaft or funnel in any suitable manner. The density modifying member could be, for example, a c-clip that is clipped to the catheter or a doughnut shaped member that is slid over the shaft of the catheter. Furthermore, any of the water capture elements disclosed herein also could function as a density modifying element. The density modifying element may be used to sink or float the catheter, a portion of the catheter or a water capture element to a desired level within water and/or could cause the catheter to self-orientate in water.

As illustrated in FIGS. 8, 9b, 11, 12, 14, 15, 17-19 and 24-48, any of the urinary catheters disclosed herein may be placed or moved into a compact configuration to enhance the flushability of the catheter. The compact configuration of the catheter results in reducing the elongated dimension of the catheter and compaction of the mass of the catheter into a closer or tighter configuration, both of which enhance the movement of the catheter down the toilet and/or across the U-bend pipe.

In FIG. 8, catheter 10f is shown in a compact configuration wherein the catheter shaft 12f has been knotted, wound or twisted such that the catheter 10f is secured in the compact configuration. As shown in this figure, the elongated dimension of the catheter is reduced and the mass of the catheter is more compact.

FIGS. 9a and 9b illustrate a catheter package 30 in which a catheter may be packaged for distribution to the end user. Referring to FIG. 9a, a strip 32 of the package 30 is torn in an elongated direction to open the package 30 for removal of the catheter therefrom. The package 30 may tear along strip 32 with the aid of a tear strip, cut line or directional tear packaging material. The package 30 also may be designed to open in a direction perpendicular to the elongated axis of the package 30 instead of or in addition to opening in the elongated direction.

Turning to FIG. 9b, after the catheter has been used to drain the patient's bladder, the catheter may be placed back in the package 30 for disposal of the catheter. The package 30 may be folded or bent with the spent catheter contained therein to place the catheter and package 30 into a compact configuration. The strip 32 or other securing element may be used to secure the package 30 and catheter therein in the compact configuration. The package 30 having the spent catheter therein may then be disposed of in the toilet. The package 30 is preferably made from a water disintegratable material that disintegrates over a desired period of time when placed in contact with toilet water. The package 30 may be made from any of the water disintegratable or enzymatically hydrolysable materials disclosed herein.

FIG. 16 illustrates another embodiment of a flushable intermittent urinary catheter 10g having a protective sleeve 34 and an introducer tip 36. The protective sleeve 34 surrounds at least a portion of the catheter shaft 12g to separate and enclosed the portion of the catheter shaft 12g from the outside environment. Furthermore, the user may grasp the catheter 10g through the protective sleeve 34 to handle and manipulate the catheter 10g. The protective sleeve 34 may have a distal end 38 that is attached to a distal end portion of the catheter shaft 12g or to the funnel 22g. A proximal end 40 of protective sleeve 34 is attached to the introducer tip 36. The protective sleeve 34, introducer tip 36 and catheter 10g may be made of any of the water disintegratable or enzymatically hydrolysable materials disclosed herein and may be disposed of by flushing down the toilet.

To drain the bladder of a patient, the introducer tip 36 is inserted into the urethral opening of the patient. The patient then grasps the catheter shaft 12g through the protective sleeve 34 to advance the catheter 10g through a slit or opening 35 in the introducer tip 36 to advance the catheter into the urethra. After urine has been drained from the bladder, the patient removes the catheter from the urethra of the patient and disposes of the catheter by flushing it down the toilet.

Referring to FIGS. 10-12, one or more securing elements 42 may be attached to protective sleeve 34 for securing the catheter in a compact configuration. The securing element 42 may be, for example, a strip of adhesive material or a tie. The securing element 42 may be attached to protective sleeve 34 or it may be integral therewith. FIGS. 11 and 12 show catheter 10g folded into a compact configuration. In the compact configuration, the catheter shaft 12g of catheter 10g may be folded, bent, wound or knotted. In FIG. 11, catheter 10g includes two securing elements 42 spaced apart along the length of the catheter. The securing elements 42 may be wrapped around the catheter shaft 12g to maintain or secure the catheter 10g in the compact configuration. In FIG. 12, the catheter 10g includes one securing element 42 which secures the catheter in the compact configuration. After catheter 10g has been used to drain a patient's bladder, the patient places (e.g., folds, bends, twists, winds, etc.) the catheter 10g into the compact configuration. The securing elements are then used to maintain the catheter 10g in the compact configuration.

In embodiments wherein the catheter does not include a protective sleeve 34, securing members, such as ties or strips, may be supplied with the catheter and placed about the catheter by the user after the catheter has been placed in the compact configuration for disposal of the catheter.

FIG. 13 illustrates another securing element in the form securing bracket, support or tray 44, which may be made from any of the water disintegratable or enzymatically hydrolysable materials disclosed herein. The tray 44 includes one or more furrows, clasps, grips, or grooves 46 that accept and hold a portion 11g of the catheter shaft 12g to secure or maintain the catheter 10g in a compact configuration for flushing down the toilet after use. In the illustrated embodiment, the tray 44 includes four grooves 46 but in other embodiments the tray 44 could include more than four grooves 46 or less than four grooves. The tray 44 also could, optionally, include a hinge 48 that allows for the tray 44 to be folded or bent in half to further compact a catheter held within the tray 44.

Referring now to FIGS. 14 and 15, the shaft 12g of catheter 10g is secured within tray 44 in a compact configuration. The catheter 12g is bent or folded and portions 11g of the catheter 10g are held in grooves 46 to secure the catheter in the compact configuration. While the tray 44 is shown with a catheter 10g having a protective sleeve and inserter tip, the tray 44 may be used with any catheters including any of the catheters disclosed herein, including those not having protective sleeves and inserter tips.

In one embodiment, the openings of grooves 46 are smaller than the diameter of the catheter shaft 12g so as to create a friction fit with the catheter shaft 12g. In other embodiments, the edges of the tray defining the openings of grooves 46 may include latches that form a snap fit with the portion 11g of the catheter shaft 12g inserted into the grooves 46. As illustrated in FIG. 15, when the tray 44 includes a hinge 48, the tray 44 may be bent about the hinge 48 to further compact the catheter 10g for disposal by flushing down the toilet.

In FIGS. 17-19, the catheter 10g is held in a compact configuration by a securing element that attaches or couples the inserter tip 36 with funnel 22g. The securing element may by a portion of the funnel, the inserter tip or both. As illustrated in FIG. 17, after use, the catheter 10g is knotted or twisted and the inserter tip 36 is attached to funnel 22g to secure the catheter 10g in the compact configuration. In FIG. 18, the catheter 10g is bent or curved and the inserter tip 36 and funnel 22g are attached. As shown in FIG. 19, a strip 42 optionally may be used to assist in securing the catheter 10g in the compact configuration.

FIGS. 20 and 21 illustrate exemplary embodiments securing elements for attaching the inserter tip 36 and funnel 22g. In the embodiment shown in FIG. 20, the funnel 22g includes an inner surface 50 that defines the distal opening in the end of the funnel 22g. The inserter tip 36 includes a protrusion or shoulder 52 which is sized to fit into the distal opening of the funnel 22g. The diameter or size of the distal opening of funnel 22g is slightly smaller than the outer diameter or size of the shoulder 52 of the inserter tip 36 such that when the shoulder 52 is inserted into the distal opening of the funnel 22g, the shoulder 52 forms a friction fit with the inner surface 50 of the funnel 22g to attached the funnel and inserter tip. In the embodiment shown in FIG. 21, the flange 54 of the inserter tip 36 includes an outer shoulder 56. A channel 58 is defined between the inner shoulder 52 and the outer shoulder 56. The channel 58 accepts the rim or flange 60 at the distal end of the funnel 22g to attach the inserter tip and funnel to each other.

FIGS. 22-24 illustrate another embodiment wherein the securing element may be associated with the funnel 22 and/or inserter tip 36. In FIG. 22, a securing element, such as clasp 62, is associated with the funnel 22, and in FIG. 23, a securing element, such as clasp 64, is associated with the inserter tip 36. In the illustrated embodiments, the securing elements are c-shaped clasps. In other embodiments, the securing elements may be other structures as well, such as for example adhesives or tie strips. Clasps 62 and 64 are sized to receive and hold the catheter shaft so as to secure the catheter in a compact configuration. Referring to FIG. 24, after use of the catheter 10h, the catheter 10h is placed in a compact configuration, such as by bending, winding or knotting the catheter shaft 12h, and portions of the catheter shaft are placed in clasps 62 and 64 to secure the catheter in the compact configuration.

FIGS. 25 and 26 illustrate a catheter disposal bag or pouch 66 in which a catheter 10 may be placed in for disposal thereof. The disposal bag 66 may be made from any of the water disintegratable or enzymatically hydrolysable materials disclosed herein. The disposal bag 66 may include one or more adhesive elements, such as adhesive patches 67, associated with the bag 66. In the illustrated embodiment, the adhesive patches 67 include double sided adhesive 68 wherein one side of the adhesive 68 is attached to the exterior surface of the bag 66 and the other side of adhesive 68 is attached to a release liner 69.

After the catheter 10 has been used, the user places the spent catheter 10 within the bag 66 and peels the release liner 69 from the adhesive 68. The user then folds the bag 66 having the catheter 10 therein into a compact configuration, such as the one illustrated in FIG. 26. The bag 66 and catheter 10 therein may then be disposed of by flushing down the toilet. The bag 66 and the catheter 10, in the compact configuration, move down the drain and out of the toilet bowl.

FIGS. 27 and 28 illustrate another embodiment of a catheter 10 which is folded or bent into a compact configuration for disposal thereof. In these embodiments, the catheter 10 is bent or folded into a compact configuration and a band or strip 70, 70a made of a water disintegratable or enzymatically hydrolysable material is wrapped around the catheter 10 to maintain the catheter 10 in the compact configuration. The band 70, 70a may be a strip of water soluble adhesive tape. After the user is finished using the catheter 10, the user bends the spent catheter 10 into a compact configuration and wraps the band or strip 70, 70a around the bent catheter 10 to maintain the catheter 10 in a compact configuration. The catheter 10 is then placed in and flushed down the toilet for disposal thereof wherein the band and the catheter will be disintegrated by the sewer water.

FIGS. 29-48 illustrate catheter gripping aids that may also include securing elements or features that may be used to secure a spent catheter in a bent or compact configure for disposal thereof and, in particular, for flushing down the toilet. The gripping aid may, for example, secure the catheter in a generally U-shaped or looped configuration. All of the gripping aids disclosed herein may be made from one or more of a suitable water disintegratable or enzymatically hydrolysable material, such as any of the above-identified water disintegratable polymers and/or flushable materials.

Figure 29:
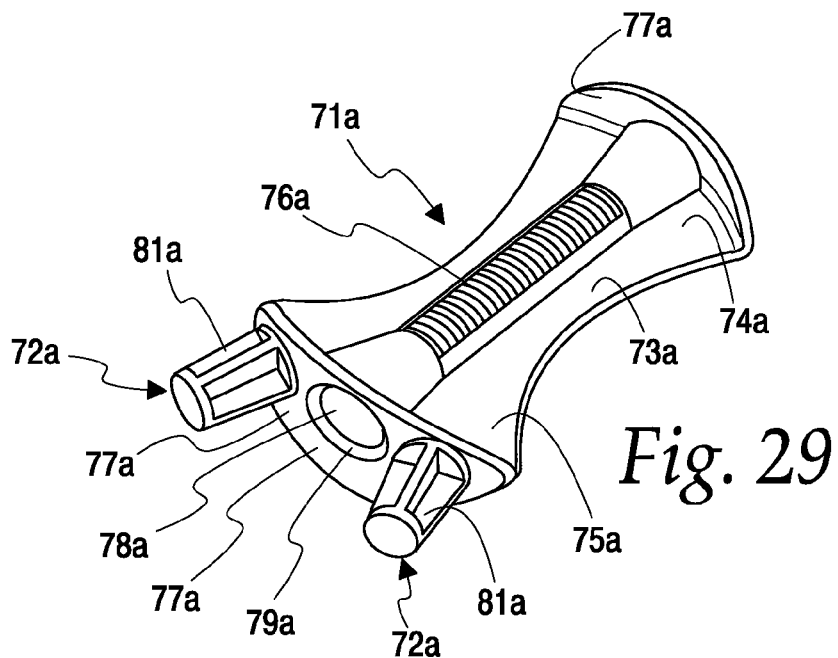
FIG. 29 is a perspective view of one embodiment of a catheter gripping aid of the present disclosure.
Figure 30:
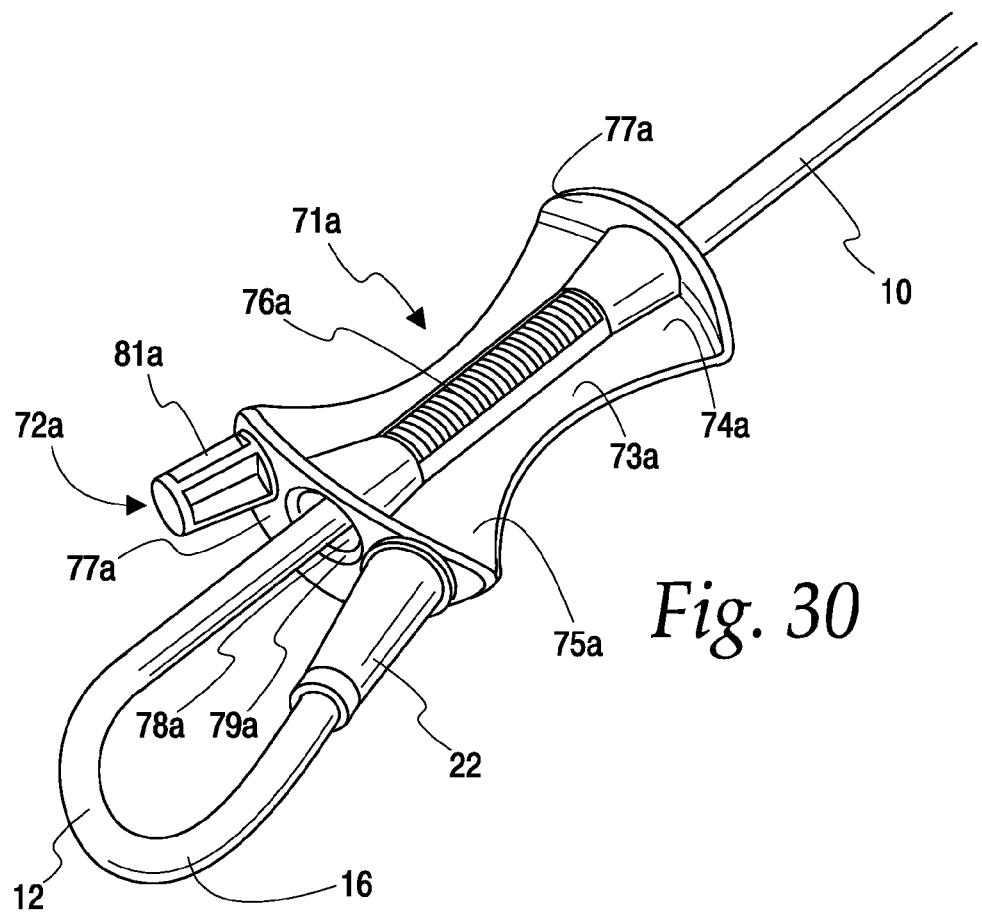
FIG. 30 is a perspective view of the catheter gripping aid of FIG. 29 shown mounted on a catheter and maintaining the catheter in a bent or compact configuration.

FIGS. 29 and 30 illustrate one embodiment of a catheter gripping aid 71a that may be used to grip the catheter 10 for handling thereof during insertion and withdrawal of the catheter during catheterization. The gripping aid 71a may also include a securing element 72a that may be used to maintain the catheter 10 in a bent or compact configuration for disposal thereof and, in particular, for disposal down the toilet.

Referring to FIG. 29, the gripping aid 71a includes a body 73a having a proximal end portion 74a, a distal end portion 75a and an intermediate portion 76a therebetween. The proximal and distal end portions 74a and 75a may include generally oval or circular shaped flanges 77a at the terminal ends thereof. The gripping aid 71a also includes a bore or a lumen 78a extending therethrough which is in communication with openings 79a in the proximal and distal ends. The catheter shaft 12 is received into the bore 78a so that the gripping aid 71a can slide along the catheter shaft 12. The intermediate portion 76a may include a rounded or raised resilient section 80a that is associated or aligned with the bore 78a. This resilient section 80a can be deformed under pressure from the user's fingers to move the gripping aid 71a into contact with the catheter shaft 12 so that the user may grasp the catheter shaft 12 through the gripping aid 71a. In particular, the user may pinch the intermediate portion 76a of the gripping aid 71a between his or her fingers to handle and manipulate the catheter 10. As shown in the illustrated embodiment, the intermediate portion 76a may optionally include a textured surface, such as the ribbed surface shown in the figures, which provides a gripping surface for the user and a tactile indicator for the user to indicate that the user is gripping the intermediate portion 76a of the gripping aid 71a.

The gripping aid 71a includes one or more securing elements 72a for securing the catheter 10 in a bent, compact configuration. The catheter 10 may be bent into the generally U-shaped of looped configuration as shown in FIG. 30. In the illustrated embodiment, the gripping aid 71a includes a securing element 72a associated with the distal end portion 75a of the gripping aid 71a. In particular, the gripping aid 71a includes posts or protrusions 81a extending from the flange 77a on the distal end portion 75a of the gripping aid 71a. The posts 81a may be located on either side of opening 79a. After the user is finished using the catheter 71a, the user bends the distal end portion 16 of the catheter shaft 12 and inserts one of the posts 81a into the opening of the funnel 22 of the catheter 10. The size or the extend of the U-shaped bend of the catheter 10 may be varied by sliding the gripping aid 71a proximally and distally along the catheter shaft, e.g., the more proximal the location of gripping aid 71a, the larger the U-shaped bend. The catheter shaft may optionally include a visual indicator to indicate a suggested placement of the gripping aid 71a. In the illustrated embodiment, funnel 22 of the catheter 10 remains attached to the post 81a by a friction fit. In other embodiments, funnel 22 may be attached to the post 81a by an adhesive or snap-fit. The catheter 10, in the compact configuration, is flushed down the toilet.

Figure 32:
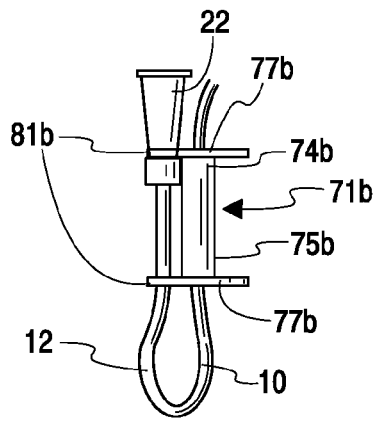
FIG. 32 is a perspective view of the catheter gripping aid of FIG. 31 shown mounted on a catheter and maintaining the catheter in a bent or compact configuration.
Figure 31:
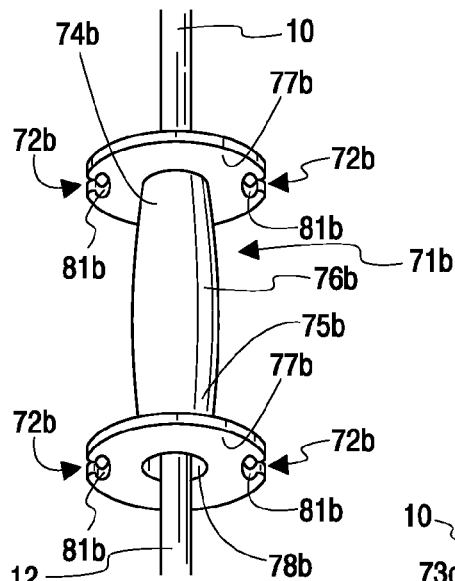
FIG. 31 is a perspective view of another embodiment of a catheter gripping aid of the present disclosure.

FIGS. 31 and 32 show another embodiment of a catheter gripping aid 71b that includes one or more securing elements 72b for securing the catheter 10 in a bent or compact configuration. The catheter gripping aid 71b includes a proximal end portion 74b, a distal end portion 75b and an intermediate portion 76b. The gripping 71b also includes a bore 78b extending therethrough for receiving catheter shaft 12. The body of the gripping aid 71b is generally cylindrically shaped and the gripping aid 71b includes generally disc shaped flanges 77b at the proximal and distal end portions 74b and 75b. The generally disc shaped flanges 77b have a larger diameter than the body. At least one of the flanges 77b includes a securing element 72b for securing the catheter 10 in a bent or compact configuration. In one embodiment, at least one flange 77b may include a recess or clasp 81b that receives a portion of the catheter shaft 12 or funnel 22. In the illustrated embodiment, each flange 77b includes a pair of opposed clasps 81b. As shown in FIG. 32, after the user is finished using the catheter 10, the catheter 10 is bent and the catheter shaft 12 and/or funnel 22 are inserted into the clasp 81b. The catheter shaft 12 and/or funnel 22 remain in the clasp 81b by friction or snap-fit.

Figure 33:
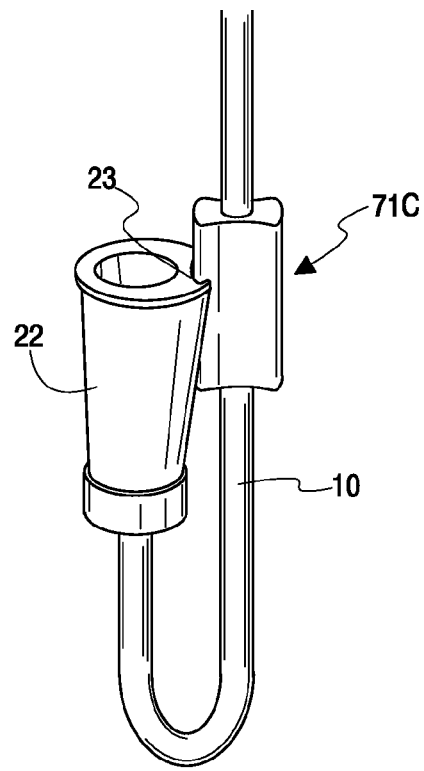
FIG. 33 is a perspective view of another embodiment of a catheter gripping aid of the present disclosure, showing the catheter gripping aid maintaining the catheter in a bent or compact configuration.

FIG. 33 shows another embodiment of a gripping aid 71c that can be used in conjunction with the catheter funnel 22 to secure or maintain the catheter 10 in a bent or compact configuration. In this embodiment, the funnel 22 includes a recess or clasp 23 which has a cross-sectional shape similar to that of the gripping aid 71c. The clasp 23 receives and retains the gripping aid 71c to secure the catheter 10 in the bent configuration. In the embodiment shown, the gripping aid 71c has a generally rectangular cross-section and recess or claps 23 of the funnel 22 has a shape configured to receive and retain the gripping aid 71c. The gripping aid 71c may remain attached to the funnel 23 by friction or snap-fit with the recess or clasp 23.

Figure 35:
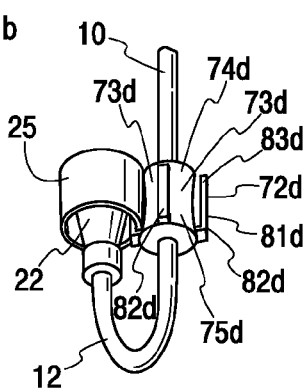
FIG. 35 is a perspective view of the catheter gripping aid of FIG. 34 mounted on a catheter and maintaining the catheter in a bent or compact configuration.
Figure 34:
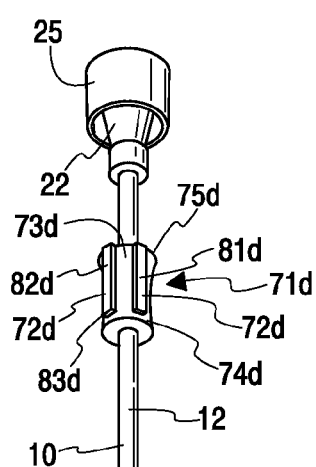
FIG. 34 is a perspective view of another embodiment of a catheter gripping aid of the present disclosure.

FIGS. 34 and 35 show another embodiment of a gripping aid 71d that includes securing elements 72d for securing the catheter 12 in a bent or compact configuration. Referring to FIG. 34, the gripping aid 71d includes a generally cylindrically shaped body 73d having a proximal end portion 74d and a distal end portion 75d. The securing elements 72d include clips 81d that are associated with the gripping aid 71*d*. The distal end 82*d* of the clips 81*d* are attached to the gripping aid 71*d* and extend proximally. The clips 81*d* have a free end 83*d*. The funnel 22 of the catheter 10 includes a generally cylindrical wall 25 extending proximally around the funnel. When the user is finished with the catheter 10, the catheter is bent into a compact configuration and the clips 81*d* are attached to the generally cylindrical wall 25 surrounding the funnel 22. The cylindrical wall 25 is positioned between the clip(s) 81*d* and the body 73*d* of the gripping aid 71*d*. Catheter 10 may then be disposed of down the toilet in the bent or compact configuration.

Figure 36:
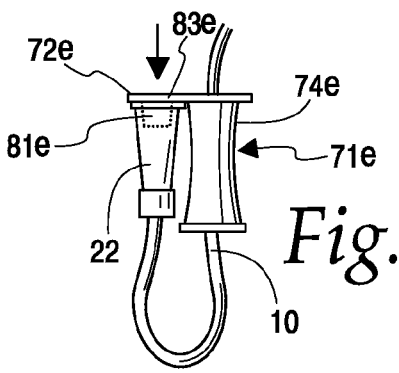
FIG. 36 is a perspective view of another embodiment of a catheter gripping aid of the present disclosure shown maintaining the catheter in a bent or compact configuration.

FIG. 36 illustrates another embodiment of a gripping aid 71*e* that includes a securing element 72*e*. In this embodiment, the securing element 72*e* includes an extension 83*e* projecting radially from the proximal end portion 74*e* of the gripping aid 71*e*. A projection or post 81*e* projects distally from the extension. After the user is finished with the catheter 10, the catheter 10 is bent into a compact configuration and the post 81*e* is inserted into the opening of the funnel 22. The funnel 22 remains attached to the post 81*e* by friction or snap-fit. The catheter 10 in the compact configuration may be flushed down the toilet for disposal thereof.

Figure 37:
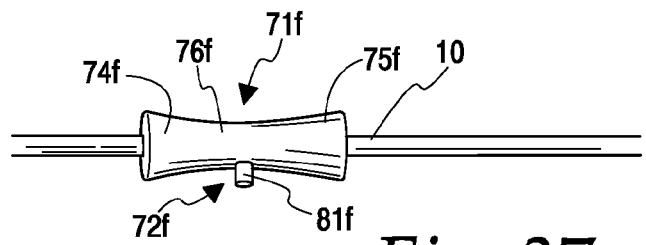
FIG. 37 is a perspective view of another embodiment of a catheter gripping aid of the present disclosure shown mounted on a catheter.
Figure 38:
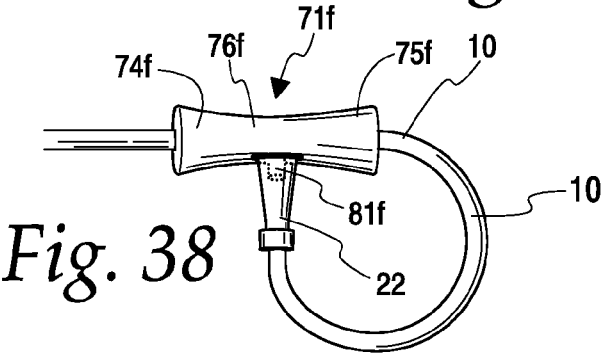
FIG. 38 is a perspective view of the catheter gripping aid of FIG. 37 shown maintaining the catheter in a bent or compact configuration.

FIGS. 37 and 38 illustrate another embodiment of a gripping aid 71*f* of the present disclosure. In this embodiment, the gripping aid 71*f* includes a securing member 72*f* extending radially outwardly from the exterior surface of the gripping aid 71*f*. The gripping aid 71*f* includes a proximal end portion 74*f*, a distal end portion 75*f* and an intermediate portion 76*f* therebetween. In the illustrated embodiment, the securing member 72*f* includes a projection or post 81*f* associated with the intermediate portion 76*f* of the gripping aid 71*f*. After the user is finished using the catheter 10, the catheter 10 is bent into a compact configuration and the post 81*f* is inserted into the opening of the funnel 22. The funnel 22 remains attached to the post 81*f* by friction or snap-fit. Catheter 10 in the bent or compact configuration may be flushed down the toilet.

FIGS. 39-46 illustrate gripping aids that may be bent into a U-shaped configuration to secure the catheter in a bent or compact configuration. In these embodiments, the gripping aid may secure the catheter in a generally U-shaped configuration for disposal down the toilet.

Figure 39:
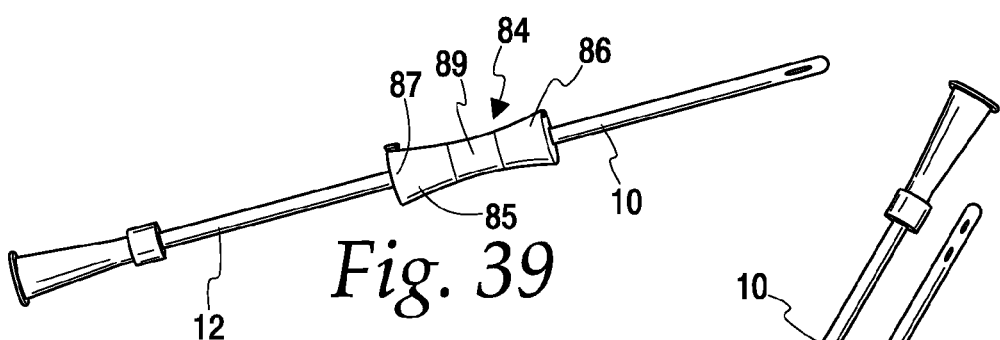
FIG. 39 is a perspective view of another embodiment of a catheter gripping aid of the present disclosure shown mounted on a catheter.

Referring to FIG. 39, the gripping aid 84 includes a body 85 having a proximal end portion 86, a distal end portion 87 and an intermediate portion 89 therebetween. The intermediate portion 89 may be generally cylindrically shaped and the proximal and distal end portions 86 and 87 may each have a generally conical shape that flares radially outwardly toward the terminal end thereof. A bore or lumen 90 (FIG. 41) extends through the gripping aid 84 and receives the catheter shaft 12 therethrough.

Figure 40:
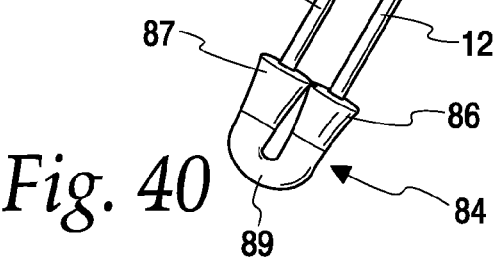
FIG. 40 is a perspective view of the catheter gripping aid of FIG. 39 shown maintaining the catheter in a bent or compact configuration.

The proximal and distal end portions 86 and 87 may be substantially rigid and the intermediate portion 89 may be relatively flexible so that it bends. Referring to FIG. 40, the intermediate portion 89 of the gripping aid 84 may be bent to move the gripping aid 84 into a U-shaped configuration. The intermediate portion 89 may be plastically deformable so that the gripping aid 84 remains in the U-shaped configuration after the gripping aid 84 is bent. When gripping aid 84 is bent with the catheter 10 located within the bore 90, the catheter 10 also is placed into a bent or compact configuration.

Referring to FIG. 41, the gripping aid 84 may optionally include securing members for securing or maintaining the gripping aid 84 in the U-shaped configuration. For example, one of the proximal and distal end portions 86 and 87 may include a recess 91 and the other of the end portions may include a projection 92 that fits into the recess 91. In the illustrated embodiment, the projection 92 snap-fits into the recess 91 to create a friction fit that maintains the gripping aid 84 in a U-shaped configuration. FIG. 42 illustrates another embodiment of gripping aid 84*a* wherein the gripping aid 84*a* has a generally oval cross-sectional shape as compared to the more circular cross-section shape shown in FIG. 41. The gripping aid 84*a* also includes securing members 91*a* and 92*a*.

Referring to FIG. 44, the intermediate portion 89 of gripping aid 84 may be made relatively flexible as compared to the proximal and distal ends by a reduction of material in the portion 93 of the intermediate portion 89. Portion 93 is the portion that becomes the root of the U-shaped configuration. In another embodiment, shown in FIG. 45, the intermediate portion 89*b* may be made flexible by a slit, slots or cut out 94 in the portion that becomes the root of the U-shaped configuration. Referring to FIGS. 43-45, the gripping aid 84 may include a cuff 95 that surrounds and is slidable along the gripping aid 84. In the initial position, which is shown in FIG. 43, the cuff 95 is positioned over the intermediate portion 89. When the cuff 95 is in this position, it prevents the gripping aid 84 from being bent, i.e., keeps the gripping aid 84 in a straight configuration while being used as a gripper. As shown in FIG. 46, when the cuff is slid over the proximal or distal end portions 86/87, the intermediate portion 89 may be bent to place the gripping aid 84 in the U-shaped configuration, which results in placing the catheter 10 in a U-shaped configuration.

Figures 47, 48:
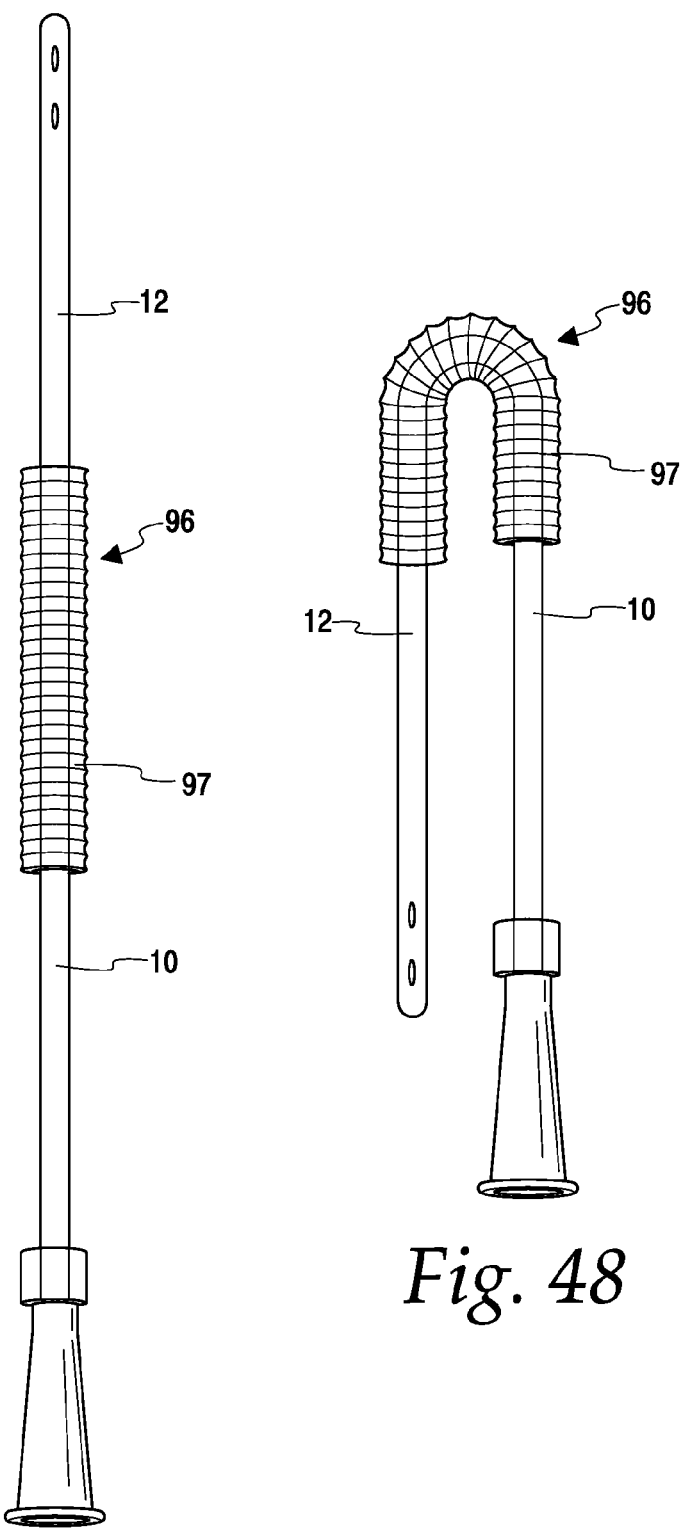
FIG. 47 is a perspective view of another embodiment of a catheter gripping aid of the present disclosure shown mounted on a catheter.
FIG. 48 is a perspective view of the catheter gripping aid of FIG. 47 shown maintaining the catheter in a bent or compact configuration.
Figures 61A, 61B:
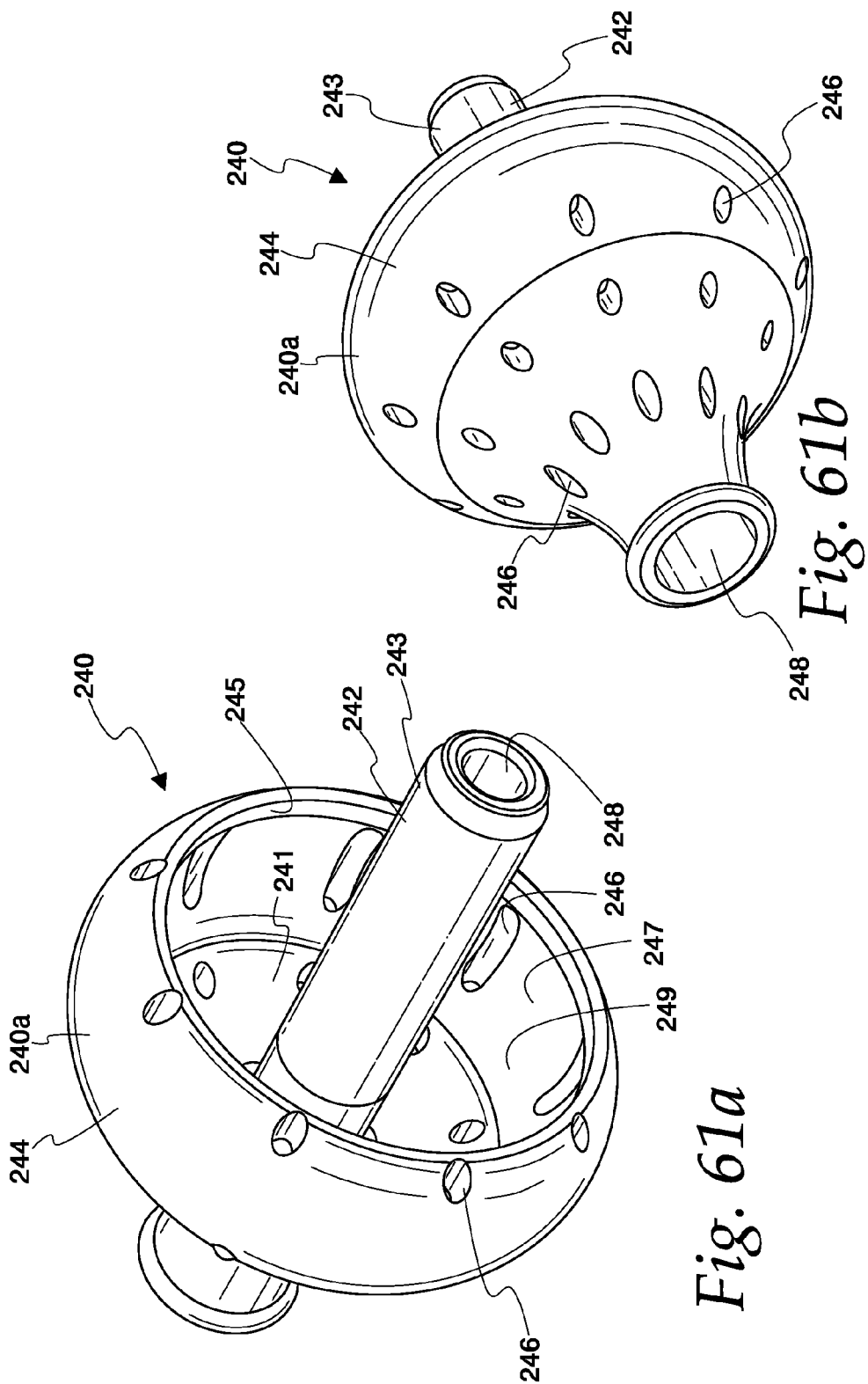
FIGS. 61a and 61b are perspective views of another embodiment of a water capture element of the present disclosure.

Referring to FIGS. 47 and 48, there is shown in another embodiment of a catheter gripping aid 96 of the present disclosure that may be used to secure the catheter in a U-shaped compact configuration. In this embodiment, the gripping aid 96 includes a generally tubular body 97 having a bore of a lumen extending therethrough for passage of the catheter shaft 12. At least a portion of the body 97 includes a corrugated wall similar to that of a bendable drinking straw. When the corrugated wall is bent, it maintains the bent shape until it is subsequently bent again. After the user is finished with the catheter 10, the user may bend the gripping aid 96 into a U-shaped configuration to place the catheter 10 in a bent, compact configuration for flushing down the toilet. The corrugated wall of the body 97 maintains the gripping aid 96 and the catheter 10 in the U-shaped configuration.

Alternatively or in addition to tailoring the density of the catheter, the surface energy or geometry of the catheter or portions of the catheter may be tailored or modified such that at least one portion of the catheter overcomes the surface tension of the water to sink within the water. In order for a solid material denser than water to sink, the material must first overcome the surface tension of the water. Thus, a catheter or portion of the catheter may have a surface free energy and/or geometry that are designed to overcome the surface tension of the water which can assist in allowing the catheter to sink and/or self-orientate within the water. For example, the drainage member of a catheter may have a surface energy and/or geometry that are tailored to overcome the surface tension of the water such that the drainage member sinks within the water while another portion floats at a desired level of the water resulting in self-orientation of the catheter within the water.

Any of the catheters disclosed herein, and any other flushable catheters, may include one or more water capture elements associated with the catheter to enhance the flushability of the catheter by assisting in propelling the catheter down the toilet and/or across the trapway/U-bend pipe of a sewer system. The water capture elements are configured to be contacted by flushing water such that the force of the flushing water and/or siphoning force acts on the water capture elements to facilitate propelling the catheter down the toilet and/or across the trapway/U-bend pipe of the sewer system. In other words, the energy of the flushing water is transferred to the water capture elements to facilitate movement of the catheter down the toilet. The water capturing elements may increase and/or cause a generation of flushing or drag forces that act upon the catheter such that the flushing forces overcome the retaining forces (e.g., buoyancy, water tension, and adhesion and/or attraction to the sidewalls of the toilet) that urge the catheter to remain within the toilet bowl during flushing.

In one embodiment, the flushing water contacts the water capture elements and the force of the water moves the catheter at least out of the toilet bowl such that it is out of visual sight. Preferably, the flushing water also forces or moves the catheter past the trapway/U-bend of the sewer pipes. The water capture elements may have one or more vanes which extend radially outwardly from the axis of the catheter shaft. The water capture elements, including the vanes, may include sections or portions that extend radially and/or axially relative to the catheter.

As schematically illustrated in FIG. 49, any of the water capture elements disclosed herein may have a maximum dimension MD as measured from the a longitudinal axis A of the catheter shaft to a point of the water capture element which is furthest from the axis A of the catheter shaft 12 in a radial direction. The maximum dimension of the water capture element and associated vane may be, but does not necessary have to be, at least about 5 to 7 times of the radius of the catheter shaft 12. In FIG. 49, the maximum dimension of the vane is schematically represented as a circle for purposes of illustration. It will be understood that the water capture element could be any suitable shape, including those described below, and that maximum dimension may be a point on any of the variously shaped water capture elements. As used herein, the term "maximum dimension" refers to the portion of the water capture element that is radially furthest from the longitudinal axis of the catheter.

FIGS. 50a-65b show perspective views of different configurations of water capture element that include one or more vanes having shapes such as fins, wings, or other structures. Any of the water capture elements disclosed herein may be associated with any of catheters discussed herein or any other flushable catheter.

In the embodiments illustrated in FIGS. 50a-65b, the water capture elements may be associated with the drainage member, e.g. funnel, of the catheter. The drainage members fluidly connect the urine flow path of the catheter to a collection container, such as a collection bag, or direct urine into a collection receptacle, such as a toilet. Accordingly, the drainage members of any of the embodiments disclosed herein may include structures or features for attachment to and drainage into urine collection bags.

In other embodiments, the water capture elements may be associated with other portions of the catheter. Additionally, the water capture elements may be integrally formed with the catheter or the water capture elements may be a separate component(s) or part of a separate component which is attached to the catheter by the user prior to or after drainage of the bladder and prior to placement into the toilet for disposal thereof. In one embodiment, a water capture element, including one or more vanes, may be a separate component that is joined to the catheter, by for example, insertion into the drainage member of the catheter after the catheter has been used to drain the bladder. In another embodiment, a water capture element may be mechanically (e.g., clipped or push fit), or adhesively attached to a portion of the catheter, by the user prior to or after catheter use.

The water capture elements may be made of any suitable material. For example, the water capture elements may be made from a polymer or combination of polymers. Preferably, the water capture elements are made from water disintegratable or enzymatically hydrolysable materials, such as any of the above-identified water disintegratable polymers and/or flushable materials. In one embodiment, the water capture element is made from pulp cellulose, such as facial tissue paper or toilet paper. In such an embodiment, the water capture elements may be attached to the catheter during manufacturing or after catheter use.

Any of the water capture elements disclosed in FIG. 50a-65b also may be configured to move from a collapsed configuration prior to use to an expanded configuration after drainage of the bladder.

Additionally, the water capture elements may have a density that is the same as or different from the other portions of the catheter. The density of the water capture elements may also be modified or tailored by the addition of one or more of the above-discussed density modifying additives. The density of the water capture elements may be selected or tailored such that the density of the water capture element causes it to sink or float to a desired level within the water or causes the catheter to orientate itself for optimal flushing e.g., with the water capture element or vanes facing the flushing water. In such an embodiment, the density of the other portions of the catheter, optionally, may be selected or tailored such that the other portions of the catheter float or remain at a level above the water capture element. In other embodiments, the density of the water capture element may be selected or tailored such that the water capture element floats up to a desired level within the water and other portions of the catheter may be selected or tailored to sink or float to a level below the water capture element. In another embodiment, the densities of the portions of the catheter immediately adjacent to the water capture element may be selected or tailored to located the water capture element at a desired level within water.

As mentioned above, while the water capture element in FIGS. 50a-65b are shown associated with a drainage member, the water capture may be associated with other portions of the catheter in any other suitable manner.

Referring to FIGS. 50a and 50b, the drainage member 130 includes a stem 132 and a water capture element 133. The water capture element 133 includes one or more vanes 134 extending radially outwardly therefrom and circumferentially about the stem 134. In this embodiment, the vanes 134 are generally disc-shaped. In one embodiment the generally disc-shaped vanes are crenated so as to have rounded members or petals 136 located around at least a portion of the margins of the vanes 134. Additionally, the vanes 134 each include a proximal surface 135 configured for contacting flushing water and receiving energy from the flushing water to facilitate movement of the catheter down the toilet. In other words, the force of flushing water impinges on the proximal surface 135 to propel movement of the catheter. In the illustrated embodiment, surface 135 is tapered inwardly toward stem 132. The vanes 135 may also be concentric about a common axis or non-concentric.

The stem 132 of the drainage member 130 may be attached to or formed with the distal end portion of the catheter and the drainage member 130 may include a urine passageway 138 for the passage of urine therethrough during drainage of the bladder.

In an alternative embodiment, a water capture element having vanes substantially similar to those illustrated in FIGS. 50a and 50b may be attached to the catheter by the user after the catheter has been used and just prior to disposal of the catheter. In such an embodiment, the water capture element may optionally have a stem portion that is insertable into a drainage member, such as, for example, drainage member 22 of FIG. 1. If the water capture element includes a stem, an internal passage, such as urine drainage passage 138 (FIGS. 50a and 50b), is not required. The stem of the water capture element may be held in place within the drainage member by a friction fit or an adhesive.

In other embodiments, the water capture element may not include a stem and the water capture element may be attached to the catheter in any suitable manner. For example, the water capture element may be joined to the end of the drainage member with an adhesive. In one embodiment, the water capture element may include a disc shaped vane that has a diameter larger than the drainage opening in the distal end of the drainage member. The water capture element may be placed over the drainage opening like a cap or cover having a periphery that extends radially outwardly from the drainage member. The water capture element may be attached to the drainage member by an adhesive between the rim defining the opening the drainage member and the surface of the water capture element. In yet another embodiment the water capture element may be attached to the drainage member by a push fit attachment.

The water capture elements that can be attached to the catheter by the user may take on any of the water capture element configurations shown in FIGS. 51a-65a and may or may not include stems. The water capture elements also may be attached to the catheter in any suitable manner, e.g., insertion of a stem portion, when present, into the drainage member of the catheter.

Referring back to FIGS. 50a and 50b, after the user has emptied his/her bladder, the user places the catheter in the toilet for disposal and flushes the toilet. During flushing, the flushing water impinges on the vanes 134 and in particular on proximal surface 135. The energy of the flushing water is transferred to the vane to propel the catheter down the toilet and/or across the trapway/U-bend of the sewer pipes.

In FIGS. 51a and 51b, the drainage member 140 includes a stem 142 and a urine drainage passageway 148. The drainage member 140 also includes a water capture element 143 having one or more vanes 144. In this embodiment, the water capture element 143 is generally mushroom-shaped wherein the vane 144 extends radially outwardly in all directions from the stem 142. The vane 144 also has a concave proximal surface 145 configured to contact flushing water so that the force of the flushing water impinges on the vane 144. Optionally, the vane 144 may also include apertures 146 therethrough which increases the amount of surface area contacted by the flushing water and aids in movement of the vane 144 and catheter down the toilet under the force of the water. The apertures may also result in a faster rate of water deterioration of the water disintegratable materials (e.g. dissolution, degradation, hydrolysis, etc.) because the apertures provide a larger surface area for the water to contact.

Referring to FIGS. 52a and 52b, the drainage member 150 includes a stem 152 and a urine drainage passageway 158 therethrough. The drainage member 150 also includes a water capture element 153 having a plurality of vanes 154 projecting radially outwardly from stem 152, similar to a propeller or fan. In the illustrated embodiment, the vanes 154 are generally elongated cuboidal projections. The water capture element 153 is shown in FIGS. 52a and 52b with three generally cuboidal vanes 154; however, in other embodiments the water capture element 153 could include more or less than the three vanes 154 shown in these figures and the vanes could also have a generally rounded configuration which may prevent snagging in sewer pipes. Additionally, in the illustrated embodiment, the vanes 154 are equally spaced about around the stem 152. In other embodiments, the spacing of the vanes 154 may be uneven. The vanes 154 may, optionally, include apertures 156 extending therethrough which increase the amount of surface area contacted by water. In other embodiments, the vanes 154 may not include any apertures.

Referring to FIGS. 53a and 53b, the drainage members 160, 170 include water capture elements 161, 171 having a plurality of generally paddle shaped vanes 164, 174 radially spaced from the stem 162, 172 and projecting toward the proximal end portion 163, 173 of the stem 162, 172. The drainage members 160, 170 also include a passageway 168, 178 therethrough for the drainage of urine.

The water capture element 161 illustrated in FIGS. 53a and 53b includes six generally paddle shaped vanes 164 radiating from a distal wall 165. The vanes 164 and distal wall 165 define a proximal surface 167 which is configured to contact flushing water so that the force of the flushing water impinges on the surface 167. The water capture element 171 illustrated in FIGS. 54a and 54b includes three generally paddle shaped vanes 174 radiating from a distal wall 175. The vanes 174 and distal wall 175 define a proximal surface 177 which is configured to contact flushing water so that the force of the flushing water impinges on the surface 177. In other embodiments, the water capture element could include more or less generally paddle shaped vanes 164, 174 than that which is illustrated in these figures.

Turning to FIGS. 55a and 55b, the drainage member 180 includes a stem 182 and a urine drainage passageway 188 therethrough. The drainage member 180 also includes a water capture element 183 having two elongated vanes 184 projecting generally perpendicular to each other. Each of the vanes 184 includes a proximal surface 185 configured to contact flushing water so that the force of the flushing water impinges on the surface 185. In the embodiment illustrated in FIGS. 56a and 56b, the drainage member 190 includes a stem 192 and a urine drainage passageway 198 therethrough. The drainage member 190 also includes a water capture element 193 having two elongated vanes 194 extending generally parallel with respect to each other. Each of the vanes 184 includes a proximal surface 195 configured to contact flushing water so that the force of the flushing water impinges on the surface 195. In each embodiment, the vanes 184 and 194 may be different shapes and/or sizes or may be the same shapes and/or sizes.

In FIGS. 57a and 57b, the drainage member 200 includes a stem 202 and a passageway 208 therethrough for drainage of urine. The drainage member 200 also a water capture element 203 includes a pair of opposed generally bowl-shaped vanes 204 which in the illustrated embodiment are generally hemispherical hollow members. The vanes 204 could both face the same direction or the openings could be at a 90 degrees angle relative to each other. Each of the vanes 204 includes an internal concave proximal surface 205 configured to contact flushing water so that the force of the flushing water impinges on the surface 205. The bowl-shaped vanes also include a closed distal end and an opened proximal end wherein the open proximal end is configured to receive flushing water. The proximal surface 205 defines a hollow for capturing flushing water. The water capture element 203 may include more than one pair of vanes 204, for example, the water capture element 203 may include two pairs of opposed generally bowl-shaped vanes 204.

In FIGS. 58a and 58b, the drainage member 210 includes a stem 212 and a urine drainage passageway 218. The drainage member 210 also includes water capture element 213 having one or more generally—cup shaped vanes 214. In this embodiment, the vanes 204 have a generally cylindrical configuration. The interior of each of the vanes 214 defines a proximal surface 215 configured to contact flushing water so that the force of the flushing water impinges on the surface 215. The cup-shaped vanes 214 also include a closed distal end and an opened proximal end wherein the open proximal end is configured to receive flushing water. The proximal surface 215 defines a hollow for capturing flushing water. While the illustrated embodiment includes three vanes 214, in other embodiments, the water capture element 213 could include more or less than three vanes 214.

Referring to FIGS. 59a and 59b, the drainage member 220 includes a stem 222 and a urine drainage passageway 228. The drainage member 220 also includes a generally mushroom or umbrella shaped water capture element 221 having a generally conical hollow vane 224 which tapers outwardly toward the proximal end 223 of the drainage member 220. The interior of vane 224 includes a distal wall 223 and a sidewall 225 which define a proximal surface 227 configured to contact and capture the force of flushing water. The vane 224 also includes a closed distal end and an opened proximal end wherein the open proximal end is configured to receive flushing water. The proximal surface 227 defines a hollow for capturing flushing water.

FIGS. 60a-61b illustrated drainage members 230, 240 which include a stem 232, 242 and a urine drainage passageway 238, 248. Each of the drainage members 230, 240 also include water capture element 230a, 240a having a generally bulbous-shaped (onion-shaped) vane 234, 244 which defines an inner hollow or cavity 235, 245 open to and facing the proximal end portion 233, 243 of the stem 232, 242. The interior of each of the vanes 234 and 244 includes a distal wall 231, 241 and a sidewall 237, 247 wherein the distal wall and sidewall define a surface 239, 249 for contacting flushing water so that the force of the flushing water impinges on the surface 239, 249. Each of the vanes also includes a closed distal end and, as described above, an opened proximal end wherein the open proximal end is configured to receive flushing water into the cavity 235, 245. In the embodiment shown in FIGS. 61a and 61b, the generally bulbous-shaped vane 244 include apertures 246 therethrough which may increase the surface area contacted by flushing water. The bulbous design of the vanes may assist in the catheter orientating itself within the water so that the vane is in a position to capture water. For example, if the vane contacts the bottom of the toilet the rounded shape of the vane may assist in standing the vane upright for capturing flushing water.

In FIGS. 62a-65b, similar to previous embodiments, the drainage members include a stem and a urine drainage passageway. The drainage members 250, 260, 270 and 280 each include a water capture element having a helical or spiral vane including a plurality of windings. The windings may have the same pitch or different pitches relative to each other. The vanes may be wound around the stem or extend from the stem. In the embodiment illustrated in FIGS. 62a and 62b, the vane 254 has a generally circular cross-section. In FIGS. 63a and 63b, the vane 264 has a generally rounded triangular cross-section. Turning to FIGS. 64a and 64b, the vane 274 has a generally square cross-section. Optionally, one or more sides 275 of vane 274 may include a groove 277 extending longitudinally along the vane 274. Referring to FIGS. 65a and 65b, in this embodiment, the vane 285 may include a bottom wall 286 located at the distal end portion of the vane 285.

Figure 66:
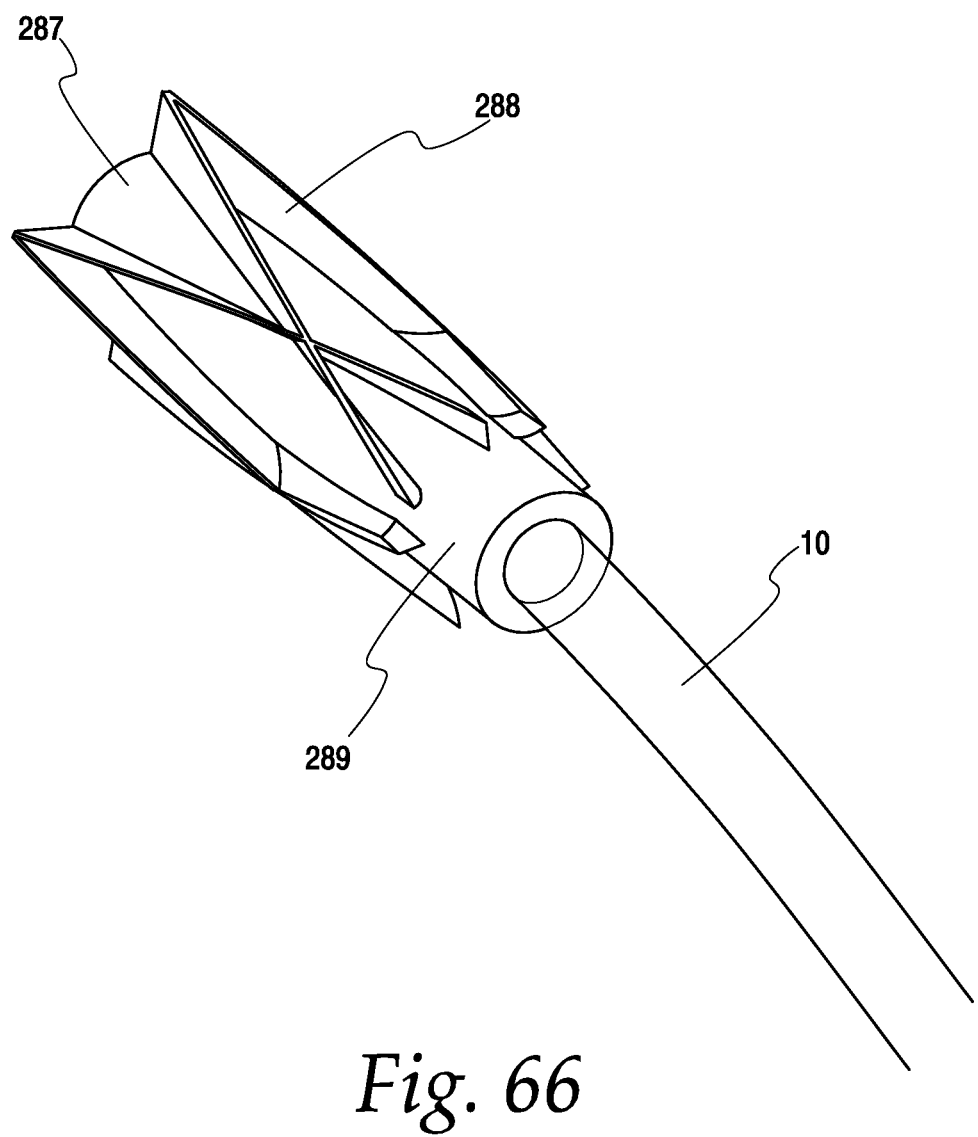
FIG. 66 is a perspective view of another embodiment of a water capture element of the present disclosure.

In FIG. 66, the drainage member 287 includes vanes 288 in the form of fins or raised ridges on the outer surface 289 of the drainage member 287. The ridges may crisscross or otherwise be connected. When the catheter 10 is placed in the toilet for disposal thereof and the toilet is flushed, the water impinges on the fins 287 and fins capture the momentum of the water to propel the catheter 10 down the toilet.

Figure 67:
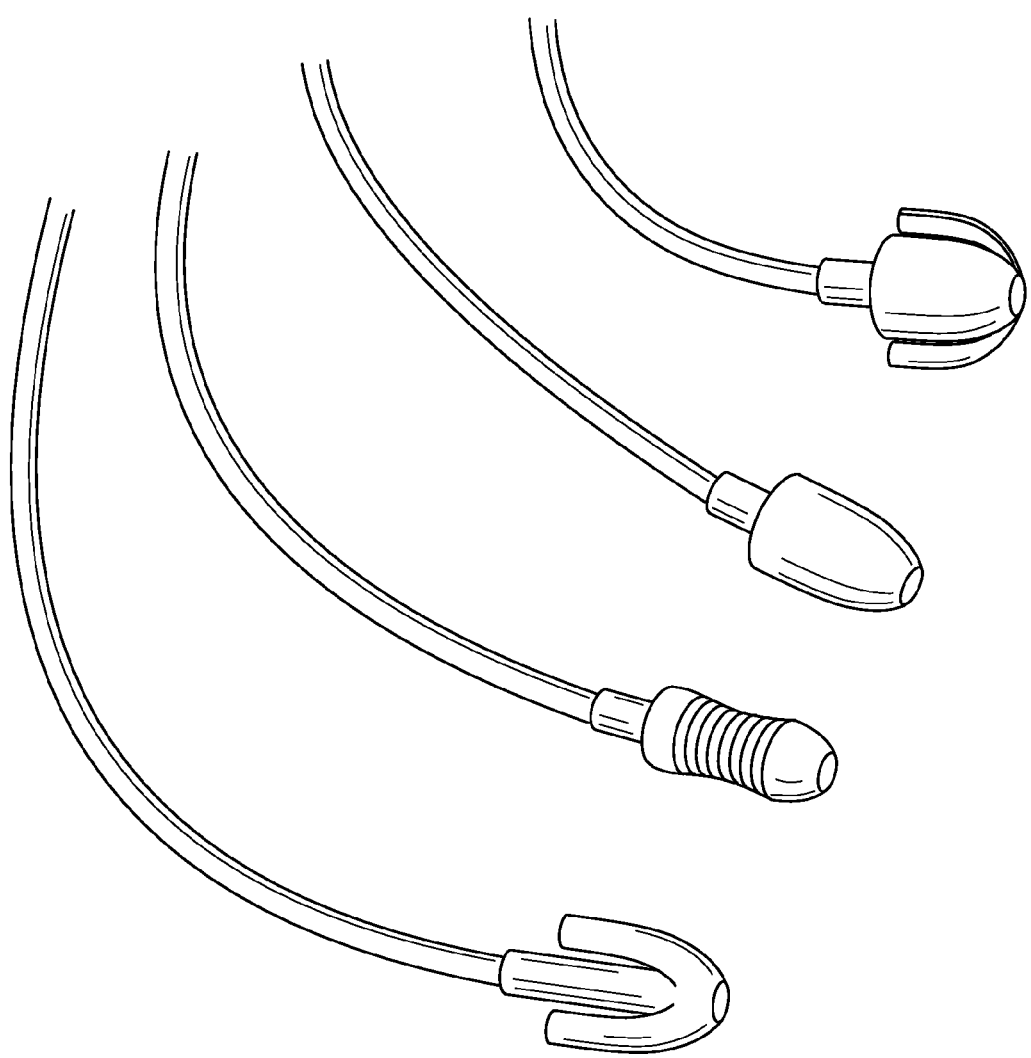
FIG. 67 includes perspective views of various water capture elements of the present disclosure each shown being attached to the distal end portion of a catheter.

FIG. 67 shows exemplary embodiments of catheters which have a drainage member that includes a water capture element associated with the drainage member. While these figures show select exemplary embodiments, it will be understood that any of the above-discussed water capture element and/or drainage members having a water capture element associated therewith may be attached and/or employed with a catheter in a similar manner as shown in these figures.

Additionally, any of the above-mentioned flush enhancing elements, such as the above discussed water capture elements, and other flush enhancing elements disclosed herein may be made in whole in or in-part from an absorbent material that absorbs fluid, such as a sponge or a hydrogel. The absorbent material may be optimized to absorb a selected amount of water. In one embodiment the absorbent material may be optimized to absorb a sufficient amount of water such that the flush enhancing element, including the water therein, has density close to the density of water. When the absorbent material is a porous material, such as a sponge or sponge-like material, the pore size may be optimized so that the material absorbs a selected amount of water. Additionally, when the flush enhancing element is made from a flexible absorbent material, e.g., a sponge, the flush enhancing element may be compacted or compressed for economical packaging.

Furthermore, any of the above-mentioned water capture elements may be configured such that the water capture elements may be movable from a collapsed configuration prior to use to an expanded water momentum capturing configuration just prior to or during flushing down the toilet for disposal thereof.

FIGS. 68a-106 illustrate some non-limiting examples wherein the water capture elements may be movable from a collapsed configuration to an expanded configuration. It will be understood that other embodiments that the water capture elements may only have the expanded configuration and may not be movable between a compact and expanded configuration.

Figure 68A:
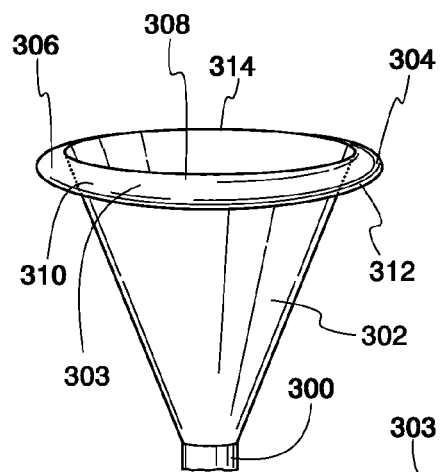
FIG. 68a is a perspective view of another embodiment of a water capture element of the present disclosure shown in a first or collapsed configuration and being associated with a drainage member at the distal end of a catheter.
Figure 68B:
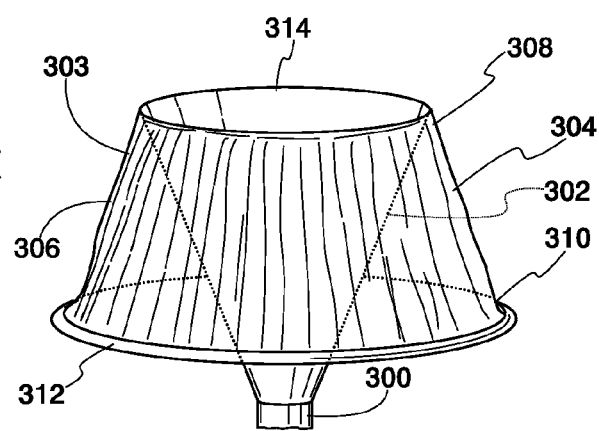
FIG. 68b is a perspective view of the water capture element of FIG. 68a shown a second or expanded configuration.

Referring to FIGS. 68a and 68b, the catheter 300 may include a drainage member 302 having a water capture element 303 attached thereto. The water capture element 303 includes a vane 304 in the form of a sheath or film 306 that may be made from a polymer or foil. The sheath 306 includes a first end 308 that is attached to the periphery of the drainage member 302 and a second end 310 that is attached to a gripping member 312, such as the illustrated ring-shaped member. In the illustrated embodiment, the vane 304 is attached to the distal end 314 of the drainage member 302. In other embodiments, the vane 304 may be attached at any location along the drainage member 302 or the length of the catheter 300.

Referring to FIG. 68a, during urine drainage and prior to disposal within the toilet, the vane 304 is in the first or collapsed configuration. In the first configuration, the sheath 306 may be bunched or folded around the drainage member 302. The vane 304 may be retained in the first configuration by, for example, an adhesive or adhesive tape or by friction. In other embodiments, the sheath 306 may be rolled about the gripping member 312.

Prior to disposal by placement in the toilet, the vane 304 is moved into the second or expanded configuration shown in FIG. 68b. To move the vane 304 into the expanded configuration, the user grasps the gripping member 312 and moves it proximally toward the proximal end of the catheter to unfold, unbunch or unroll the sheath 306. The sheath 306 at least partially surrounds the drainage member 302 and/or catheter 300 to create a water capture space therebetween that captures flushing water to propel the catheter 300 down the toilet and, preferably, through the trapway/U-bend of a sewer pipe.

Figure 69A:
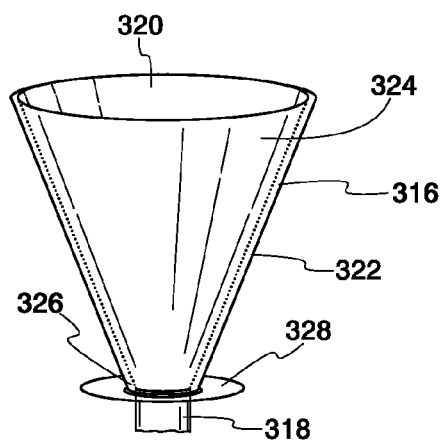
FIG. 69a is a perspective view of another embodiment of a water capture element of the present disclosure shown in a first or collapsed configuration and being associated with a drainage member at the distal end portion of a catheter.
Figure 69B:
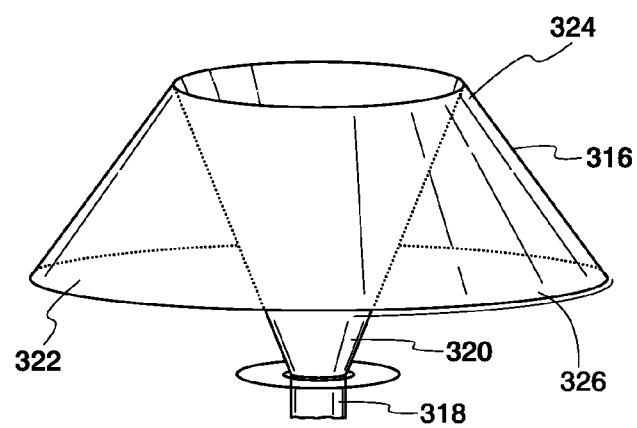
FIG. 69b is a perspective view of the drainage member of FIG. 69a shown with the water capture element in a second or expanded configuration.

FIGS. 69a and 69b illustrate another embodiment of water capture element having a vane 316 that is movable from a collapsed configuration to an expanded configuration. The catheter 318 may include a drainage member 320 to which vane 316 is attached. The vane 316 may include a sheath or film 322 that may be made from a polymer or foil. The sheath 322 is biased or has an inherent tendency to move toward the expanded configuration illustrated in FIG. 69b. The sheath 322 includes a first end 324 that is attached to the periphery of the drainage member 320 and a second free end 326 (FIG. 69b). In other embodiments, the sheath 322 may be attached at any location along the drainage member 320 or the length of the catheter 318.

As illustrated in FIG. 69a, the vane 316 is held or retained in the collapsed configuration by a locking member 328. In the illustrated embodiment, the locking member 328 is a ring-shaped annulet that is placed over the free end 326 of the sheath 322 which annulet captures or holds the free end 326 between the inner rim of the annulet and the drainage member and/or the catheter, thereby holding the vane 316 in the collapsed configuration until just prior to disposal. In another embodiment, the vane 316 may be held in the collapsed configuration by an adhesive or a removable band.

Prior to disposal of the catheter by placement in the toilet, the vane 316 is moved into the second or expanded configuration shown in FIG. 69b. To move the vane 316 into the expanded configuration, the user disengages locking member 328 from the free end 326 of sheath 322. In the illustrated embodiment, the user moves locking member 328 toward the proximal end of the catheter 318 to release the free end 326 of sheath 322. The sheath 322 being biased or having a natural tendency to move toward the expanded configuration transitions from the collapsed configuration to the expanded configuration.

Figures 70A, 70B:
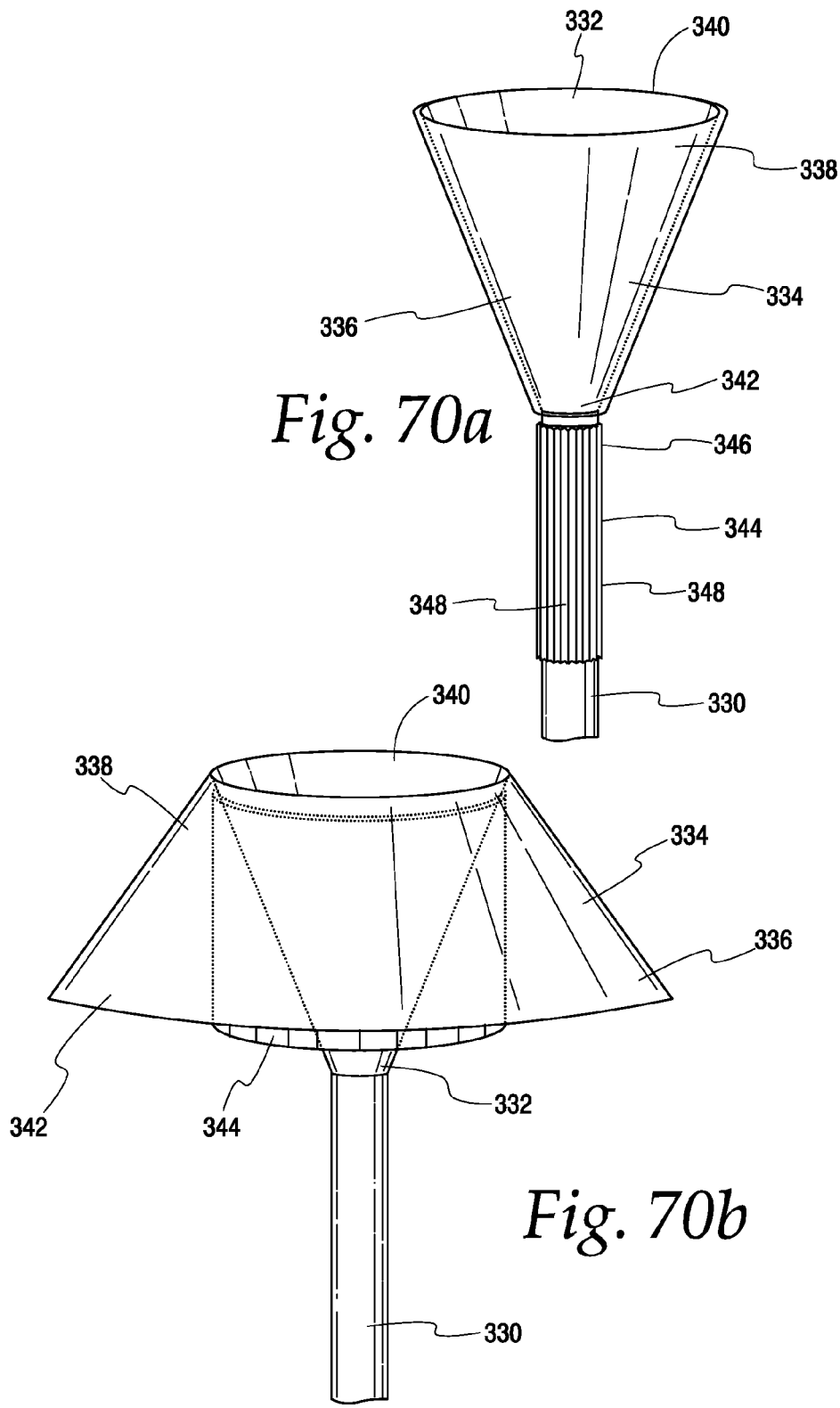
FIG. 70a is a perspective view of another embodiment of a water capture element of the present disclosure shown in a first or collapsed configuration and associated with a drainage member at the distal end of a catheter.
FIG. 70b is a perspective view of the water capture element of FIG. 69a shown in a second or expanded configuration.

Turning to FIGS. 70a and 70b, the catheter 330 includes a drainage member 332 having a water capture element attached thereto. The water capture element includes a vane 334 that may be formed of a sheath or film 336, such as a polymer sheath or foil. The vane 334 has a collapsed configuration shown in FIG. 70a and is movable to an expanded configuration shown in FIG. 70b. Similar to the previous embodiment, the sheath 336 may include a first distal end 338 attached around the periphery of the distal end 340 of the drainage member 332 and a second proximal free end 342. The sheath 336 at least partially surrounds the drainage member and/or funnel. In other embodiments, the vane 334 may be attached at any location along the drainage member 332 or the length of the catheter 330.

The catheter 330 includes an actuation member 344 that is manipulated to deploy the vane 334 from the collapsed configuration to the expanded configuration. In the illustrated embodiment, the actuation member 344 is a tube-like sleeve that surrounds the distal end portion of the catheter 330 and/or the drainage member 332. To deploy the vane 334 from the collapsed configuration to the expanded configuration, the actuation member 344 is manipulated, e.g., moved or slid distally toward the distal end 340 of drainage member 332. As the distal end portion 346 of the actuation member 344 is moved or slid proximally along the drainage member 332, it moves under the free end 342 of the sheath 336 and forces the vane 334 into the expanded configuration similar to the opening of an umbrella (FIG. 70b).

In the illustrated embodiment, the actuation member 344 is radially expandable to accommodate being slid over the tapered outer surface of drainage member 332. The actuation member 344 may include folds 348 which unfold as the actuation member 344 is slid over the drainage member 332.

Figure 71:
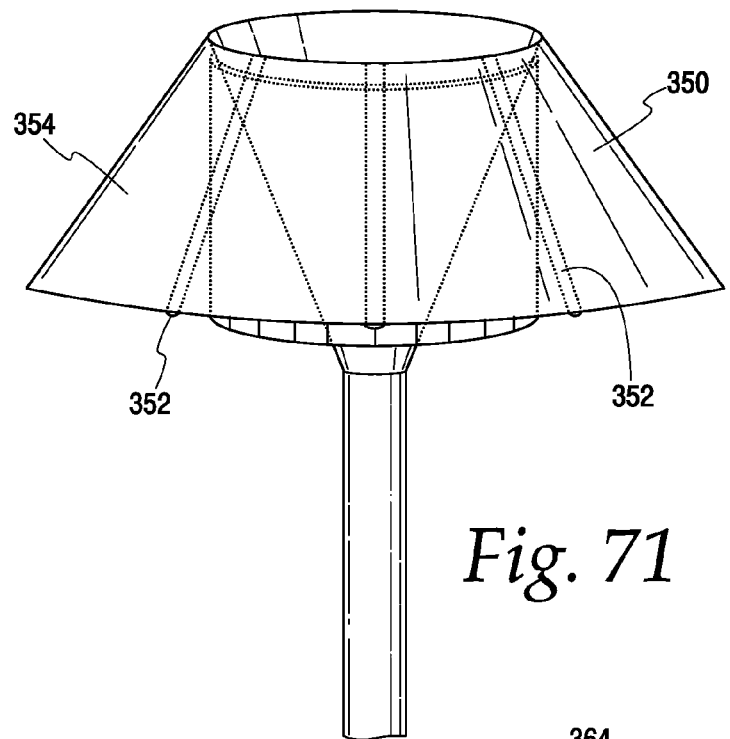
FIG. 71 is a perspective of another embodiment of a water capture element of the present disclosure shown in association with a drainage member.

Referring to FIG. 71 the vane 350 may include a sheath 354 that has ribs 352 which extend along the inner and/or outer surfaces of the sheath 354. The ribs 352 may provide support to the sheath material and/or may assist with moving the vane 350 into the expanded configuration. Such ribs 352 may, optionally, be included in the embodiments shown in FIGS. 68a-70b. The ribs 352 may also serve as biasing members which bias the vane towards the collapsed or expanded configuration.

Figure 72A:
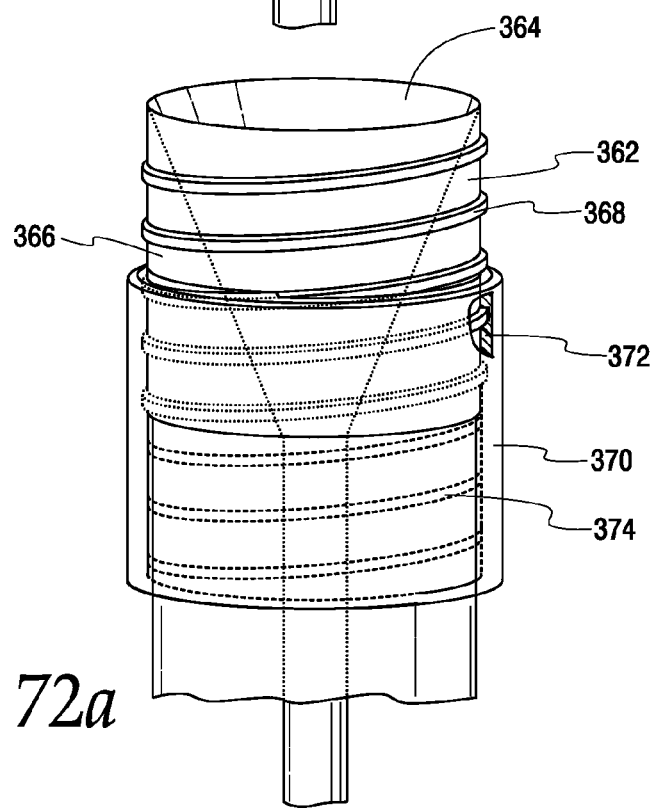
FIG. 72a is perspective view of an actuator for moving a water capture element from a collapsed configuration to an expanded configuration wherein the actuator is associated with a drainage member.
Figure 72B:
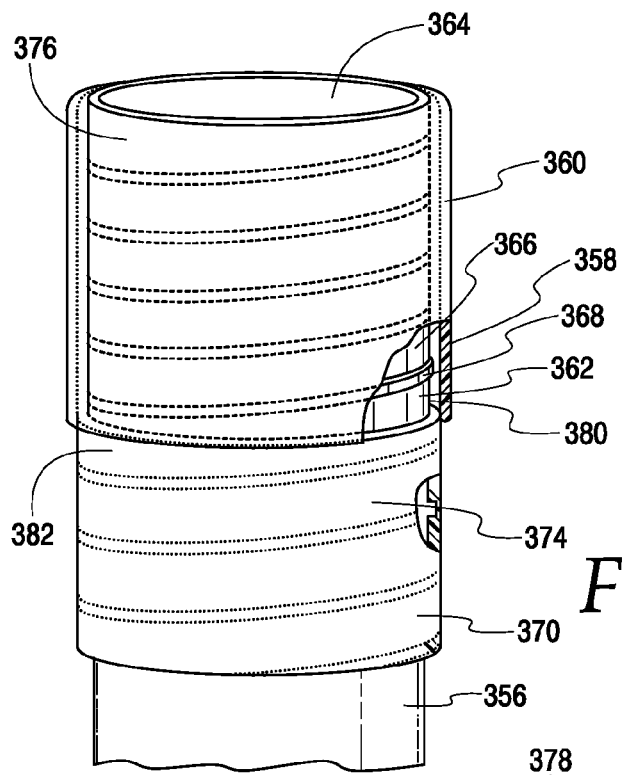
FIG. 72b is a perspective view of one embodiment of a water capture element of the present disclosure shown a first or collapsed configuration.
Figure 72C:
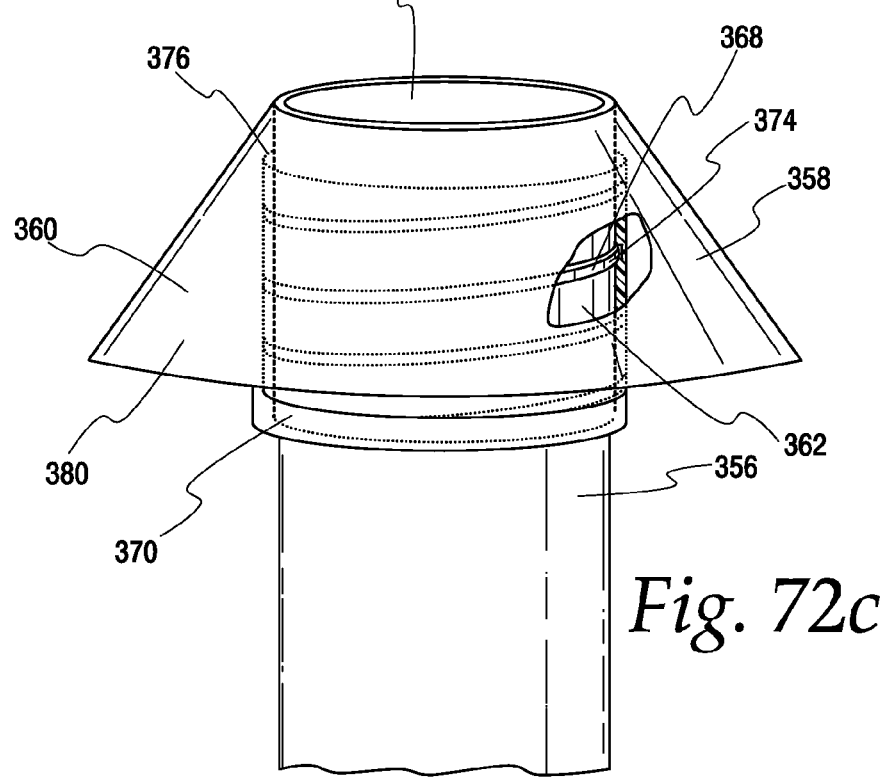
FIG. 72c is a perspective view of the water capture element of FIG. 72b shown in a second or expanded configuration.

Turning to FIGS. 72a-72b, the catheter 356 includes a water capture element having a vane 358 that is movable from a collapsed configuration shown in FIG. 72b to an expanded configuration shown in FIG. 72c. The vane 358 includes a sheath or film 360 that may be made from a polymer or a foil. Catheter 356 is shown in FIG. 72a without vane 358. The catheter 356 includes a drainage member 362 that may be a generally cylindrical tube having a tapered funnel-like inner surface 364 forming a passageway for urine drainage. The outer surface 366 of the drainage member 362 includes a helical thread 368 extending around the outer surface 366 of the drainage member 362. The catheter 356 also includes an actuation member 370, which may be, for example, a generally cylindrical sleeve that surrounds the proximal portion of the drainage member 362 when the vane 358 is in the collapsed configuration. The actuation member 370 has an inner surface 372 that includes a thread 374 which is commentary to and mates with the thread 368 on the outer surface 366 of the drainage member 362. When the actuation member 370 and drainage member 362 are moved rotatably relative to one another, the actuation member 370 moves axially along the drainage member 362 in a distal direction.

Referring to FIGS. 72b and 72c, the sheath 360 may include a distal end 376 attached around the periphery of the distal end 378 of the drainage member 362 and a proximal free end 380. The sheath 360 at least partially surrounds the drainage member 362. In other embodiments, the vane 358 may be attached at any location along the drainage member 362 or the length of the catheter 356. To move the vane 358 from the collapsed configuration to the expanded configuration, the actuation member 370 and drainage member 362 are rotated relative to one another so that the actuation member 370 moves in a distal direction along the drainage member 362. As the distal end portion 382 of the actuation member 370 is moved distally along the drainage member 362, it moves under the free end 380 of the sheath 360 and forces the vane 358 into the expanded configuration similar to the opening of an umbrella.

FIGS. 73-82 illustrate embodiments of water capture elements that may be formed from a rigid material wherein the water capture element includes areas of reduced material to create points of flexure in the material. This allows the water capture element to be biased to the expanded configuration and restrained by a restraint into a compacted configuration. The restraint may be a band, the walls of a package, an adhesive or tackiness of the material. The water capture element also may be biased to the expanded configuration by being made of a shape memory material or by biasing members, such as a spring member. Prior to disposal of the catheter, the user removes the restraint to allow the water capture element to move back into the expanded configuration. In other embodiments, the water capture element is biased to a compact configuration and moved into the expanded configuration by an activator.

Figure 74:
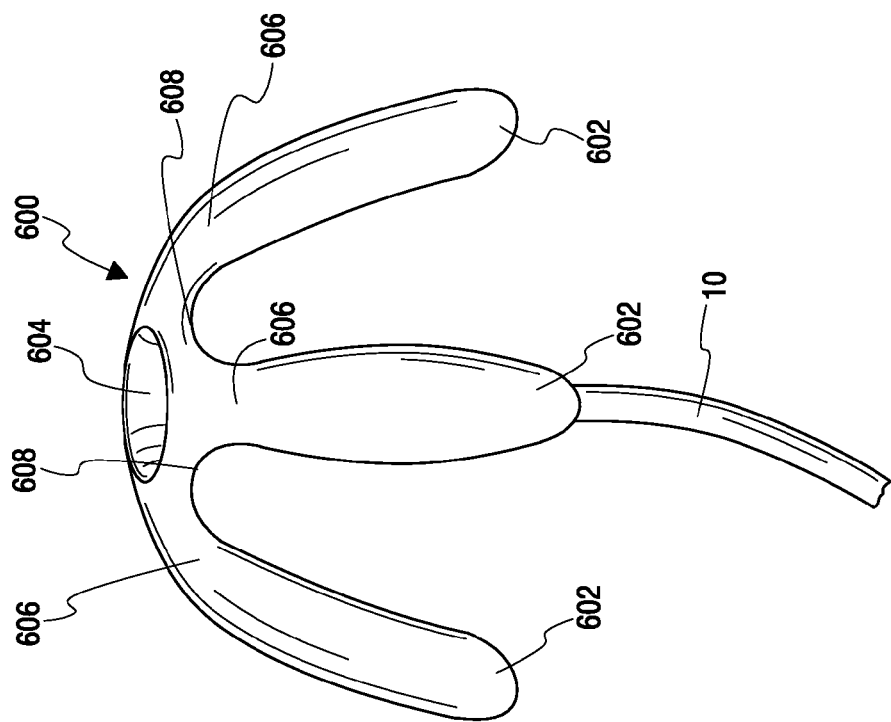
FIG. 74 is a perspective view of the water capture element of FIG. 73 shown in a second or expanded configuration.

Referring to FIG. 74, the catheter 10 includes a water capture element 600 having a plurality of vanes 602 that extend outwardly from the drainage member 604. The vanes 602 have a reduced thickness at a portions 606 at or near the roots 608 of the vanes 602. The reduce thickness portion 606 provides an area of flexure that allows the vanes 602 to be moved inward toward the catheter 10 upon application of force, thereby placing the water capture element 600 into a compact configuration.

Figure 73:
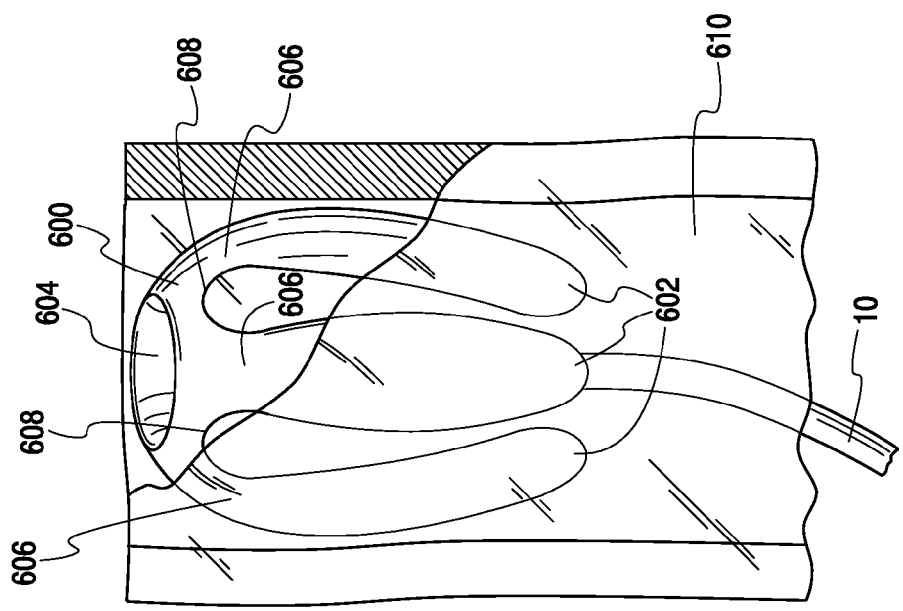
FIG. 73 is a perspective view of another embodiment of a water capture element of the present disclosure shown in a first or collapsed configuration within a package.

In this embodiment, the water capture element 600 has an initial or natural expanded configuration, as shown in FIG. 74. Turning to FIG. 73, the vanes 602 of the water capture element 600 may be moved inward toward the catheter 10 to place the water capture element 600 in a compact configuration. When the catheter is placed in the package 610, the package acts as a restraint that restrains the water capture element 600 in the compact configuration. This allows for a more compact packaging of the water capture element 600. When the catheter 10 is taken out of the package 610 the vanes 602 return to the expanded configuration, as shown in FIG. 74.

Figure 75:
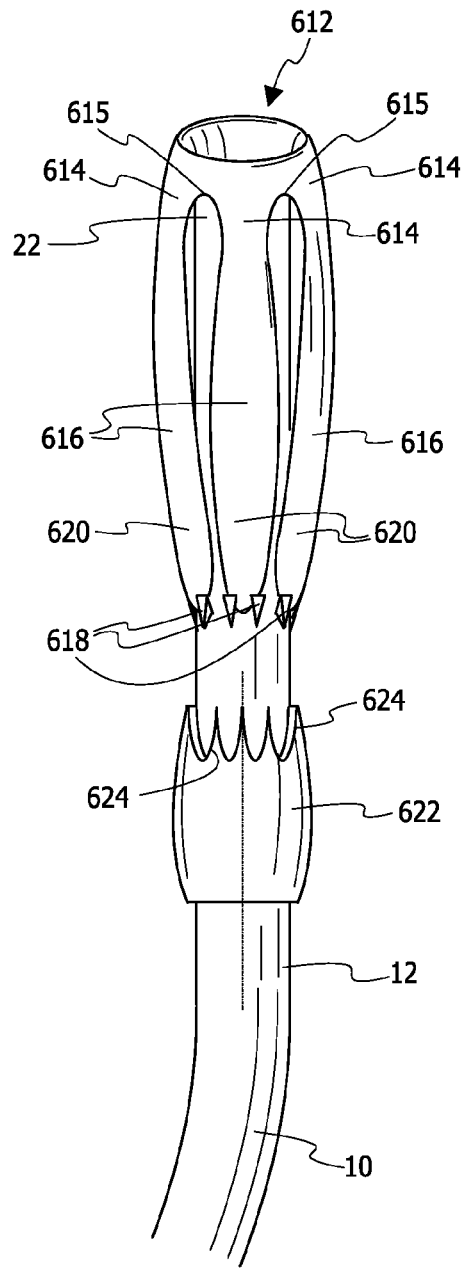
FIG. 75 is a perspective view of another embodiment of a water capture element of the present disclosure shown in a first or collapsed configuration.
Figure 76:
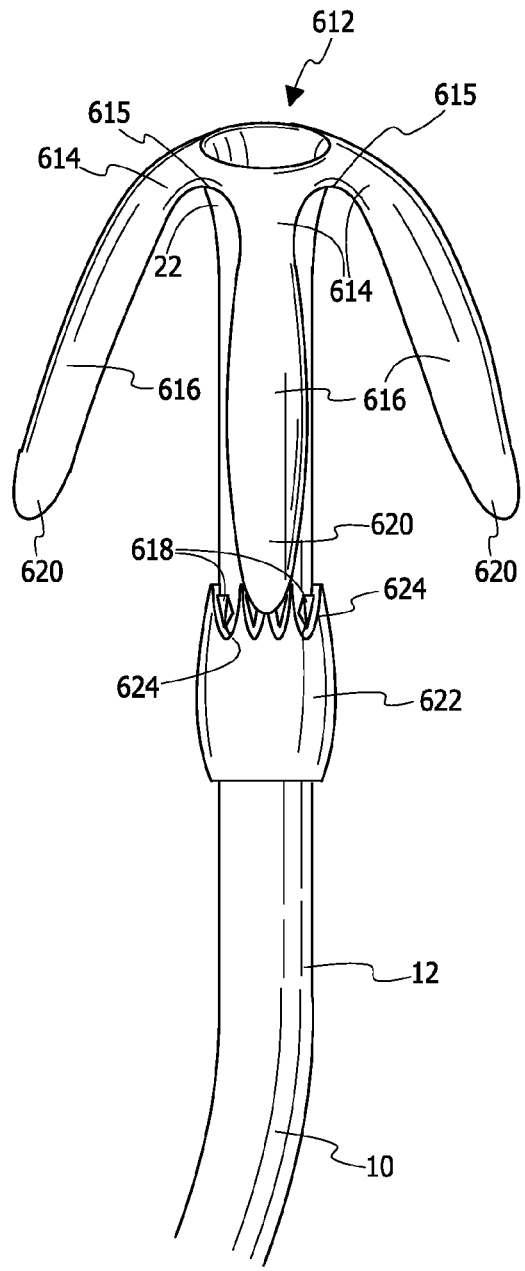
FIG. 76 is a perspective view of the water capture element of FIG. 75 shown in a second or expanded configuration.

Turning to FIGS. 75 and 76, there is shown another embodiment of a water capture element 612. Similar to the water capture element 600, water capture element 612 includes areas 614 of reduced material near the root 615 of vanes 616. The areas 614 of reduced material allow the vanes 616 to be moved from an expanded configuration to a compact configuration. Referring to FIG. 76, the water capture element 612 has an initial or natural expanded configuration. As shown in FIG. 75, the vanes 616 may be moved into and restrained in a compact configuration. In the illustrated embodiment, the catheter 10 includes a plurality of clips 618 mounted to and spaced about the catheter shaft 12 or drainage member 22. The proximal free ends 620 of the vanes 616 are tucked under the clips 618 to restrain the vanes 616 in the compact configuration. The catheter 10 also includes an actuator 622 which may be a cuff surrounding the catheter shaft 12. In this embodiment, the actuator 622 may also serve as a catheter gripping aid which the user may use to handle the catheter 10. The actuator 622 includes projections 624 which may be positioned in the space between the clips 618 when the actuator 622 is slid distally along the catheter shaft 12 toward the clips 618. The projections 624 contact and push the vanes 616 out from under the clips 618. Once the vanes 616 are released, the water capture element 612 returns to its expanded configuration.

Figure 77:
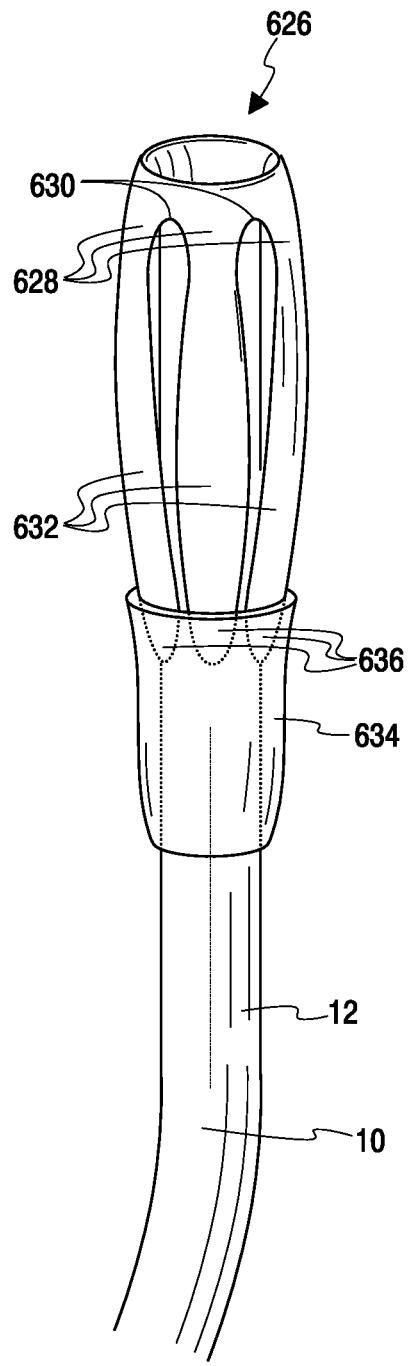
FIG. 77 is a perspective view of another embodiment of a water capture element of the present disclosure shown in a first or collapsed configuration.
Figure 78:
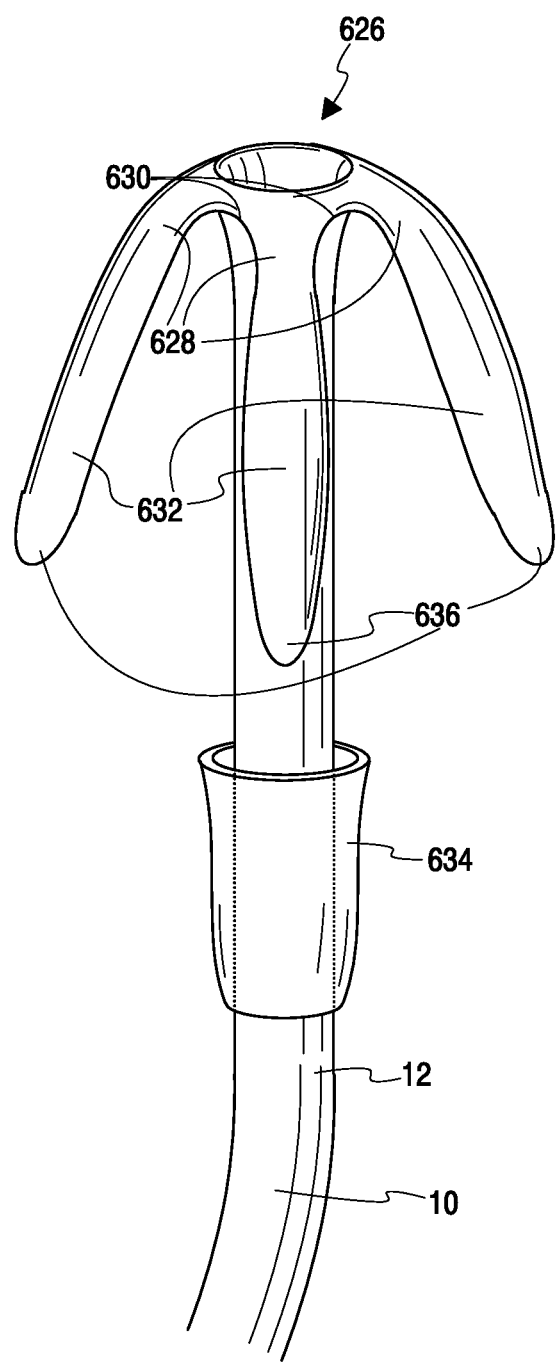
FIG. 78 is a perspective view of the water capture element of FIG. 77 shown in a second or expanded configuration.

Turning to FIGS. 77 and 78, there is shown another embodiment of a water capture element 626. Similar to the water capture element 600, water capture element 626 includes areas 628 of reduced material near the root 630 of vanes 632. The areas 628 of reduced material allow the vanes 632 to be moved from an expanded configuration to a compact configuration. Referring to FIG. 78, the water capture element 626 has an initial or natural expanded configuration. As shown in FIG. 77, the vanes 632 may be moved into and restrained in a compact configuration. In the illustrated embodiment, the catheter 10 includes a cuff 634 that surround the catheter shaft 12. The proximal free ends 636 of the vanes 632 are tucked under the cuff 634 to restrain the vanes 616 in the compact configuration. The cuff 634 services as an actuator that is moved to allow the water capture element 626 to move into the expanded configuration. The cuff 634 may also serve as a catheter gripping aid which the user may use to handle the catheter. When the cuff 634 is moved proximally along the catheter shaft 12, the vanes 632 are released and the water capture element 626 returns to its expanded configuration.

Figure 79:
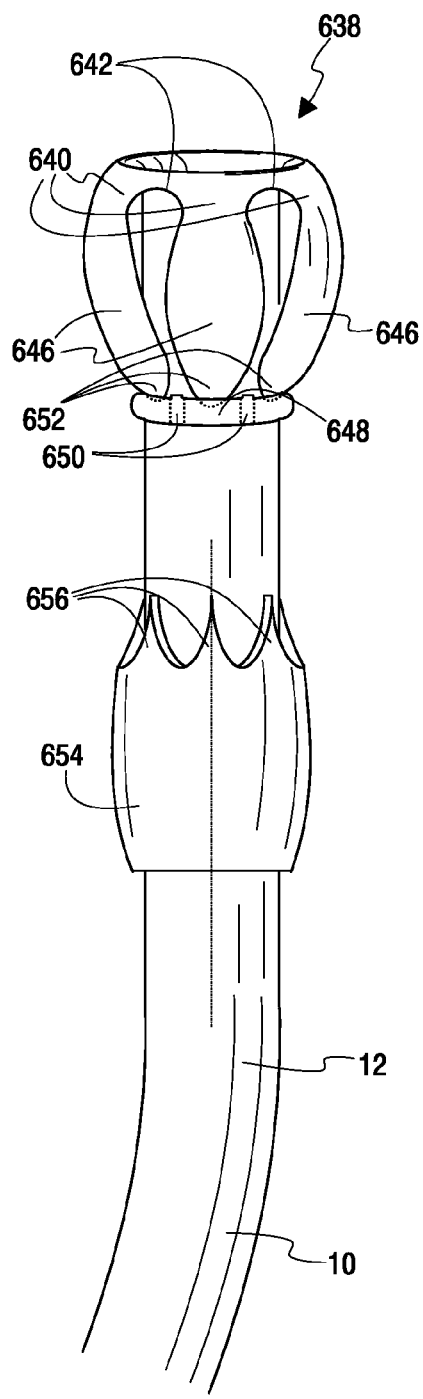
FIG. 79 is a perspective view of another embodiment of a water capture element of the present disclosure shown in a first or collapsed configuration.
Figure 80:
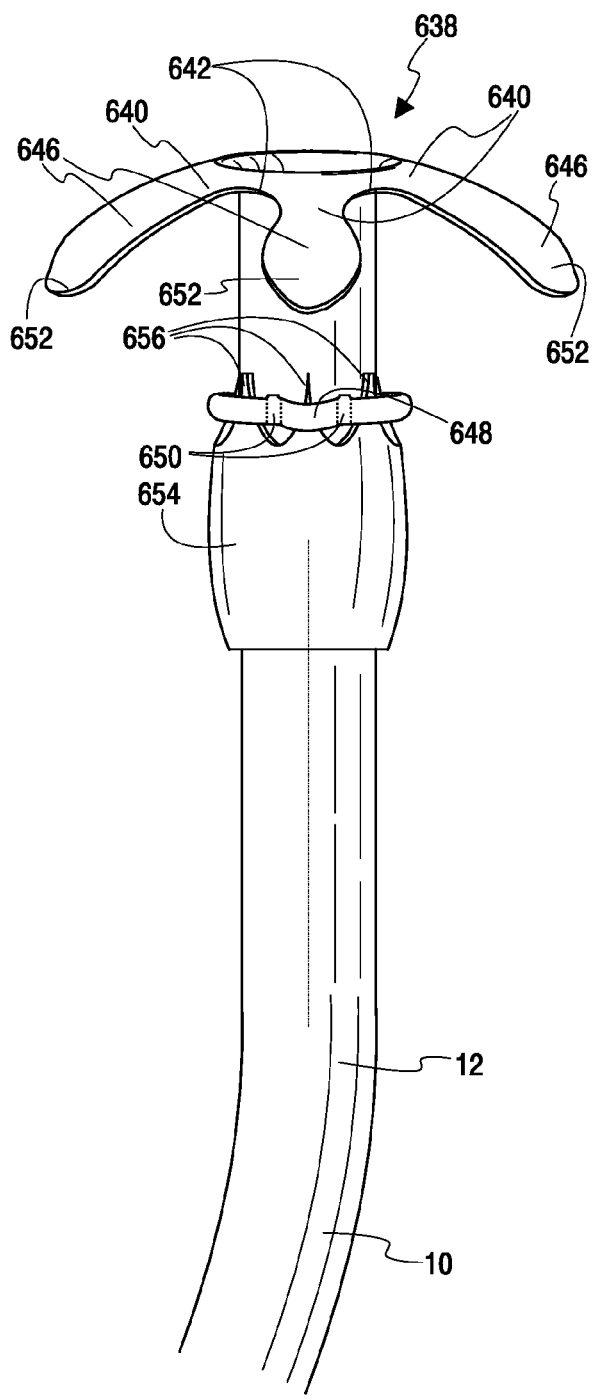
FIG. 80 is a perspective view of the water capture element of FIG. 79 shown in a second or expanded configuration.

Turning to FIGS. 79 and 80, there is shown another embodiment of a water capture element 638. Similar to the water capture element 600, water capture element 638 includes areas 640 of reduced material near the root 642 of vanes 646. The areas 640 of reduced material allow the vanes 646 to be moved from an expanded configuration to a compact configuration. Referring to FIG. 80, the water capture element 638 has an initial or natural expanded configuration. As shown if FIG. 79, the vanes 646 may be moved into and restrained in a compact configuration. In the illustrated embodiment, the catheter 10 includes a ring 648 that is mounted to catheter shaft 12 or drainage member 22. The ring 648 is mounted at spaced apart mounting locations 650. The proximal free ends 652 of the vanes 646 are tucked under ring 648 to restrain the vanes 646 in the compact configuration. The catheter 10 also includes an actuator 654 which may be a cuff surrounding the catheter 10. In this embodiment, the actuator 654 may also serve as a catheter gripping aid which the user may use to handle the catheter. The actuator 654 includes projections 656 which may be positioned in the space between the mounting locations 650 when the actuator 656 is slid distally along the catheter shaft 12 toward the rings 648. The projections 656 contact and push the vanes 646 out from under the ring 646. Once the vanes 646 are released, the water capture element 638 returns to its expanded configuration.

Figure 81:
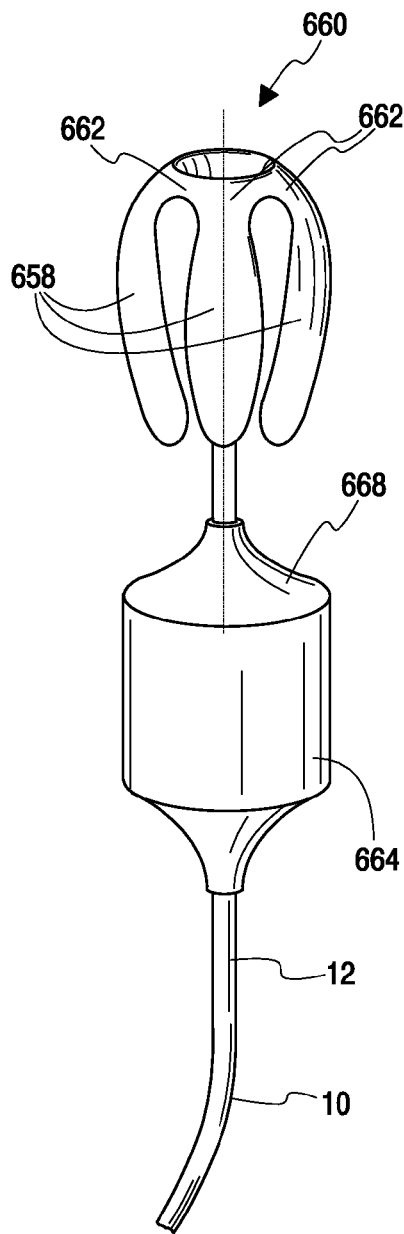
FIG. 81 is a perspective view of another embodiment of a water capture element of the present disclosure shown in a first or collapsed configuration.
Figure 82:
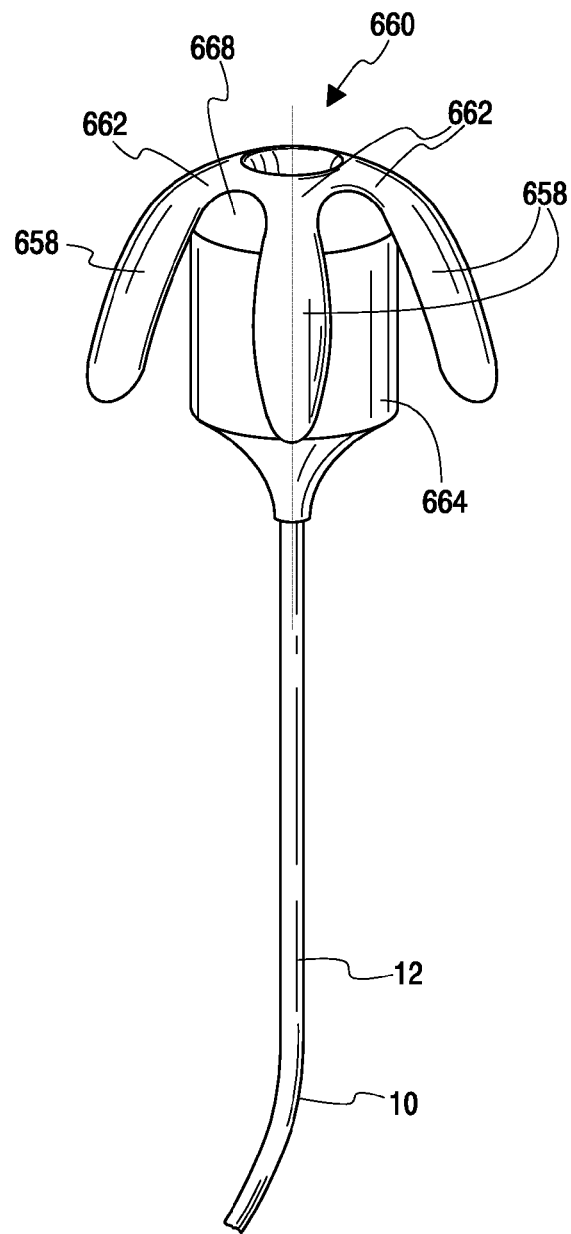
FIG. 82 is a perspective view of the water capture element of FIG. 81 shown in a second or expanded configuration.

In FIGS. 81 and 82, the vanes 658 of the water capture element 660 having an initial compact configuration in which the vanes 658 are biased inward toward the catheter 10. Similar to the previous embodiments, the water capture element includes areas 662 of reduced material that allow the vanes to flex between the compact configuration and the expanded configuration. The catheter 10 includes an actuator 664 which may be slid along the catheter shaft 12 and/or the drainage member. The actuator 664 is slid distally along the catheter shaft 12 and under the vanes 658 of the water capture element 660 to extend the vanes 658 outwardly into the second expanded configuration shown in FIG. 82. The outer surface 668 of the actuator 664 can be sloped or tapered so as to serve as a cam that pushes the vanes 658 outwardly. Furthermore, the actuator 664 also may function as a catheter gripping aid that the user may grip to assist in handling the catheter during use.

Figure 82A:
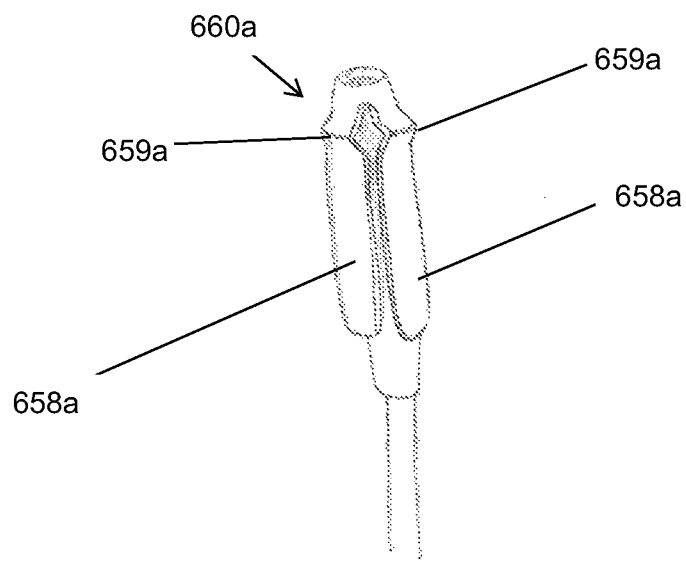
FIG. 82a is a perspective view of another embodiment of a water capture element of the present disclosure shown in a first or collapsed configuration.
Figure 82B:
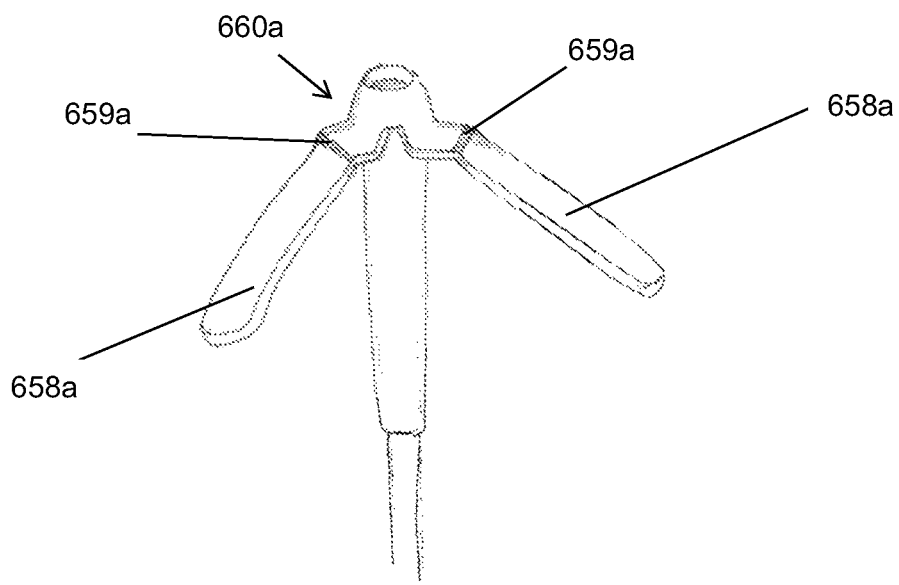
FIG. 82b is a perspective view of the water capture element of FIG. 82a shown in a second or expanded configuration.

In FIGS. 82a and 82b, the vanes 658a of the water capture element 660a having an initial compact configuration in which the vanes 658 are biased inward toward the catheter. In this embodiment, the vanes 658a include a hinge 659a. Hinge 659a may be a living hinge which can be formed during molding of the water capture element 660a. The hinge 659a may be a "butterfly hinge" similar to the hinge on a cap of shampoo or ketchup bottle. The user may move the vanes 658a from the compact configuration to the expanded configuration by flicking the vanes 658a outward.

Flicking the vanes 658*a* will cause the vanes to move about the hinge 659*a*, which may be in a "snapping-like" action similar to that of the caps on shampoo or ketchup bottles. In other embodiments, the catheter could include an actuator which may be slid under the vanes 658*a* to move the vanes into the expanded configuration. In yet other embodiments, the hinges 659*a* may be designed such that the force of flushing water moves the vanes 658*a* to the expanded configuration. Such living hinge may be incorporated into any of the embodiments wherein the vanes move between a compact and expanded configuration. For example, the embodiments of the water capture elements shown in FIGS. 73-86 may include a living hinge.

Figures 83, 84:
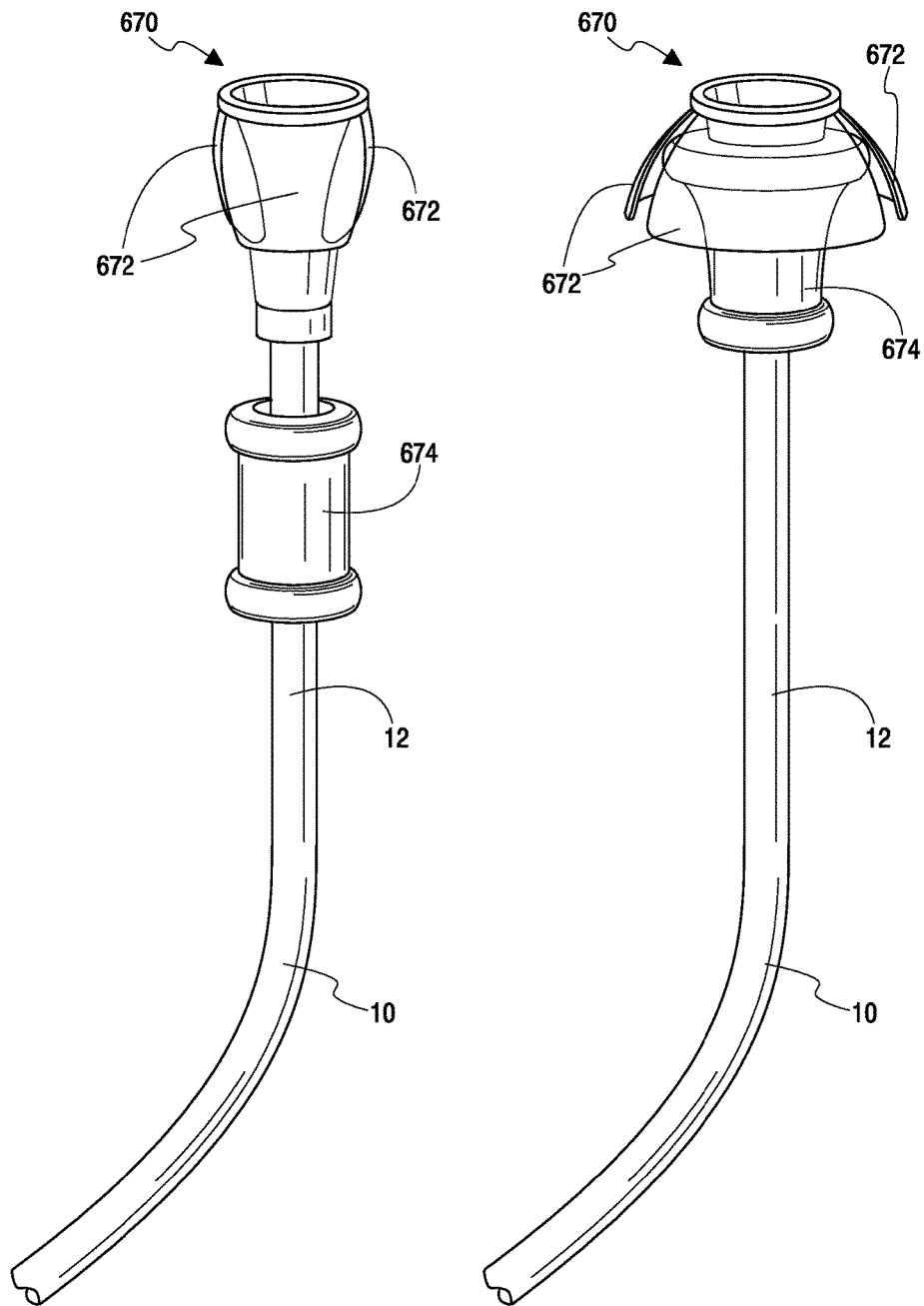
FIG. 83 is a perspective view of another embodiment of a water capture element of the present disclosure shown in a first or collapsed configuration.
FIG. 84 is a perspective view of the water capture element of FIG. 83 shown in a second or expanded configuration.

In FIGS. 83 and 84, a water capture element 670 includes a plurality of vanes 672 that are biased towards the compact configuration shown in the FIG. 83. In the illustrated embodiment, the vanes 672 may be generally tri-angled shaped wherein the tops of each of the triangles are attached to the funnel 22 and the bases are unattached and overlap one another. The vanes may be biased to the compact configuration by shape memory of the material, by compressing of the packaging or by bonding the vanes to each other, the funnel or the catheter. An actuator 674 may be slid distally along the catheter shaft 12 and funnel 22. The actuator 674 is slid under the vanes 672 of the water capture element 670 to move the vanes 672 into the expanded configuration shown in FIG. 84. In this embodiment, the actuator 674 may be made of a stretchable or gel-like material that stretches when it is slid over the tapered surface of the funnel 22 to cause the vanes 672 to move outwardly.

Figure 85:
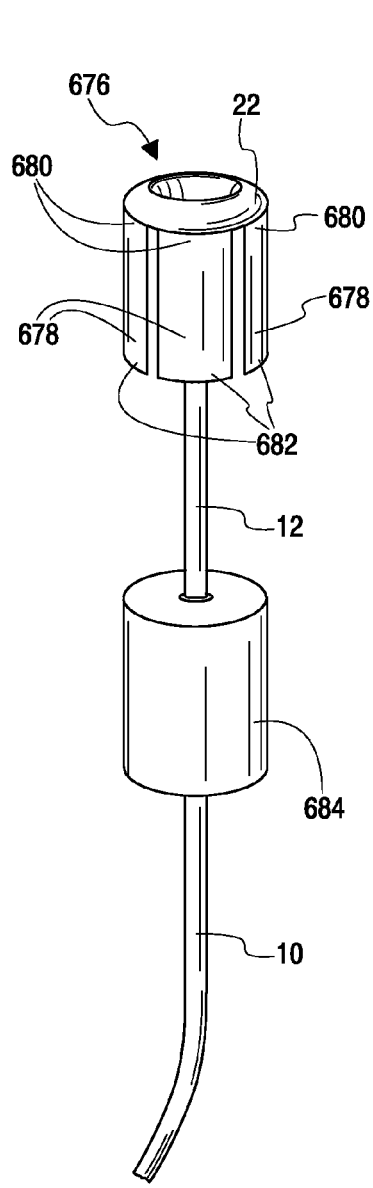
FIG. 85 is a perspective view of another embodiment of a water capture element of the present disclosure shown in a first or collapsed configuration.
Figure 86:
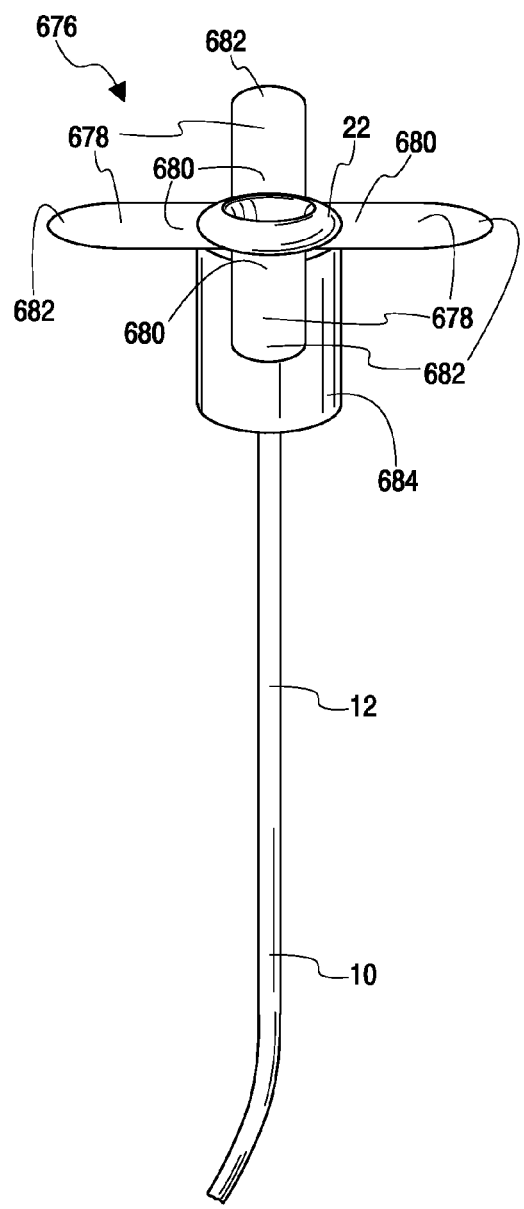
FIG. 86 is a perspective view of the water capture element of FIG. 85 shown in a second or expanded configuration.

In FIGS. 85 and 86, a water capture element 676 includes a plurality of vanes 678 that are biased to the compact configuration shown in FIG. 85. Each of the vanes 678 has a distal end portion 680 attached to the drainage member 22 and a free proximal end portion 682. An actuator 684 may be slid distally along the catheter shaft 12 and/or drainage member 22. The actuator 685 is slide under the free proximal ends 682 of the vanes 678 of the water capture element 676 to move the vanes 678 into the expanded configuration.

FIGS. 87-89 show a gripping aid 686 that may be separated into a plurality of sections to define a water capture element having one or more vanes. Referring to FIGS. 87 and 88, the gripping aid 686 has a proximal end portion 688 and a distal end portion 690. Extending from the distal end portion 690 toward the proximal end portion 688 are one or more separation lines 692. The separation lines 692 may be a weekend section of the material, a reduced section of the material or a perforation. The gripping aid 686 has a generally conical body which tapers outward towards the distal end portion 690. Referring to FIG. 89, the gripping aid 686 may be pushed or slid distally over or in contact with the funnel 22 wherein the force of the gripping aid 686 against the funnel 22 results in the gripping aid 686 separating into different sections 694 along the separation lines 692. The gripping aid 692 defines a water capture element wherein the separated sections 694 define vanes.

In FIGS. 90 and 91, the drainage member 696 defines a water capture element wherein the vanes 698 are in the initial compact configuration shown in FIG. 90. The vanes 698 overlay and conform to the contour of the outer surface 700 of the drainage member 696. The vanes 698 have a free proximal end portion 702. The distal end portion 704 of the vanes 698 is attached to the exterior surface 700 of the drainage member 696. The vanes may 698 be made of a material that softens or becomes flexible when contacted by water, such as a polyvinyl alcohol film. When the user is finished with the catheter and the catheter is placed into toilet water for disposal thereof, the vane 698 come into contact with water and soften or become more flexible. The softened vanes 698 extend outwardly from the funnel 22 under the force of rushing water.

FIGS. 92, 93 and 97-99 disclose gripping aids that have an initial compact configuration in which the gripping aid is used to grip and manipulate the catheter. The gripping aids also have an expanded configuration in which the gripping aid defines a water capture element. Referring to FIGS. 92 and 93, the gripping aid 710 includes first and second end opposed ends 712 and 714 and an intermediate portion 716 therebetween. In the illustrated embodiment, the gripping aid 710 is a generally rectangular sheet or strip of material. The intermediate portion 716 includes a hole 718 therethrough for receiving the catheter shaft 12. The gripping aid 710 is folded so that the first and second ends 712 and 714 are superimposed over one another with the catheter shaft 712 therebetween, as shown in FIG. 92. A water soluble adhesive may be located between the corners and/or between the sides of the first and second ends 712 and 714 to attach the ends 712 and 714 to one another. This maintains the gripping aid 710 in the folded configuration during use. The end edges 720 and 722 of the first and second ends 712 and 714 may be partially secure or completely unattached to allow the catheter shaft 12 to pass therebetween so that the gripping aid 710 may be slid along the catheter.

After the user is finished with the catheter 12, he or she may place it into a toilet for disposal thereof. When in contact with the toilet water, the adhesive dissolves freeing the first and second ends 712 and 714. The gripping aid 710 may then move into the linear configuration shown in FIG. 93 to define a water capture element. The gripping aid 710 may unfold do to the force of moving water or the gripping aid 710 may be biased to the unfolded configuration.

Figure 97:
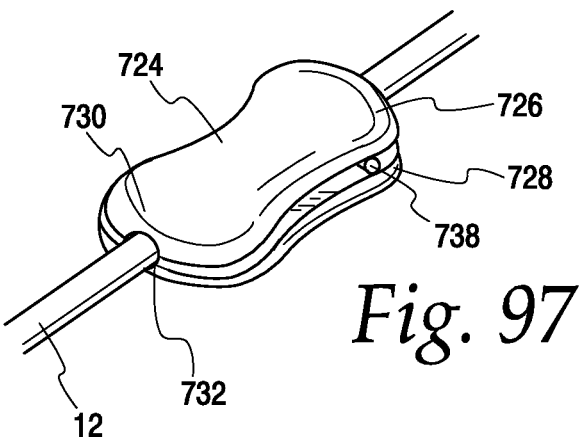
FIG. 97 is a front perspective view of another embodiment of a catheter gripping aid of the present disclosure.
Figure 98:
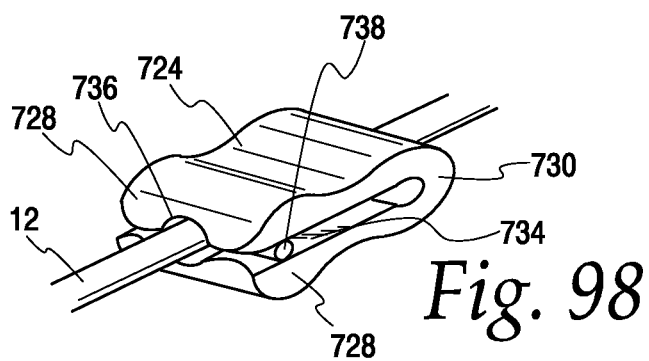
FIG. 98 is a rear perspective view of the catheter gripping aid of FIG. 97.
Figure 99:
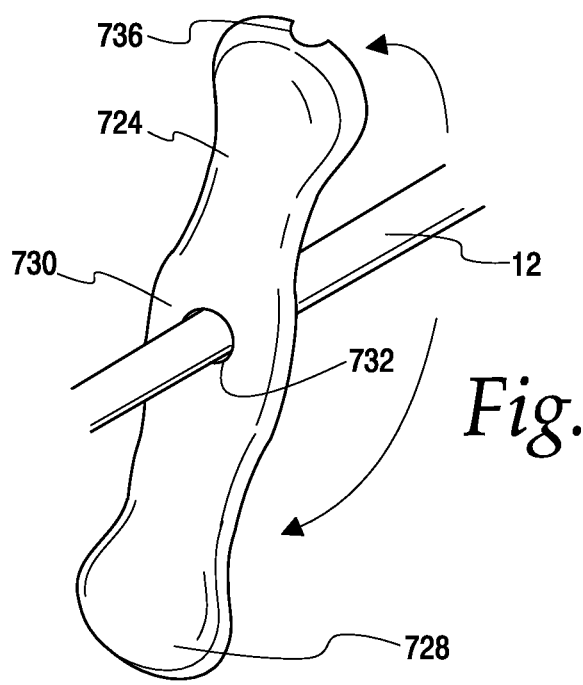
FIG. 99 is a perspective view of the catheter gripping aid of FIG. 97 shown in a second or expanded configuration to define a water capture element.
Figure 112:
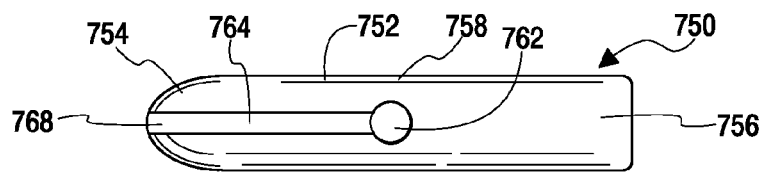
Figure 113:
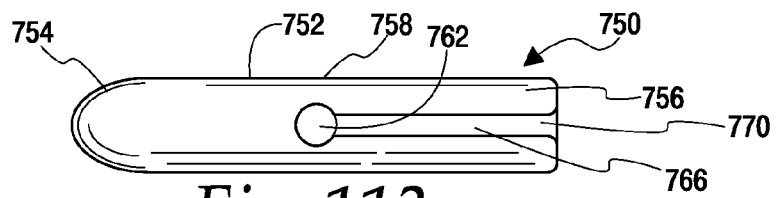
Figure 114:
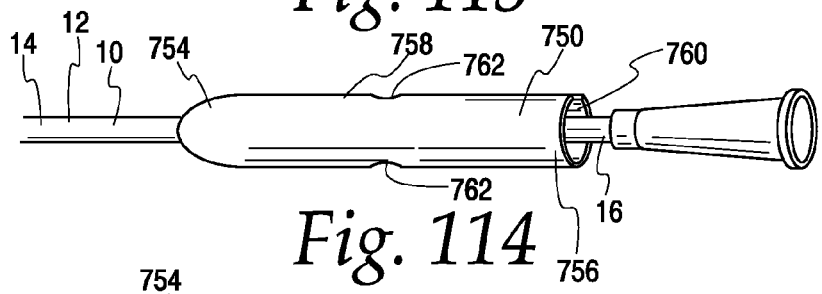

Referring now to FIGS. 97-99, similar to the gripping aid 710 shown in FIGS. 92 and 93, gripping aid 724 includes first and second end opposed ends 726 and 728 and an intermediate portion 730 therebetween. The intermediate portion 730 includes a hole 732 therethrough for receiving the catheter shaft 12. The gripping aid 724 is folded so that the first and second ends 726 and 728 are superimposed over one another with the catheter shaft 12 therebetween. Additionally, the rear surface 734 of the gripping aid 724 may include a channel 736 that receives the catheter shaft 12 and guides the gripping aid 724 therealong when the gripping aid 724 is moved along the catheter shaft 12 (FIG. 98). A water soluble adhesive 738 may be located between the first and second ends 726 and 728 to attach the ends 726 and 728 to one another. This maintains the gripping aid 724 in the folded configuration during use.

After the user is finished with the catheter 10, he or she may place it into a toilet for disposal thereof. When in contact with the toilet water, the adhesive 738 dissolves freeing the first and second ends 726 and 728. The gripping aid 724 may then unfold to define a water capture element. The gripping aid 724 may unfold do to the force of moving water or the gripping aid 724 may be biased to the unfolded configuration.

FIGS. 94-96 illustrate another embodiment of a gripping aid 740. In the embodiment, the gripping aid 740 has a bulbous shaped, hollow compressible body which defines a water capture element when the gripping aid 740 is a compressed state. Referring to FIGS. 95 and 96, when the gripping aid 740 is moved distally and contacted against the funnel 22, the walls 742 of the gripping aid 740 deform.

Under compression, the gripping aid 740 forms a generally mushroom or umbrella shapes configuration, which defines a water capture element.

FIGS. 100-103 show another embodiment of a catheter 400 having a water capture element 402 including an expandable vane 404. In this embodiment, the vane 404 may be made from a material that expands/unfurls when it is wetted or comes into contact with water. For example, the vane 404 may be made from tissue paper, pulp cellulose or a sponge-like material.

Turning to FIG. 100, strips or sheets of tissue paper 406 may be attached to the drainage member 408 to form wings which extend radially from either side of the drainage member 408. Turning to FIG. 101, the sheets 406 may be wetted and wrapped around the drainage member 408. Wetting of the sheets 406 may be done before or after the sheets are wrapped around the drainage member 408. Drainage member 408 having the sheets wrapped thereabout is placed in a mold 410 to mold the sheets 406 into a compact configuration around the drainage member 408. The mold is then placed under high pressure which may be applied by a vice or a dye. The drainage member 408 and sheets 406 molded thereabout are removed from the mold 410 and dried, for example, in an oven. Once dried, the sheets 406 retain their compact shape wrapped around the drainage member 408 as shown in FIG. 102.

Referring to FIG. 103, after using the catheter 400 to drain the bladder, the patient removes the catheter from the patient's body and disposes of the catheter 400 in a toilet 412. When the sheets 406 of the water capture element are contacted by the water in the toilet, the sheets 406 move from the compact configuration to an expanded configuration to define wings which extend outwardly from drainage member 408. When the toilet is flushed, the flushing water contacts the sheets 406 to propel the catheter 400 down the toilet and/or across the trapway/U-bend of the sewer pipe.

FIGS. 104-106a illustrate another embodiment of a water capture element 414 having a plurality of vanes 416 that are movable from a compact configuration to an expanded configuration. The water capture 414 shown in these figures may be a structure or component that is separate from the catheter and attached to the catheter by the user after the catheter has been employed to drain the bladder. In an alternative embodiment, the water capture element 414 may be integral or one-piece with the catheter.

Referring to FIG. 104, the water capture element includes an attachment portion, such as a stem 418, which may for example have a Christmas tree-like configuration. Extending from the distal end 420 of the stem 418 is a plurality of elongated vanes 416. In the embodiment shown, the elongated vanes 416 extend generally parallel to the axis of the stem. As illustrated in FIGS. 105-106a, the vanes 416 are movable from the compact configuration to the expanded configuration. In one embodiment, the vanes 416 are hingedly attached to the distal end portion 420 of the stem 418. In another embodiment, the vanes 416 include a bendable or foldable portion adjacent the distal end portion 420 of the stem. The vanes 416 are movable from the compact configuration to the expanded configuration by bending the vanes 416 so that they extend in a proximal direction and form an umbrella-like configuration.

Referring to FIGS. 106 and 106a, when the user is finished draining the user's bladder and is ready to dispose of the catheter, the user inserts the stem of the water capture element 414 into the drainage member 422 of the catheter 424. In the illustrated embodiment, the Christmas tree-like configuration of the stem 418 forms a friction fit with the drainage member 422 to retain the water capture element within the drainage member. In other embodiments, the water capture element 414 may be secured to the catheter in any suitable manner, including for example, attachment by snap-fit or adhesives.

With the water capture element 414 attached to the drainage member 422 and the vanes 416 in the expanded configuration, the user places the catheter 424 into a toilet for disposal. When disposed in a toilet, the vanes 416 in the expanded configuration are contact by flushing water to propel the catheter 424 down the toilet and/or across a trapway/U-bend of the sewer pipe.

FIGS. 107-111 illustrate water capture elements 426, 428 and 430 that may be attached to the catheter. The water capture elements are formed from a sheet of material, such as a sheet of water disintegratable material and include a hole or aperture 432, 434 and 436 therethrough for passage of the catheter shaft therethrough. As shown in the figures, the water capture elements may have different shapes and sized. The water capture element may be associated with the catheter during the manufacturing process or the user may attach the water capture element to the catheter immediately prior to use or right after use of the catheter.

Referring to FIGS. 107-110, each of the water capture elements 426, 428, 430 include a hole or aperture 432, 434, 436, respectively, therethrough for passage of the shaft of a catheter 438. As illustrated in FIGS. 108, 109 and 110, the shaft of the catheter 438 may be passed through the hole until the water capture element 426, 428, 430 abuts or is adjacent to the drainage member 440.

Water capture elements 426 and 428 have a generally rectangular shape. The main difference between water capture elements 426 and 428 is that water capture element 428 has a curvature which defines a concave proximal surface for capturing water. Referring to FIGS. 110 and 111, the water capture element 430 has a generally cross-shaped configuration with one or more projections 442 extending radially outwardly from aperture 436. As illustrated in FIG. 111, one or more of the projections 442 may include a curvature.

FIGS. 112-121 illustrate other embodiments of gripping aids which may function as a gripping aids when in one orientation about the catheter and may function as a water capture element when placed in a different orientation about the catheter.

Referring to FIGS. 112-116, the gripping aid 750 includes a body 752 having a proximal end portion 754, a distal end portion 756 and an intermediate portion 758 therebetween. The gripping aid 750 also includes a bore or a lumen 760 (FIGS. 114-116) extending therethrough for receiving the catheter shaft 12 and for allowing the gripping aid 750 to move along the catheter shaft 12. As with the previous gripping aid embodiments, the user may grasp the catheter 10 by pinching the gripping aid 750 against the catheter 10 to manipulate the catheter during use.

The intermediate portion 758 of the gripping aid 750 includes a hole 762 therethrough. The gripping aid 750 also includes a pair of slits 764 and 766 in communication with the hole 762. A proximal slit 764 is located on one side of the gripping aid 750 and extends from the proximal opening 768 to the hole 762 in the intermediate portion 758. A distal slit 766 is located on the other side of the gripping aid 750 and extends from the distal opening 770 to the hole 762 in the intermediate portion 758.

Figure 115:
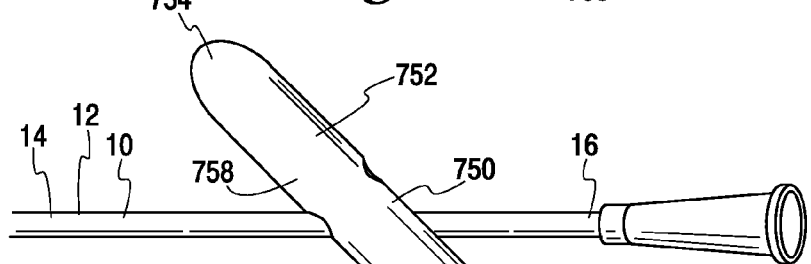
Figure 116:
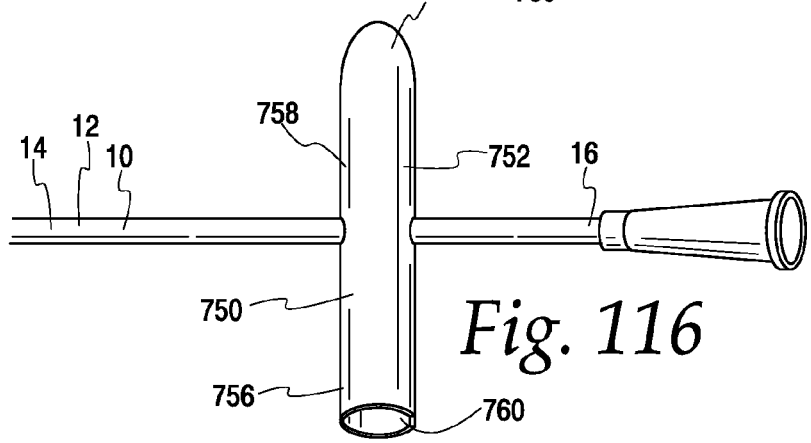

After the user is finished with catheterization, the gripping aid 750 may be reoriented about the catheter shaft 12 so that the elongated axis of the gripping aid 750 extends perpendicular to the elongated axis of the catheter shaft 12, as shown in FIGS. 115 and 116. Referring to FIG. 115, the user turns the catheter 10 relative to the gripping aid 750 so that a proximal portion 14 of the catheter shaft 12 passes through the proximal slit 764 and a distal portion 18 of the catheter shaft 12 passes through the distal slit 766. The gripping aid 750 is rotated relative to the catheter 10 until the catheter shaft 12 is positioned with the hole 762 in the intermediate portion 758. When the gripping aid 750 extends perpendicular to the catheter shaft 12, as shown in FIG. 116, the gripping aid 750 defines a water capture element. When the catheter 10 is flushed down the toilet for disposal thereof, the gripping aid 750 captures the momentum of the flushing water to carry the catheter 10 out of the toilet bowl and into the sewer system.

Turning now to FIGS. 117-121, the gripping aid 772 includes a body 774 having a proximal end portion 776, a distal end portion 778 and an intermediate portion 780 there between. The gripping aid 772 also includes a bore or lumen extending therethrough for receipt of the catheter shaft 12 (FIGS. 120 and 121. Similar to the previously disclosed gripping aids, gripping aid 772 can be used by the user to handle and manipulate the catheter 10 during insertion and withdrawal of the catheter 10 from the patient.

After the user has completed catheterization, the user may remove the gripping aid 772 from the catheter shaft 12 by sliding the gripping aid 772 proximally off the proximal end portion 14 of the catheter shaft 12. The user then turns the gripping aid 772 and inserts the proximal end 14 of the catheter shaft 12 into the hole 784 in the intermediate portion 780 of the gripping aid 772. The gripping aid 772 is now orientated so that the elongated axis of the gripping aid 772 is perpendicular to the elongated axis of the catheter shaft 12. The gripping aid 772 may be slid distally along the catheter shaft 12 or may be push onto the drainage member 22. When the gripping aid 772 extends perpendicular to the catheter shaft 12, the gripping aid 772 defines a water capture element. When the catheter 10 is flushed down the toilet for disposal thereof, the gripping aid 772 captures the momentum of the flushing water to carry the catheter 10 out of the toilet bowl and into the sewer system.

Turning to FIGS. 122 and 123, the water capture element 444 has a generally bowl or cylindrical shape that defines a hollow 446 for capturing flushing water. The water capture element 444 also includes a hole or aperture 448 for receiving passage therethrough of the shaft of the catheter 438. The hole 448 may be of a size to also allow passage of a portion of the drainage member 440. The rim 449 defining hole 448 may be sized to form a friction fit with the catheter shaft or the drainage member 440 so as to secure the water capture element 444 to the catheter 438.

Referring to FIGS. 124 and 125, the water capture element 450 includes a vane 452 which may form from a sheet of material, such as a sheet of water disintegratable polymer. The water capture element 450 also includes a tether 454 having first end 456 attached to the vane 452 and another end 458 including an attachment element 460, such as a clasp or grip, associated therewith. As illustrated in FIG. 125 the attachment element 460 may be used to attach the water capture element 450 to the catheter 438. The attachment element 460 may be attached at any location along the catheter 438. The water capture element 450 may be attached to the catheter during manufacturing or may be attached to the catheter 438 by the user just prior to use or after the catheter has been used to drainage the bladder. After use of the catheter, the user disposes of the catheter in the toilet wherein the flushing water is captured by the vane 452 to propel the catheter down the toilet and through the sanitary system.

FIG. 126 illustrates a conventional drainage member or funnel 462 of a catheter 464. The funnel 462 includes an outer surface 466 that is smooth and tapers outwardly from the proximal end 468 to the distal end 470. Because of the surface is smooth, flushing water smoothly flows over the surface and very little force of the flushing water acts upon the surface of the funnel 462.

Referring to FIG. 127, the drainage member or funnel 474 is a water capture element. In this embodiment, the surface 472 of drainage member 474 includes one or more ridges 478 and one or more grooves 480 extending about the funnel. The ridges 478 and grooves 480 capture flushing water as the water flows by the funnel to propel the catheter down the toilet and/or over a trapway/U-bend pipe.

FIGS. 128-132 illustrate various water capture elements that may be associated with a drainage member. Referring to FIG. 128, the drainage member 482 is a water capture element including a generally rectangular vane 484 associated with the distal end 486 of the drainage member 482 and/or a vane 488 associated with the proximal end 490 of the drainage member 482. In the embodiment shown, the vanes 484, 488 are shown as having relatively the same size. In alternative embodiments, the vanes 484, 488 may have different sizes and shapes.

In FIG. 129, the drainage member 492 includes a generally disc shaped vane 494 associated with the distal end 496 of the drainage member 492 and/or a generally disc shaped vane 498 associated with the proximal end 500 of the drainage member 492. In FIG. 130, the drainage member 502 includes a generally disc shaped concave vane 504 associated with the distal end portion 506 of the drainage member 502. The vane 504 has a concave surface facing the proximal direction of the catheter 508. The drainage member 502 may optionally also include a vane 510 associated with the proximal and 512 of the drainage member 502.

Referring to FIG. 131, the drainage member 514 is a water capture element that includes a proximally extending lip 516 circumferentially surrounding the distal end opening of the drainage member. The outer surface 518 of the drainage member 514 and the proximally extending lip 516 define a space therebetween for capturing water.

FIG. 132 illustrates another embodiment of a drainage element 517 that is a water capture element. In this embodiment, the drainage element has a bowl-like configuration which includes a proximal surface 519 extending radially from the catheter shaft for contacting flushing water.

FIGS. 133-136b illustrate various embodiments of an introducer tip that is a water capture element. Similar to the catheter shown in FIG. 16, the catheter 520 includes a protective sleeve 522 and an introducer tip 524. The protective sleeve 522 surrounds at least a portion of the catheter shaft 526 to separate and enclosed the portion of the catheter shaft 526 from the outside environment. The protective sleeve 522 may have a distal end 528 that is attached to a distal end portion of the catheter shaft 526 or to the funnel 530. A proximal end 532 of protective sleeve 522 is attached to the introducer tip 524. The catheter 520 may be supplied with an introducer tip cap 534 that is attached to the introducer tip 524 to protect the introducer tip 524. Prior to use of the catheter, the user removes introducer tip cap 534 to expose the introducer tip 524. The catheter is then used to drain the bladder in the same manner as described above with reference to the catheter of FIG. 16.

After the bladder is drained, the introducer tip cap 534 may be placed back over introducer tip 524 as shown in FIG. 133 or may be attached to funnel 530. When the introducer tip cap 534 is designed to be attached to funnel 530, the inner surface of the introducer tip cap 534 may include a groove or channel 536 for accepting the rim 538 of the funnel 530.

In the illustrated embodiment, the introducer tip cap 534 includes two lateral vanes 540 extending from either side of the introducer tip cap 534. In FIGS. 135a and 135b, the vanes 540 are generally cup-shaped vanes having openings 542 that are perpendicular to the opening 544 of the introducer tip cap 534. In FIGS. 136a and 136b, the introducer tip cap 534a includes two laterally extending vanes 540a which include openings 542a that are parallel to the opening 544a of the introducer tip cap 534a. It will be understood that the vanes could extend and the openings could face any direction and that the vanes could extend in different directions from each other or the opens could face in different directions. Also the cap could include more or less than the two vanes illustrated.

After use and when the catheter is ready to be disposed of, the user places the catheter having the introducer cap tip 534 attached thereto into the toilet. When the toilet is flushed, the flushing water is captured by the vanes to propel the catheter down the toilet. Furthermore, when the introducer tip cap 534 is attached to the funnel 530 as shown in FIG. 134, a water capture space 546 is defined between the inner surface of the introducer cap and the outer surface of the funnel.

FIGS. 137-139 illustrate various configurations of oversized drainage members or funnels that may be used with a flushable catheter. The oversized drainage member may provide several different features. For example, the oversized drainage members may provide a better gripping surface for the user. The oversized drainage members also may have a tailored density so that the drainage member floats or rests at a desired level within water. The oversized drainage members may also be a water capture element which includes vanes or surfaces for capturing flushing water.

The drainage members 550, 552 and 554 each include an inner drainage passageway 556 which may be outwardly tapered as in a conventional funnel. In FIG. 137, the outer configuration of drainage member 550 is generally circular or doughnut shaped and the drainage member includes a ribbed or otherwise textured center portion 558 that aids in the gripping of the drainage member. In FIG. 138, the drainage member 552 may include a pair of gripping indents 560 on either side of the drainage member 552 for assisting in handling of the drainage member. In FIG. 139, the drainage member 554 includes a groove 562 extending about the center of the drainage member 554 to assist in handling and gripping of the drainage member.

FIG. 140 illustrates a flush enhancing element 564 which may act as a density modifying element and/or a water capture element. The flush enhancing element 564 has a generally bulbous shaped vane or body which includes a generally spherical portion 566 and a projection 568 extending from the generally spherical portion 566. The element 564 does not necessarily need to be bulbous shaped, but may be constructed as any other regular and irregular three-dimensional shape as well, such as generally cubical, disc-shaped, polyhedral, hemispherical, ellipsoidal, cylindrical, conical, and the like. FIGS. 143-145 show flush enhancing elements 564a-564c of various shapes. Element 564a of FIG. 143 has a generally ellipsoid shape portion 566a with a projection 568a extending therefrom. Element 564b includes a generally cylindrical portion 564b having a projection 568b extending therefrom and element 564c is generally mushroom shaped having a generally conical portion 566c including a projection 568c extending therefrom.

The element 564 may be made from a flexible material or a rigid material. Furthermore, the element 564 may be hollow or solid. In one embodiment, the element 564 may be made from an absorbent material that absorbs fluids. For example, the absorbent material may be a porous or foam structure, such as a sponge or sponge-like structure. The absorbent material may have low surface energies or other characteristics that are conducive to enhancing the wettability and/or rate of wettability of the material. In one embodiment, the absorbent material rapidly absorbs fluid, such as an aqueous fluid. The absorbent material may be, for example, hydrophilic wherein the material is made from a hydrophilic material and/or is conditioned to be hydrophilic (by for example, co-casting with a hydrophilic material or coating with a hydrophilic material). The absorbent material may also be a hydrogel. The material from which the element is constructed is also preferably water disintegratable. In one embodiment, the absorbent material may be a porous or foam structure, such as a sponge or sponge-like material, made from a disintegratable material, such as polyvinyl alcohol. For example, the absorbent material may be a polyvinyl alcohol porous or foam structure. Such polyvinyl alcohol sponges may be made, for example, in processes that employ blowing agents or vacuum technology known to those skilled in the art, or in processes that include casting and precipitating, for example, an emulsions or dispersion where the liquid is removed to leave behind porous structures including polyvinyl alcohol or polyvinyl alcohol blended/mixed with other materials.

When the flush enhancing element is constructed from an absorbent material the element may be any of the above described regular or irregular shapes shown in any of the figures of the present application. For example, any of the water capture elements shown in FIGS. 50a-65a may be made in whole or in part of a water absorbent material. The absorbent material also may be optimised to absorb a desired amount of fluid. The absorbent material may be a sponge in which has a selected pore size to maximize the amount of water that may be absorbed by the sponge. In one embodiment, the sponge may absorb an amount of water such that the sponge and the absorbed water therein have a density very close to the density of water or greater than the density of water. In one embodiment, the density of the water containing absorbent material/element may have a density with a range between about 1.0 and about 1.5. Additionally, when the absorbent material is flexible, e.g., flexible spongy material, the element 564 may be compacted or compressed for economical packaging.

Referring to FIGS. 141 and 142, after catheter 570 has been use to drain the bladder and is ready to be disposed of, the user inserts projection 568 of element 564 into the opening 572 of the drainage member 574 to attach the element 564 to the catheter 570. The projection 568 may be retained within opening 572 by friction fit or by an adhesive. After the element 564 has been associated with the catheter 570, the user places the catheter 570 into the toilet for disposal and flushes the catheter 570 down the toilet. As mentioned above, the element 564 may have a density which is conducive for flushing the catheter down the toilet. Alternatively and/or in addition to having a density conducive for flushing, element 564 may act a water capture element that is contacted by the force of the flushing water to propel the catheter 270 down the toilet and/or across the trapway/U-bend pipe.

FIG. 146 illustrates a gripping aid 800 that may also act as a water capture element. The gripping aid 800 includes a proximal end portion 802, distal end portion 804 and an intermediate portion 806 therebetween. The gripping aid 800 also includes a bore or lumen 808 that receives the catheter shaft 12. The proximal and/or distal end portions 802 and 804 may be generally conically shaped and flare outwardly toward the terminal ends thereof. The conical shaped ends portions at their largest cross-sectional length may be two to three times the cross-sectional length of the intermediate portion 806 so as to define a water capture element that may capture the momentum of flushing water when the catheter is flushed down the toilet.

It will be understood that any of the catheters, portions of the catheters and/or water capture members disclosed herein may have a tailored density that results in the catheters, portions of the catheter, and/or water capture elements to float, sink or rest at a desired level or that results in the catheter, portion of the catheter and/or water capture element orientating itself within the water. It will also be understood that any of the water capture elements and/or associated vanes disclosed herein may be employed with any density modified flushable catheters disclosed herein. Furthermore, such water capture elements may be employed with any other suitable type of flushable catheter. It also will be understood that the catheter, any portions of the catheter and/or the water capture elements may be made from any of the water disintegratable or enzymatically hydrolysable materials disclosed herein. Thus, a catheter may include a tailored density, have portions or attachments with a tailored density and/or include a water capture element, which also may have a tailored density. Furthermore, such catheter, portions of the catheter, catheter attachment and/or the water capture element may be made from water disintegratable or enzymatically hydrolysable materials. Additionally, such catheter may be lubricated with any suitable lubricant, such as those describe herein.

Although the present invention is described in light of the illustrated embodiments, it is understood that this for the purposes illustration and not limitation. Other applications, modifications or use of the support or distraction device may be made without departing for the scope of this invention, as set forth in the claims now or hereafter filed.

OTHER ASPECTS

Aspect 1. A flushable urinary catheter, the catheter comprising: a catheter shaft having a proximal insertion end portion and a distal end portion; and a water capture element associated with the catheter wherein the water capture element is configured to receive a force of flushing water impinging thereon so as to propel the catheter down the toilet.

Aspect 2. The catheter of aspect 1 wherein the water capture element is configured to propel the catheter across a U-bend pipe of a sewer system under the force of the flushing water.

Aspect 3. The catheter of any one of the preceding aspects wherein the water capture element extends radially outwardly from a longitudinal axis of the shaft catheter.

Aspect 4. The catheter of aspect 3 wherein the maximum dimension of the water capture element extending radially outwardly from the longitudinal axis of the catheter shaft is at least about 5 to 7 times a radius of the catheter shaft.

Aspect 5. The catheter of any one of the preceding aspects further including a drainage member associated with the distal end portion of the catheter shaft, wherein the water capture element is associated with the drainage member.

Aspect 6. The catheter of any one of the preceding aspects wherein the catheter shaft and/or the water capture element structurally breakdown in water and are preferably comprised of a water disintegratable material.

Aspect 7. The catheter of aspect 6 wherein the water disintegratable material is one or more of a water soluble material, water degradable material, and a water hydrolysable material.

Aspect 8. The catheter of any one of the preceding aspects wherein the water capture element includes a hollow for capturing flushing water.

Aspect 9. The catheter of any one of the preceding aspects wherein the water capture element includes a proximal surface configured for contacting flushing water and receiving the force of the flushing water.

Aspect 10. The catheter of any one of the preceding aspects wherein the water capture element is movable from a collapsed configuration to an expanded configuration.

Aspect 11. The catheter of aspect 10 further including an actuator for actuating movement of the water capture element from the collapsed configuration to the expanded configuration.

Aspect 12. The catheter of aspect 11 wherein the actuator comprises a gripping aid for handling and manipulating the catheter during use.

Aspect 13. The catheter of any one of the preceding aspects where the water capture element includes apertures extending therethrough.

Aspect 14. The catheter of any one of the preceding aspects wherein at least a portion of the catheter and/or the water capture element has a density that causes the water capture element to float at or sink to a desired level within water.

Aspect 15. The catheter of any one of the preceding aspects wherein the water capture element has an opened proximal end and a closed distal end wherein the open proximal end is configured to capture flushing water.

Aspect 16. The catheter of any one of the preceding aspects wherein the water capture element comprises one or more vanes.

Aspect 17. The catheter of aspect 16 wherein the one or more vanes comprises a plurality of vanes.

Aspect 18. The catheter of any one of aspects 16 and 17 wherein the one or more vanes include two or more vanes that extend perpendicular to one another.

Aspect 19. The catheter of any one of aspects 16-18 wherein the one or more vanes include at least two vanes extending parallel to one another.

Aspect 20. The catheter of any one of aspects 16-19 wherein the one or more vanes extend radially outwardly from the longitudinal axis of the catheter shaft.

Aspect 21. The catheter of any one of aspects 16-20 wherein the one or more vanes extend toward the proximal insertion end of the catheter shaft.

Aspect 22. The catheter of any one of aspects 16-21 wherein the one or more vanes comprise at least one generally disc-shaped vane.

Aspect 23. The catheter of aspect 22 wherein the generally disc-shaped vane has a generally concave proximal surface.

Aspect 24. The catheter of any one of aspects 16-23 wherein the one or more vanes comprise at least one generally helical-shaped vane.

Aspect 25. The catheter of any one of aspects 16-24 wherein the one or more vanes comprise at least one generally umbrella-shaped vane.

Aspect 26. The catheter of any one of aspects 16-25 wherein the one or more vanes comprise at least one generally bulbous-shaped vane.

Aspect 27. The catheter of any one of aspects 16-26 wherein the one or more vanes comprise at least one generally bowl-shaped vane.

Aspect 28. The catheter of any one of the proceeding aspects wherein the water capture element expands when contacted with water.

Aspect 29. The catheter of any one of the proceeding aspects wherein the water capture element and/or the catheter shaft are comprised of one or more of pulp cellulose, polyvinyl alcohol and saccharides.

Aspect 30. The catheter of any one of aspects 5-29 wherein the water capture element is integral with the catheter.

Aspect 31. The catheter of any one of aspects 1-29 wherein the water capture element is attachable to the catheter at one or more of the drainage member or the catheter shaft.

Aspect 32. The catheter of any one of the preceding aspects wherein one portion of the catheter has a different density from another portion of the catheter.

Aspect 33. The catheter of any one of the preceding aspects wherein the density of the catheter is graduated along the length of the catheter.

Aspect 34. The catheter of any one of the proceeding aspects wherein at least a portion of the catheter is made from a blend of a polymer and a density modifying additive.

Aspect 35. A flushable catheter, comprising: a catheter shaft; one or more water capture vanes extending in a direction radially outwardly from the longitudinal axis of the catheter shaft, and the one or more water capture vanes being configured to be contacted by flushing water to propel the catheter down the toilet; and wherein the catheter shaft and/or the one or more vanes structurally breakdown when in contact with water.

Aspect 36. The catheter of aspect 35 wherein the catheter and/or catheter shaft are made of water disintegratable materials.

Aspect 37. The catheter of any one of aspects 35 and 36 wherein the one or more vanes are configured to propel the catheter across a U-bend pipe of a sewer system under the force of the flushing water.

Aspect 38. The catheter of any one of aspects 35-37 wherein the maximum dimension of at least one of the one or more vanes extending radially outwardly from the longitudinal axis of the catheter shaft is at least about 5 to 7 times a radius of the catheter shaft.

Aspect 39. The catheter of any one of aspects 35-38 further including a drainage member associated with a distal end portion of the catheter shaft, wherein at least one of the one or more vanes is associated with the drainage member.

Aspect 40. The catheter of any one of aspects 35-39 wherein at least one of the one or more vanes includes a hollow for capturing flushing water.

Aspect 41. The catheter of any one of aspects 35-40 wherein at least one of the one or more vanes includes a proximal surface configured for contacting flushing water and receiving the force of the flushing water.

Aspect 42. The catheter of any one of the aspects 35-41 wherein at least one of the one or more vanes is movable from a collapsed configuration to an expanded configuration.

Aspect 43. The catheter of aspect 42 further including an actuator for actuating movement of the vanes from the collapsed configuration to the expanded configuration.

Aspect 44. The catheter of aspect 43 wherein the actuator comprises a gripping aid for handling and manipulating the catheter during use.

Aspect 45. The catheter of any one of aspects 35-44 wherein at least one of the one or more vanes includes apertures extending therethrough.

Aspect 46. The catheter of any one of aspects 35-45 wherein at least a portion of the catheter and/or at least one of the one or more vanes have a density that causes the one or more vanes to float at or sink to a desired level within water.

Aspect 47. The catheter of any one of aspects 35-46 wherein at least one of the one or more vanes have an opened proximal end and a closed distal end wherein the open proximal end is configured to capture flushing water.

Aspect 48. The catheter of any one of aspects 35-47 wherein the one or more vanes comprise a plurality of vanes.

Aspect 49. The catheter of any one of aspects 35-48 wherein the one or more vanes include two or more vanes that extend perpendicular to one another.

Aspect 50. The catheter of any one of aspects 35-49 wherein the one or more vanes include at least two vanes extending parallel to one another.

Aspect 51. The catheter of any one of aspects 35-50 wherein the one or more vanes extend in a direction toward the proximal insertion end of the catheter shaft.

Aspect 52. The catheter of any one of aspects 35-51 wherein the one or more vanes comprise at least one generally disc-shaped vane.

Aspect 53. The catheter of aspect 52 wherein the generally disc-shaped vane has a generally concave proximal surface.

Aspect 54. The catheter of any one of aspects 35-53 wherein the one or more vanes comprise at least one generally helical-shaped vane.

Aspect 55. The catheter of any one of aspects 35-54 wherein the one or more vanes comprise at least one generally umbrella-shaped vane.

Aspect 56. The catheter of any one of aspects 35-55 wherein the one or more vanes comprise at least one generally bulbous-shaped vane.

Aspect 57. The catheter of any one of aspects 35-56 wherein the one or more vanes comprise at least one generally bowl-shaped vane.

Aspect 58. The catheter of any one of aspects 35-57 wherein at least one of the one or more vanes expands when contacted with water.

Aspect 59. The catheter of any one of the proceeding aspects wherein the one or more vanes and/or the catheter shaft are comprised of one or more of pulp cellulose, polyvinyl alcohol and saccharides.

Aspect 60. The catheter of any one of aspects 35-59 wherein the one or more vanes are attachable to the catheter shaft.

Aspect 61. The catheter of any one of the preceding aspects wherein the catheter self-orientates within water.

Aspect 62. The catheter of aspect 61 wherein the catheter self-orientates to place the water capture element at a desired level within water.

Aspect 63. The catheter of any one of aspects 35-62 wherein the water disintegratable material is one or more of a water soluble material, a water degradable material and a water hydrolysable material.

Aspect 64. The catheter of any one of the preceding aspects wherein the density of the catheter is tailored to result in self orientation of the catheter.

Aspect 65. The catheter of any one of the preceding aspects wherein the water capture elements or water capture vanes is configured to generate a drag force of flushing water that is larger than the retaining forces that urge the catheter to remain within the toilet bowl during flushing.

Aspect 66. The catheter of aspect 65 wherein the retaining forces are one or more of buoyant forces associated with the catheter, water tension forces, and forces of attraction between the catheter and the sidewalls of the toilet.

Aspect 67. The catheter of any one of the preceding aspects wherein the water capture element and/or the water capture vanes are comprised in whole or in-part of an absorbent material.

Aspect 68. The catheter of aspect 66 wherein the absorbent material is a sponge, sponge-like or hydrogel material.

Aspect 69. A flushable urinary catheter, comprising: a catheter shaft having a proximal insertion end portion, a distal end portion and a middle portion therebetween; and wherein one or more of the portions of the catheter shaft have a density that is tailored to facilitate flushing of the catheter down the toilet and/or across a U-bend pipe.

Aspect 70. The catheter of aspect 69 wherein at least one of the proximal insertion end, distal end and middle portions of the catheter shaft has a density that is different from another portion of the catheter shaft.

Aspect 71. The catheter of any one of aspects 69 and 70 wherein the proximal insertion end portion of the catheter shaft has a density that is different from at least one of the middle and distal end portions of the catheter shaft.

Aspect 72. The catheter of any one of aspects 69 and 70 wherein the middle portion of the catheter shaft has a density that is different from at least one of the proximal insertion end and distal end portions of the catheter shaft.

Aspect 73. The catheter of any one of aspects 69 and 70 wherein the distal end portion of the catheter shaft has a density that is different from at least one of the proximal insertion end and middle portions of the catheter shaft.

Aspect 74. The catheter of any one of aspects 69-73 wherein the proximal insertion end portion of the catheter shaft has a greater density than at least one of the middle and distal end portions of the catheter shaft.

Aspect 75. The catheter of any one of aspects 69-73 wherein the middle portion of the catheter shaft has a greater density than at least one of the proximal insertion end and distal end portions of the catheter shaft.

Aspect 76. The catheter of any one of aspects 69-73 wherein the distal end portion of the catheter shaft has a greater density than at least one of the proximal insertion end and middle portions of the catheter shaft.

Aspect 77. The catheter of any one of aspects 69-75 wherein the density of the catheter gradually decreases in the direction of the distal end portion of the catheter shaft.

Aspect 78. The catheter of any one of aspects 69-73, 75 and 76 wherein the density of the catheter gradually increases in the direction of the distal end portion of the catheter shaft.

Aspect 79. The catheter of any one of aspects 69-73 wherein the density of the catheter shaft gradually decreases from the middle portion of the catheter shaft in both the directions of the proximal insertion end portion and the distal end portion of the catheter shaft.

Aspect 80. The catheter of any one of aspects 69-73 wherein the density of the catheter shaft gradually increases from the middle portion of the catheter shaft in both the directions of the proximal insertion and distal end portions of the catheter shaft.

Aspect 81. The catheter of any one of aspects 69-80 wherein the catheter includes a drainage member associated with the distal end portion of the catheter shaft and the drainage member has a density which is different from at least one of the proximal insertion end, middle and distal end portions of the catheter shaft.

Aspect 82. The catheter of aspect 81 wherein the density of the drainage member is greater than the density of at least one of the proximal insertion end, middle and distal end portions of the catheter shaft.

Aspect 83. The catheter of aspect 81 wherein the density of the drainage member is less than the density of at least one of the proximal insertion end, middle and distal end portions of the catheter shaft.

Aspect 84. The catheter of any one of aspects 69-83 wherein a density of the catheter is graduated along the length of the catheter.

Aspect 85. The catheter of any one of aspects 69-84 wherein the catheter is constructed from materials of different density.

Aspect 86. The catheter of any one of aspects 69-85 wherein the catheter is made from a blend of a polymer and density modifying additives.

Aspect 87. The catheter of any one of aspects 69-86 further including a water capture element associated with the catheter wherein the water capture element is configured to be contacted by flushing water to propel the catheter down the toilet and/or across a U-bend pipe.

Aspect 88. The catheter of any one of aspects 69-87 wherein the catheter self-orientates when within water.

Aspect 89. The catheter of any one of the proceeding aspects wherein the density of at least one of the portions of the catheter is between about 0.4 g/cm$^3$ and about 1.2 g/cm$^3$, and preferably between about 0.68 g/cm$^3$ and about 0.89 g/cm$^3$.

Aspect 90. The catheter of any one of the proceeding aspects wherein the catheter has a compact configuration for flushing down the toilet.

Aspect 91. The catheter of any one of the proceeding aspects further including a securing element for securing the catheter in the compact configuration.

Aspect 92. The catheter of aspect 91 wherein the securing element is one or more of a securing strip, a gripping aid, a bag and a tray.

Aspect 93. The catheter of aspect 92 wherein the gripping aid secures the catheter in a U-Shaped or looped configuration.

Aspect 94. The catheter of aspect 91 further including a gripping aid wherein the securing element is associated with gripping aid.

Aspect 95. The catheter of aspect 91 wherein at least on securing element is associated with an insertion tip or a drainage member of the catheter shaft.

Aspect 96. The catheter of any of aspects 69-95 wherein at least a portion of the catheter structurally breaks down when in contact with water and is preferably made from a water disintegratable material.

Aspect 97. The catheter of aspect 95 wherein the water disintegratable material is one or more of a water soluble material, water degradable and a water hydrolysable material.

Aspect 98. A flushable catheter that may be disposed of by flushing down the toilet, the catheter comprising: a catheter shaft having a proximal insertion end portion and a distal end portion; a drainage member associated with the distal end portion of the catheter shaft; and wherein the catheter shaft and/or the drainage member structurally break down when in contact with water, and at least a section of the catheter has material properties and/or geometries that results in self-orientation of the catheter when the catheter is placed in water.

Aspect 99. The catheter of aspect 98 wherein the catheter shaft and/or drainage member are made from a water disintegratable material.

Aspect 100. The catheter of any one of aspects 98 and 99 wherein the catheter self-orientates so that the distal end portion of the catheter shaft sinks lower in the water than the proximal insertion end portion.

Aspect 101. The catheter of any one of aspects 98 and 99 wherein the catheter self-orientates so that the proximal insertion end portion of the catheter shaft sinks lower in the water than the distal end portion.

Aspect 102. The catheter of any one of aspects 98-101 further including a water capture element associated with the catheter and wherein the catheter self-orients so that the water capture element floats or sinks to a selected level within the water.

Aspect 103. The catheter of aspect 102 wherein the water capture element is attachable to the catheter.

Aspect 104. The catheter of any one of aspects 102 and 103 wherein the water capture element includes a density tailored to facilitate flushing of the catheter down the toilet and/or across a U-bend pipe.

Aspect 105. The catheter of any one of aspects 98-104 wherein the material property is tailored density and/or surface free energy.

Aspect 106. The catheter of any one of aspects 98-105 wherein the water disintegratable material is one or more of a water soluble material, enzyme hydrolysable and a water hydrolysable material.

Aspect 107. The catheter of any one of the proceeding aspects wherein the catheter shaft is lubricated.

Aspect 108. The catheter of aspect 107 wherein the lubricity of the lubricated catheter shaft is selected to enhance flushability.

Aspect 109. The catheter of any one of aspects 107 and 108 wherein the lubricity of the lubricated catheter shaft is selected to resist or prevent sticking to toilets and pipes.

Aspect 110. A flushable urinary catheter, comprising: a catheter shaft having a proximal insertion end portion, a distal end portion and a middle portion therebetween; a drainage member associated with the catheter shaft; and wherein one or more of the portions of the catheter shaft and the drainage member have a buoyancy that is tailored to facilitate flushing of the catheter down the toilet and/or across a U-bend pipe.

Aspect 111. The catheter of aspect 110 wherein one or more portions of the catheter shaft and the drainage member have a different buoyancy than other portions of the catheter shaft and the drainage member.

Aspect 112. A flushable catheter assembly, comprising: a catheter; and an flush enhancing element attachable to the catheter.

Aspect 113. The catheter assembly of aspect 112 wherein the flush enhancing element is one or more of a density modifying element and a water capture element.

Aspect 114. The catheter assembly of any one of aspects 112 and 113 wherein the flush enhancing element comprises a bulbous shape.

Aspect 115. The catheter assembly of any one of aspects 112-114 wherein the flush enhancing element is attachable to a drainage member of the catheter.

Aspect 116. The catheter assembly of any one of aspects 112-115 wherein the flush enhancing element is comprised in whole or in-part of an absorbent material.

Aspect 117. The catheter assembly of aspect 116 wherein the absorbent material is a sponge, sponge-like or hydrogel material.

What is claimed is:

1. A flushable urinary catheter configured for disposal by flushing down a toilet, the catheter comprising:
   a catheter shaft having a proximal insertion end portion and a distal end portion, a drainage member associated with the distal end portion of the catheter shaft; and
   a water capture element associated with the drainage member wherein the water capture element is configured to receive a force of flushing water impinging thereon so as to propel the catheter out of a toilet bowl and down the toilet.

2. The catheter of claim 1 wherein the water capture element is configured to propel the catheter across a U-bend pipe of a sewer system under the force of the flushing water.

3. The catheter of claim 1 wherein the water capture element extends radially outwardly from a longitudinal axis of the catheter shaft.

4. The catheter of claim 3 wherein the maximum dimension of the water capture element extending radially outwardly from the longitudinal axis of the catheter shaft is at least about 5 to 7 times a radius of the catheter shaft.

5. The catheter of claim 1 wherein the catheter shaft and/or the water capture element are comprised of a water disintegratable material.

6. The catheter of claim 5 wherein the water disintegratable material is one or more of a water soluble material, water degradable material, and a water hydrolysable material.

7. The catheter of claim 1 wherein the water capture element includes a hollow for capturing flushing water.

8. The catheter of claim 1 wherein the water capture element includes a proximal surface configured for contacting flushing water and receiving the force of the flushing water.

9. The catheter of claim 1 wherein the water capture element is movable from a collapsed configuration to an expanded configuration.

10. The catheter of claim 9 further including an actuator for actuating movement of the water capture element from the collapsed configuration to the expanded configuration.

11. The catheter of claim 10 wherein the actuator comprises a gripping aid for handling and manipulating the catheter during use.

12. The catheter of claim 1 wherein the water capture element includes apertures extending therethrough.

13. The catheter of claim 1 wherein at least a portion of the catheter and/or the water capture element has a density that causes the water capture element to float at or sink to a desired level within water.

14. The catheter of claim 1 wherein the water capture element has an opened proximal end and a closed distal end wherein the open proximal end is configured to capture flushing water.

15. The catheter of claim 1 wherein the water capture element comprises one or more vanes.

16. The catheter of claim 15 wherein the one or more vanes comprises a plurality of vanes.

17. The catheter of claim 15 wherein the one or more vanes include two or more vanes that extend perpendicular to one another.

18. The catheter of claim 15 wherein the one or more vanes include at least two vanes extending parallel to one another.

19. The catheter of claim 15 wherein the one or more vanes extend radially outwardly from the longitudinal axis of the catheter shaft.

\* \* \* \* \*